UNITED STATES PATENT …

United States Patent [19]
Obonai et al.

[11] Patent Number: 6,032,409
[45] Date of Patent: Mar. 7, 2000

[54] SUPPORT FOR CULTIVATING PLANT

[75] Inventors: Yasuhiro Obonai; Takehiko Mukoyama, both of Yamanashi, Japan

[73] Assignee: Mukoyama Orchids, Ltd., Yamanashi, Japan

[21] Appl. No.: 09/029,638

[22] PCT Filed: Jul. 29, 1996

[86] PCT No.: PCT/JP96/02128

§ 371 Date: Mar. 4, 1998

§ 102(e) Date: Mar. 4, 1998

[87] PCT Pub. No.: WO97/08938

PCT Pub. Date: Mar. 13, 1997

[30] Foreign Application Priority Data

Sep. 5, 1995 [JP] Japan ................................. 7-251766
Mar. 6, 1996 [JP] Japan ................................. 8-049364

[51] Int. Cl.⁷ ......................... A01G 17/06; A01G 1/04; A01C 1/04; C09B 67/00; C08K 3/02
[52] U.S. Cl. ........................... 47/44; 47/1.01; 47/56; 47/65.7; 8/555; 524/789
[58] Field of Search .................. 47/44, 1.01, 65.7, 47/56; 8/555; 524/789

[56] References Cited

FOREIGN PATENT DOCUMENTS

| | | |
|---|---|---|
| 0122797 | 10/1984 | European Pat. Off. . |
| 138123 | 6/1987 | Japan . |
| 63-303704 | 12/1988 | Japan . |
| 349525 | 7/1991 | Japan . |
| 474981 | 11/1992 | Japan . |
| 560250 | 8/1993 | Japan . |
| 6276873 | 10/1994 | Japan . |

OTHER PUBLICATIONS

"General Introduction to Horticultural of Flowers", published on Mar. 10, 1995.

"Iwanami Biological Dictionary", published on Mar. 10, 1983.

"Technique in Plant Tissue Culturing", published on Oct. 20, 1983.

Tanaka et al., "Critical Kinetics of Volume Phase Transition of Gells", The American Physical Society, vol. 55, No. 22, Nov. 25, 1985.

*Primary Examiner*—Ponnathapu Achutamurthy
*Assistant Examiner*—Tekchand Saidha
*Attorney, Agent, or Firm*—Leydig, Voit & Mayer, Ltd.

[57] ABSTRACT

A vessel for growing a plant, comprising: a base material 11 in the form of a vessel which is capable of accommodating therein at least a part of a plant; and a hydrogel-forming polymer 12 having a crosslinked structure disposed inside of the vessel-form base material 11 is disclosed. When such a vessel is used, a transfer operation for the plant can be automated, and any damage caused by transferring the plant can be reduced.

8 Claims, 22 Drawing Sheets

SINGLE-CELL PARTITION
(WITH EXTENSION)

4-CELL PARTITION

<CHECKERED PATTERN-TYPE>

<SPOT-TYPE>

AVERAGE TIME-DEPENDENT TEMPERATURE CHANGE
IN ONE DAY IN TEST PERIOD

SUPPORT FOR CULTIVATING PLANT

This application is a 371 of PCT/JP96/02128 filed Jul. 29, 1996.

TECHNICAL FIELD

The present invention relates to vessel or sheet for growing (hereinbelow, the term "grow" is used in a meaning such that it also includes the germination of a plant, and the growth thereof after the germination) a plant, a support for cultivating a plant, and an agent for modifying (or reforming) soil, which are suitably usable for tissue culturing or the germination of a seed and the growth thereof after the germination, and the growth of a plant in farm cultivation; and a method of growing (in the present specification, the term "growth" is used in a meaning such that it also includes germination and growth after the germination) a plant, while using a gel-like support substantially as it is which has been used in the artificial culturing, whereby a plant can be cultivated in an environment wherein aeration or ventilation is not restricted (e.g., in farm cultivation).

More specifically, the present invention relates to a vessel or sheet for growing a plant (hereinbelow, this term is used in a meaning such that it also includes "seed"), which enables easy transfer of the plant, the promotion of the germination or growth of the plant, and marked reduction in the necessity for strict control of water, etc.;

- a support to be used for supporting or carrying a plant in the cultivation of the plant; and a soil-modifying agent for supporting or carrying a plant in the cultivation of the plant in combination with another plant-supporting carrier (such as soil), whereby the physical, chemical and microbiological properties of the carrier can be improved or modified on the basis of the application of such a soil-modifying agent to another carrier such as soil; and
- a method of growing a plant which enables continuous growth of a plant from the culturing to cultivation thereof; and particularly, a method of continuously growing a plant wherein at the time of the transfer from the culturing thereof in a vessel into farm cultivation thereof, the support (or planting material) which has been used in the culturing of the plant can also be used as it is in the cultivation thereof, thereby to omit or simplify the transferring step for the plant, to prevent the physical damage to the root thereof, and to enable the smooth growth of the plant after the transfer thereof into the cultivation step.

In the present specification, "culture" (or culturing) of a plant refers to the growth or multiplication of the plant under a condition (mainly in a vessel) such that the aeration or ventilation into the plant-growing system is controlled or limited; and "cultivation" of a plant refers to the growth or multiplication of the plant under a condition (mainly in a greenhouse or open-air field) such that the aeration or ventilation into the plant-growing system is not limited. With respect to such definition of the culture, it is possible to refer to "Technique in Plant Tissue Culturing" edited by Takeuchi et al., Page 1 (1983), Asakura Shoten; and "Iwanami Biological Dictionary" (3rd edition) edited by Yamada et al., Page 1006 (1983), Iwanami Shoten.

BACKGROUND ART

In recent years, it has attracted much attention to develop a technique for growing or regenerating a plant having a character or trait suitable for an intended purpose. Among these growing and regenerating techniques, a plant tissue culture technique, i.e., a technique wherein a part of a plant is separated from the main body thereof, and is grown in the inside a culturing vessel has particularly attracted much attention, since it enables the mass multiplication of a genetically identical clone in a short period of time (Kiyoshi Okawa "General Introduction to Horticultural of Flowers", page 54, 1995, Yokendo).

Heretofore, in the production of a plant (mainly, a plantlet) using a plant tissue-culturing technique, agar gel has been used as a support therefor. However, the agar gel has a characteristic such that it hardly absorb water content again, after it discharges water content due to the evaporation of water or the absorption of water into the plant. Particularly, in an open-system cultivation environment such as farm cultivation, the water content-retaining function of the agar and the plant-retaining function thereof as a gel are rapidly decreased. Accordingly, it is naturally impossible to use the agar gel as the support (or planting material) in the open-system farm cultivation.

From such a viewpoint, it is necessary to remove the agar gel at the time at which a plantlet is transferred from the culture thereof in a vessel into the farm cultivation thereof. However, it is inevitable to manually conduct a step of removing the agar gel one by one with respect to the plantlet, and therefore such a removing step not only requires much labor and long time, but also poses some problems such that it damages the root of the plantlet, is liable to cause a root decay (or root rot) phenomenon, etc.

On the other hand, in the case of the culture of a very small plantlet (minute plantlet), a saccharide is generally added into the liquid culture medium to be used for the culture. The reason for this is that, in general, such a minute plantlet does not have an organ such as albumen of a seed, leaf and stem portion thereof for conducting a photosynthesis reaction is not sufficiently developed, and therefore it is necessary to add a carbon source which the minute plantlet can absorb directly. In addition to the case of the tissue-cultured plantlet, in a case of a seed having no albumen such as that of an orchid (Orchidaceae) plant, a minute plantlet which has been germinated in a vessel is subjected to a saccharide-involving (or saccharide-relating) culture process for a similar reason. However, since the saccharide which has been added into the plant-growing system promotes the propagation of various germs, it is substantially impossible to use the agar gel containing a saccharide as it is in an open-system (non-sterilized) environment such as farm cultivation.

As described above, in a case where the conventional method of growing a plant by using agar gel, it is substantially impossible to continuously grow the plant from the culture thereof to farm cultivation thereof (by using the support used for the culture as it is), and therefore the step of removing the agar is required. In addition, since such a agar-removing step must be conducted by using manual operations, a considerable period of time is required, and further, the step has problems such that it damages the root of the plant, and various germs are liable to propagate due to the presence of the remaining agar gel so as to cause a root decay phenomenon.

In addition to the above-mentioned problem of the transfer from the "culture" to the "cultivation", in the course of plant growth, it is also an important subject to control the amount of the supply of water content, a nutrient, etc., to the plant.

In view of the physiology of a plant, "water" is one of the environmental factors which exerts the greatest influence upon the growth of the plant, and particularly, it is an element essential for the photo-synthesis. The absorption of the water content, which is an extremely important environmental factor, is mainly concerned with the transpiration due to "stomata" as openings of the back surface of a leaf of the plant.

More specifically, when the water content of cells constituting a plant is decreased by the transpiration of water, the water content in the plant assumes a non-equilibrium state, and the plant absorbs water content in soil through the root thereof on the basis of the "transpiration pressure" as an action for retaining the non-equilibrium state in an equilibrium.

The above-mentioned stoma also has a function of taking $CO_2$ in, which is necessary for the photo-synthesis, from the air. However, since the water content in the mesophyll cells, wherein the photo-synthesis is mainly to be conducted, is transpired due to the presence of the openings of the stomata, the water content in the mesophyll cells is required to be supplemented promptly. In other words, water must be supplied plentifully to the plant along with the absorption of solar energy and $CO_2$ so that plant conducts the photosynthesis more effectively.

In the daytime environment wherein the temperature is high and the light quantity of the sunlight is large, when the water content which a plant can utilize is insufficient in the cultivating soil, or when the water-absorbing ability of the root of the plant is lowered, the water content in the plant is decreased, and the water content in the mesophyll cells wherein the photo-synthesis is mainly to be conducted is also decreased. As a result, not only the photo-synthesis is markedly inhibited, but also the photo-synthesis product is markedly decreased so that the growth of the plant per se is suppressed, and there is a danger such that the plant is withered to death in the course of time. Further, when the water content in soil becomes insufficient, the concentration of mineral salts contained in the soil is increased. On the contrary, when the water content in soil becomes excessive, the supply of oxygen to the root of the plant becomes insufficient. In both of these cases, there is a fear such that the plant is adversely affected.

On the other hand, "temperature" is also one of the environmental factors which greatly affects the growth of a plant. For example, the absorption of mineral salts through the root of a plant is increased along with an increase in temperature, but the absorption will have a maximum when the temperature reaches at a certain value, and is sharply decreased at a higher temperature than such a value. It is known that the maximum value of the mineral salt absorption is present in the neighborhood of 40° C. in most of the plants. The absorption of nutrients in a lower temperature region is mainly based on a simple diffusion phenomenon, but the ratio of active nutrient absorption based on a biochemical absorption process is increased along with an increase in temperature. In a high-temperature region of 40° C. or more, the deactivation of an enzyme system relating to the biochemical absorption process is regarded as a cause of sharp decrease in the nutrient-absorbing rate. Accordingly, the control of water in the cultivating soil and the control of the amount and concentration of nutrients with respect to a temperature change is very important technique for the cultivation of a plant.

On the other hand, from a viewpoint of technique of crop production, cultivation in open-air field has heretofore been conducted in a natural (or non-artificial) environment with respect to crops such as grain plant, vegetables, flowering plants, and fruit trees. However, in the open-air field cultivation, since the production amount of the crops are greatly varied due to a violent change in temperature during four seasons, unstable rainfall conditions, etc., the development of the agriculture as an industry has rather been limited.

In recent years, the cultivation of crops in facilities such as greenhouse has been popularized for the purpose of overcoming the above-mentioned problems in the open-air field cultivation or for the purpose of shipping the crops throughout one year (in any season constituting one year). As a result, it becomes possible to supply agricultural products stably.

However, in the facility cultivation, the production cost of the crops inevitably becomes high. The reason for this is that, in the facility cultivation, the facility-and-equipment investment becomes very large, which is necessary for the construction of the facility main body such greenhouse, the internal equipment such as watering apparatus in the facility, or environment-controlling instrument for regulating the temperature, concentration of nutrients, light intensity, etc., in the facility. On the other hand, in the above-mentioned open-air field cultivation, in many cases, there is required a large investment in the irrigation and watering facilities, etc., for the purpose of overcoming the influence of sudden changes in the natural environment.

In general, the use of chemical-type fertilizers in place of organic-type fertilizers has been considered as one of the important factors which have supported the development of modern agriculture. However, the ratio of the chemical-type fertilizer which is to be actually absorbed into a plant is considered to be usually below 30%. Accordingly, in recent years, there is a fear such that soil is deteriorated and the environment is polluted globally due to the use of the chemical-type fertilizer, and the natural resources to be used as the raw material for producing the chemical-type fertilizer are even exhausted.

In order to solve the above-mentioned problems, there has strongly been demanded a method of effectively applying a fertilizer to a plant, or an improvement in "carrier for supporting a plant" such as soil with which a fertilizer is effectively applied to a plant.

In recent years, in addition to the above-mentioned problem in the "carrier", the improvement in a "vessel" for growing a plant also becomes an important subject in the field of the plant growth.

Heretofore, the transfer of a plant is required to be conducted by long-term troublesome manual operations. Further, there are pointed out various problems such that the above-mentioned manual operations damage the plant, or they considerably impair the initial (or early-phase) growth of the plant after the transfer operation, etc. From such a viewpoint, it has strongly been desired to automate the transfer operation of a plant, to reduce the transferring damage (or rooting damage) at the time of the transfer operation, or to promote the initial growth of the plant after the transfer operation.

In addition, the conventional vessel for growing a plant has a problem such that it is liable to deteriorate the physical environment of the rhizosphere of the plant. In general, when the root of a plant is extended to the wall surface of a vessel, it is further extended downward along the wall surface, and when the root reaches the bottom surface of the vessel, it is extended so as to be formed into a coil-like shape along the bottom surface in many cases. It is considered that such a phenomenon of root extension is based on the property of the root of extending in the direction of the gravity, and the property thereof of extending due to the contact surface stimulus to be applied to the root. On the other hand, in the cultivation of a plant using a vessel, it has heretofore been investigated particularly intensively to find what kind of supporting carrier (such as soil) is optimum in view of the growth of the plant. Accordingly, the investigation of the physical environment of internal surface of the vessel has been insufficient.

In general, the physical environment of the interior of the carrier for retaining a plant is utterly different from that of the internal surface of the vessel. In the latter environment, i.e., in the neighborhood of the internal surface of the vessel, since the difference in the temperature (hot and cold) and humidity (dry and wet) is large, there is particularly liable to occur a problem such that the growing point of the root which contacts the internal wall surface, or an intermediate portion of the root which is extended along the internal wall surface, causes browning and fatal withering.

Heretofore, specific examples of the vessel or sheet to be used for the growth of a plant, include unglazed (earthenware) pots, plastic pots, vinyl pots, planters, trays for "plug-type" plantlet, trays for plantlet, paper pots, vinyl sheets, etc. In any of these vessels, when the material of the vessel (such as usual plastic material) is one which intercepts the circulation of water or outside air, the place in the neighborhood of the internal wall surface of the vessel is a place wherein water is liable to be accumulated, and a root decay phenomenon is liable to occur. On the other hand, when the material of the vessel is one which enables the circulation of outside air (such as unglazed earthenware and paper), on the contrary, the place in the neighborhood of the internal wall surface of the vessel is a place wherein water is liable to be insufficient, and the growth of the plant is liable to be markedly hindered.

In addition, the vessel to be used in the farm cultivation is generally one having an open-system portion in the upper and lower parts thereof. Accordingly, after a watering operation, the supplied water is promptly drained from the lower part of the vessel through the plant-supporting carrier, thereby to cause problems such as the necessity for excessive watering operations and the flowing-out of nutrients. Further, in the case of a vessel to be used in general homes, a "pan" for receiving water, etc., drained from the lower part of the vessel is required.

Further, when such an open-type vessel is used, since the amount of water immediately before the watering operation is liable to be sharply decreased suddenly, the concentration of nutrients is sharply increased, whereby the plant can be adversely affected. On the other hand, when the amount of water to be used in the watering operation is increased, the frequency of the watering operation is increased, or the conventional vessel and soil having a high water-retaining property are selected for the purpose of improving such a situation, the accumulation of excessive water lasting immediately after the watering inhibits the supply of oxygen to the root, and microorganisms adversely affecting the plant are propagated, whereby a root decay phenomenon is liable to occur. On the contrary, when the plant-growing system is dried for the purpose of promoting the supply of oxygen, or of suppressing the propagation of microorganisms adversely affecting the plant, the above-mentioned problems of a decrease in the water content and the concentration of nutrients become severer, and therefore a fertilizer must be supplied to the plant in a smaller amount than that of the fertilizer required by the plant.

As described above, the present plant cultivation using a plant-growing vessel is caught in a vicious circle or falls into a self-contradiction, and therefore such a condition makes it difficult to cause a plant to exhibit its growing power to the maximum.

Further, the upper portion of the above-mentioned open-type vessel is in a completely open state, and therefore the upper portion of a plant-supporting carrier is liable to be dried than the lower portion thereof so that aqueous or moisture condition in the vessel becomes ununiform and such a condition is liable to adversely affect the plant.

On the other hand, it is not usual to use a vessel having a closed-type lower portion. The reason for is that when the conventional vessel is simply used as one having a closed-type lower portion in combination with the conventional soil, the residence or retention of water becomes marked, and such a phenomenon is extremely liable to cause the above-mentioned insufficient oxygen supply, and root decay phenomenon due to the propagation of pathogens.

As described above, in the conventional plant-growing vessel or sheet, the environment of the rhizosphere is not suitable for the growth of a plant (inclusive of the germination of a seed and the growth thereof after the germination). Accordingly, when such a conventional vessel or sheet is used, there is required a complicated combination or regulation of the amount of water for the watering, the frequency of the watering, the concentration of solutions such as fertilizer, etc., and therefore the strict control of these factors has required great costs.

In general, with respect to various kinds of plant, the internal volume of the most suitable growing vessel has been known empirically depending on the kind, size thereof, etc. It is said that when the root of a plant is grown in soil so as to reach the wall of the growing vessel, the resultant mechanical contact stimulus promotes the origination of a new root. From such a viewpoint, the origination of root of the plant becomes better as the volume of the vessel becomes smaller. On the other hand, the internal volume of the vessel closely relates to the amount of water and nutrients stored therein which are to be supplied to the plant, and therefore, in general, the volume of the vessel of not lower than a certain level is required for the growth of the plant.

The circumstances of general cultivation farmhouses are those as described above. In recent years, however, in general homes, a many kinds of plant-growing vessels have been used in so-called "private (vegetable) gardens". In general homes, since they do not have skilled experience or technique, unlike in the cultivation farmhouses, it is further difficult to suitably grow the plant, as compared with in the case of the cultivation farmhouses.

An object of the present invention is to provide a plant-cultivating support or a soil-modifying (or reforming) agent, which can solve the above-mentioned problems encountered in the prior art.

Another object of the present invention is to provide a plant-cultivating support or a soil modifying agent, which can suitably control the amount of water, the amount of nutrients, or the amount of a plant growth-regulating substance to be supplied to a plant so as to meet the demand of the plant, in accordance with a change in the external environmental factors such as temperature.

A further object of the present invention is to provide a plant-cultivating support or a soil modifying agent, which can enhance the productivity by saving labor to be required in open-airfield cultivation and cultivation in facilities, and by reducing the facility costs.

A further object of the present invention is to provide a method of effectively growing a plant while using a plant-cultivating support or a soil-modifying agent.

A further object of the present invention is to provide a vessel or sheet for cultivating a plant, which can solve the above-mentioned problems of the conventional plant-cultivating vessel.

A further object of the present invention is to provide a plant-cultivating vessel or sheet, which can automate the transferring operation for a plant, and further can reduce the transferring damage to the plant at the time of the transferring operation.

A further object of the present invention is to provide a plant-cultivating vessel or sheet, which can suitably control the environment in the rhizosphere of the plant, while strict control of water, etc., is not necessarily required.

A further object of the present invention is to provide a plant-cultivating vessel or sheet, which has an ability to store water and/or nutrients which are necessary for the germination or growth of a plant.

A further object of the present invention is to provide a method of cultivating a plant, which has solved the above-mentioned problems encountered in the prior art.

A still further object of the present invention is to provide a method of cultivating a plant by using a support (or planting material) which can be used continuously from the culturing of the plant to the cultivation thereof.

DISCLOSURE OF INVENTION

As a result of earnest study, the present inventors have found that it is extremely effective in solving the above-mentioned problems to use a polymer which is capable of providing a hydrogel which has a crosslinked structure and shows a reversible change in a specific physical property, as a medium or a portion thereof (soil-modifying agent) for supporting a plant at the time of the cultivation of the plant.

The plant-cultivating support or soil-modifying agent according to the present invention is based on the above-mentioned discovery, and comprises: a hydrogel-forming polymer having a crosslinked structure and showing a decrease in the equilibrium water absorption thereof along with an increase in temperature in the temperature range of not lower than 0° C. and not higher than 70° C., the equilibrium water absorption being reversibly changeable with respect to temperature.

The present invention also provides a support for cultivating a plant, comprising, at least a carrier for supporting a plant; and a soil-modifying agent, comprising a hydrogel-forming polymer having a crosslinked structure and showing a decrease in the equilibrium water absorption thereof along with an increase in temperature in the temperature range of not lower than 0° C. and not higher than 70° C., the equilibrium water absorption being reversibly changeable with respect to temperature.

The present invention further provides a method of cultivating a plant, comprising:
disposing a plant-cultivating support at least around a plant; and
cultivating the plant while supporting the plant by the plant-cultivating support;
wherein the plant-cultivating support comprises a hydrogel-forming polymer having a crosslinked structure a and shows a decrease in the equilibrium water absorption thereof along with an increase in temperature in the temperature range of not lower than 0° C. and not higher than 70° C., the equilibrium water absorption being reversibly changeable with respect to temperature.

The present invention further provides a method of cultivating a plant, comprising:
disposing a plant-cultivating support at least around a plant; and
cultivating the plant while supporting the plant by the plant-cultivating support;
wherein the plant-cultivating support comprises a plant-supporting carrier, and a soil-modifying agent added to the carrier in an amount of 0.1–10 wt., in terms of the weight in a dry state; the soil-modifying agent comprising a hydrogel-forming polymer having a crosslinked structure and showing a decrease in the equilibrium water absorption thereof along with an increase in temperature in the temperature range of not lower than 0° C. and not higher than 70° C., the equilibrium water absorption being reversibly changeable with respect to temperature.

As a result of further study based on the above discovery, the present inventors have also found that it is extremely effective in solving the problems in the prior art to dispose a polymer capable of providing a hydrogel having a crosslinked structure, in at least a portion of the internal surface of a vessel (e.g., bottom face and/or side face of the plant-growing vessel).

The vessel for growing a plant according to the present invention is based on the above discovery and comprises: a base material in the form of a vessel which is capable of accommodating therein at least a part of a plant; and a hydrogel-forming polymer disposed in the inside of the vessel-form base material; the hydrogel-forming polymer having a crosslinked structure.

The present inventors have also found that the effect of growing a plant may be obtained in the same manner as in the above-mentioned "plant-growing vessel wherein a hydrogel-forming polymer is disposed in the inside thereof", even when a sheet-like material having the above-mentioned hydrogel-forming polymer disposed on a surface thereof is provided on an internal wall of the conventional plant-growing vessel.

The sheet for growing a plant according to the present invention is based on the above discovery, and comprises: a base material in the form of a sheet; and a hydrogel-forming polymer disposed on at least one of the surfaces of the sheet; the hydrogel-forming polymer having a crosslinked structure.

In the above-mentioned vessel or sheet according to the present invention, it is preferred that the hydrogel-forming polymer shows a decrease in the equilibrium water absorption thereof along with an increase in temperature in the temperature range of not lower than 0° C. and not higher than 70° C., the equilibrium water absorption being reversibly changeable with respect to temperature.

Further, in the present invention, when the hydrogel-forming polymer is in the form of powder or particles, the powder or particles may preferably have a dimension of 0.1 $\mu$m–5 mm in a dry state.

As a result of further study, the present inventors have found that a gel-like support comprising at least water and a polymer capable of forming a hydrogel having a crosslinked structure exhibits a certain bacteriostatic (or bacteria growth-inhibiting) property, not only under an aeration (or ventilation)-restricted environment (at the time of culturing) but also under an aeration non-restricted environment (at the time of cultivation), on the basis of the characteristic of water disposed in the crosslinked structure of the gel. As a result of further study based on such a discovery, the present inventors have found that the gel-like support having a bacteriostatic property may be used as a support (or planting material) continuously, during the growth of a plant extending from the aeration-restricted environment to the aeration non-restricted environment.

The method of growing a plant according to the present invention is based on the above discovery, and comprises:

(a) culturing a plant under a ventilation-restricted condition by using a gel-type support comprising at least water and a hydrogel-forming polymer having crosslinked structure; and (b) cultivating the plant under a ventilation non-restricted condition by using the gel-like support disposed in contact with the plant after the culturing, substantially as it is.

In the above-mentioned plant-growing method according to the present invention, the term "using a gel-like support substantially as it is" means a state wherein the "positive or intentional removal operation" for the gel-like support is not conducted with respect to the gel-like support attached to the plant after the culturing process, by using a measure or tool (e.g., removal operation using forceps, etc.) which can damage the plant. Accordingly, even in the present invention, at the time of the transfer from the culturing to the cultivation, it is permissible to conduct the natural or spontaneous dropping of the gel-like support from the plant, and the dropping of the gel-like support by lightly moving the root of the plant, etc.

In general, a plant is exposed to a temperature change in a night-and-day cycle of 24 hours, and a temperature change in a four-season cycle, not only in the open-air field cultivation but also in the facility cultivation. As described above, the demand of a plant for water, nutrients, a plant growth-regulating substance, etc., is increased when the temperature becomes higher, while such a demand of the plant is decreased when the temperature becomes lower. Accordingly, it is ideal that the watering, the supply of a fertilizer, the administration of a plant growth-regulating substance to a plant are conducted in response to the above-mentioned temperature change. However, not only in the open-air field cultivation but also in the facility cultivation, enormous costs are naturally required in order to conduct the watering, the supply of a fertilizer, and the administration of the plant growth-regulating substance to a plant in response to the above-mentioned temperature change.

On the contrary, the plant-cultivating support or soil-modifying agent according to the present invention can solve the above-mentioned problems on the basis of the function peculiar thereto as described below.

The plant-cultivating support or soil-modifying agent according to the present comprises a hydrogel-forming polymer wherein the equilibrium water absorption is decreased along with an increase in temperature in the temperature range of not lower than 0° C. and not higher than of 70° C., and the change in the equilibrium water absorption is reversible with respect to the temperature. Accordingly, in the above predetermined temperature range (temperature range of not lower than 0° C. and not higher than of 70° C.), as the temperature becomes higher, the volume of the hydrogel comprising such a polymer is decreased, and on the basis of the volume decrease, the hydrogel discharges the water, nutrients, and/or plant growth-regulating substance contained in the inside of the hydrogel to the outside of the hydrogel (or, into another carrier such as soil), thereby to cause these substances to be in a state wherein they are liable to be easily absorbed into the plant through the root thereof. On the other hand, when the temperature becomes lower and the demand of the plant for the water, nutrients, and growth-regulating substance is decreased, the hydrogel (or hydrogel-forming polymer) absorbs these substances which are present in the outside of the hydrogel or in another carrier (such as soil), into the hydrogel per se, and stores these substances them in the hydrogel. Accordingly, an excess amount of these substances are not present in the outside of the hydrogel (or in another carrier such as soil), thereby to effectively suppress the adverse effect on the plant based on the presence of an excess amount of these substances.

The effect of the application of the support for a plant and soil-modifying agent according to the present invention may be exhibited more suitably under an environment wherein the "water content stress" to a plant is strong (e.g., desert, ground surface after tearing-off operation, building surfaces, roof and inside of buildings, etc.).

The support according or soil-modifying agent according to the present invention is concerned with the growth of a plant per se, and therefore it is suitably applicable to the development of lawn, greening of an atrium (an open-air courtyard in the inside of a building), virescence of desert, virescence of slopes, virescence of rooftops, virescence of wall surfaces, etc. Even when the support or soil-modifying agent according to the present invention is sprayed on the slope or wall surface, etc., together with a seed, the water content in the neighborhood of the seed is suitably be controlled with respect to the temperature change in the above-described manner, whereby the germination thereof is promoted and the growth thereof after the germination is also promoted, and the virescence of the slope, etc., is conducted extremely smoothly. Further, even when only the support or soil-modifying agent (containing no seed) according to the present invention is sprayed on the wall or slope surface, etc., the ecesis or establishment of seeds which spontaneously fall onto the wall surface, etc., the germination thereof, or the growth thereof after the germination is promoted, and the virescence of the wall surface, etc., is conducted smoothly.

Then, there is described the vessel or sheet according to the present invention.

As described above, most of the operations required for the germination or growth of a plant using a vessel in the tissue culturing or farm cultivation, are dependent on human labor. Particularly, the transferring operation of a plant conducted by manual operations not only requires a long period of time, but also it causes some damage to the plant.

More specifically, at the time of such a transfer operation, the thickly grown root of the plant presses the wall surface of the vessel so as to cause a friction therewith, and therefore a considerable period of time is required in order to take out the plant from the vessel, and the plant per se is damaged in many cases. In addition, when the plant is transferred to a vessel for receiving the plant after such a vessel is filled up with a solid plant-supporting carrier, the root of the plant does not enter the inside of the carrier well, and therefore the productivity or workability in the transfer operation is decreased, and the root per se is also damaged in many cases. Further, at the time at which a plant having an elongated root is intended to be transferred, even when the plant is implanted into the vessel after the plant is covered with a carrier for retention thereof (e.g., peat-moss) in advance, the transfer operation still requires a considerable period of time. Further, even when the plant is first put into the vessel and thereafter a granule-like plant-supporting carrier is charged into the vessel, the initial growth of the plant is poor in many cases. According to the present inventors' knowledge, it is presumably considered that such poorness in the initial growth is attributed to a small contact area between the root of the plant and the plant-supporting carrier.

On the contrary, when the plant-growing vessel or sheet according to the present invention is used, the above-mentioned problem encountered in the prior art may be solved on the basis of the function peculiar to the vessel or sheet according to the present invention as described hereinbelow.

More specifically, a polymer capable of providing a hydrogel having a crosslinked structure is disposed on the inner wall of the plant-growing vessel according to the present invention (or on the side of the sheet according to the present invention, on which a plant is to be disposed, when such a sheet is disposed on the inner wall of another vessel) by coating, etc. Accordingly, when the plant is put into the vessel and then the vessel is filled with water or a liquid culture medium, the above-mentioned hydrogel-forming polymer absorbs water so that the volume thereof is increased remarkably, and occupies the inner space of the vessel, whereby the polymer functions as at least a part of the support for the plant (in other words, the hydrogel-forming polymer functions as such a support, or promotes the supporting function for the plant).

In the present invention, on the basis of the function peculiar to the above-mentioned "polymer capable of providing a hydrogel having a crosslinked structure", the problems encountered in the prior art are solved. More specifically, such problems to be solved may include: one such that when a plant is transferred into a vessel after the vessel is filled with a solid plant-supporting carrier in advance, the root of the plant does not enter the inside of the carrier well, and therefore the resultant workability is decreased, and the root per se is also damaged; one such that when a plant is put into a vessel and then the conventional solid plant-supporting carrier is charged into the vessel, the resultant initial growth is decreased due to a small contact area between the root of the plant and the carrier; etc.

In addition, in an embodiment of the present invention wherein the hydrogel-forming polymer to be disposed on the inner wall of the vessel by coating comprises a hydrogel-forming polymer wherein the equilibrium water absorption is decreased along with an increase in temperature in the temperature range of not lower than 0° C. and not higher than 70° C., and the change in the equilibrium water absorption is reversible with respect to temperature, for example, it is possible that a plant is put into such a vessel, water or a liquid culture medium is poured into the vessel so that the polymer is caused to absorb water, whereby the polymer is swollen so as to occupy the inner space of the vessel and the plant is grown by using the polymer as (at least a part of) the support of the plant. After the plant is grown, when the temperature of the support is elevated, the hydrogel-forming polymer is de-swelled (or shrunk) so as to markedly decrease its volume, and therefore the grown plant may easily be removed from the vessel.

Accordingly, the present invention solves the above-mentioned problem encountered in the prior art, i.e., one such that since the thickly grown root presses the wall surface of the vessel, a considerable period of time is required in order to take out the plant from the vessel, and such an operation damages the root.

Another serious problem in the conventional plant-growing vessel is, as described above, that the environment in the rhizosphere is not suitable for the growth of the plant. Particularly, in close relation with the material of the vessel, the neighborhood of the inner wall of the vessel has a tendency such that the water content in this region is liable to be excessive or deficient, and further the difference in temperature (hot or cold) is large due to the influence of external air temperature. In general, the density of the growing root is particularly high in the neighborhood of the vessel wall, and such an adverse environment in the rhizosphere is liable to adversely affect the growth of the plant remarkably. Further, the bottom portion of the vessel is particularly liable to assume a water-excessive state due to watering, and on the contrary, the upper portion of the vessel is liable to assume a water-deficient state. Both of these water-excessive and water-deficient states adversely affect the growth of the plant.

On the contrary, the plant-growing vessel or sheet according to the present invention having the above-mentioned structure can solve the above-mentioned problems on the basis of the function peculiar to such a vessel or sheet, as described hereinbelow.

A polymer capable of providing a hydrogel having a crosslinked structure is disposed on the sheet or inner wall of the vessel according to the present invention by coating, etc. When the support (such as soil) in the neighborhood of the inner wall of the vessel assumes a water-excessive state for the above-mentioned reason, the polymer absorbs water so as to assume a hydrogel state. On the other hand, when the support in the neighborhood of the inner wall of the vessel assumes a water-deficient state, the hydrogel particles have a function of transferring water therefrom into the support. As a result, the environment for water in the rhizosphere in the neighborhood of the inner wall of the vessel is maintained almost constant, and the problems encountered in the prior art are solved.

Particularly, in an embodiment of the present invention wherein the above hydrogel-forming polymer comprises a hydrogel-forming polymer wherein the equilibrium water absorption is decreased along with an increase in temperature in the temperature range of not lower than 0° C. and not higher than 70° C., and the change in the equilibrium water absorption is reversible with respect to temperature, the polymer absorbs water from the support when the temperature becomes lower, while the polymer discharges water into the support when the temperature becomes higher. In other words, the water content in the support in the neighborhood of the sheet or the wall of the vessel is increased as the temperature becomes higher. In general, it is considered that a plant demands a smaller amount of water when the temperature is low (below about 5–20° C.), and demands a larger amount of water as the temperature becomes higher (not lower than about 20–35° C.). It is also considered that the excessive water content at a lower temperature invites a root decay phenomenon, and the deficient water content at a higher temperature invites insufficient growth. Accordingly, when the above-mentioned vessel or sheet having a hydrogel-forming polymer disposed therein is used, the environment in the rhizosphere is maintained more suitably, thereby to promote the growth of the plant more effectively.

In addition, the hydrogel-forming polymer disposed on the inner wall of the plant-growing vessel (or on the sheet to be disposed on the inner wall of the vessel) has a function of storing water content and/or nutrients in the crosslinked structure of the polymer as described above. Therefore, the storing function which has been performed by the "space" in the conventional growing vessel, may be performed by the above polymer extremely effectively in place of the above space. Therefore, according to the present invention (even when the ability of the growing vessel for storing water content and nutrients is retained constant), the internal volume of the vessel can be reduced remarkably.

As described above, according to the present invention, the volume of a vessel which has been considered to be "appropriate" in the prior art can be reduced remarkably, and further the originating power of the root can be improved due to an increase in the opportunity for the mechanical contact stimulus. Further, on the basis of the reduction in the internal volume of the vessel per se, it is also possible to reduce the area to be used for growing a plant, to reduce the amount of the material for the growing vessel, and to reduce the transporting costs. In addition, in combination with the above-mentioned labor saving in the water control, remarkable cost reduction can be accomplished.

Further, since the conventional vessel for home use has a lower portion of an open-system, and an excess of water is discharged from the open-system lower portion at the time of the watering, etc., a "receiving pan" must be used simultaneously therewith. The use of such a pan is troublesome and it is liable to impair the beautiful appearance thereof.

On the contrary, in the plant-growing vessel according to the present invention, since the water-storing ability is imparted to the wall surface of the vessel, it is not necessarily required to provide an opening portion at a lower part of the vessel. In other words, the opening portion of the vessel is omissible in the present invention. When the vessel having a closed-type lower portion is used, the problems encountered in the conventional vessel for home use (having an open-system lower portion) are easily solved.

In the above, the growth of a plant after the germination thereof has mainly been described, but the vessel or sheet according to the present invention is also suitably applicable to the germination of a seed or the growth thereof after the germination.

BEST MODE FOR CARRYING OUT THE INVENTION

Figure 1:
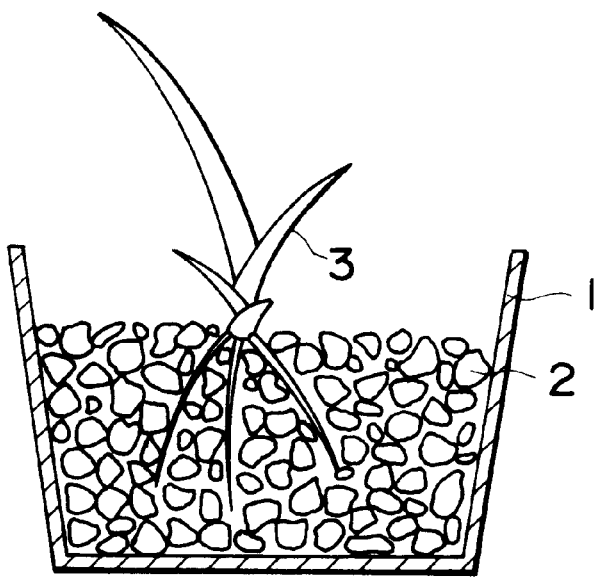
FIG. 1 is a schematic sectional view showing an embodiment of the method of using the plant-cultivating support according to the present invention.

Hereinbelow, the present invention will be described in detail with reference to the accompanying drawings as desired.

(Ventilating property)

In the present invention, the ventilating (or aerating) property of a plant-growing system may preferably be evaluated by using the "water evaporation rate" from the growing system. In the present specification, the plant-growing system having a "water evaporation rate" of 3% or less (preferably 2% or less, particularly 1% or less) per 24 hours, which is measured by the following method, is referred to as "ventilation-restricted condition (or culturing system)". This "ventilation-restricted condition" includes both of a so-called closed system and a semi-closed system.

On the other hand, the plant-growing system having a "water evaporation rate" of above 3% (preferably 5% or more, particularly 10% or more) per 24 hours is referred to as "ventilation non-restricted condition (or open-system)".

<Method of measuring water evaporation rate>

The solid component constituting a plant-growing system (e.g., the plant box and dry polymer in the system of Example 3 appearing hereinafter, weight: $W_1$ (g)) measured by means of a precise balance (e.g., an electronic balance mfd. by Shimazu Seisakusho K. K., trade name: LIBROR-EB-3200D). Then, a liquid component (the Hyponex liquid culture medium in the system of Example 3) is added to the above solid component and the resultant total weight ($W_2$) is measured by the same precise balance. The precise weight of the above liquid component (X) is calculated as ($X=W_2-W_1$). After the plant is transferred into the above-mentioned growing system, the resultant total weight (Y) of the whole growing system inclusive of the plant, the solid component and the liquid component is measured by means of the same precise balance.

After the above total weight (Y) is measured, there is measured the total weight (Z) of the whole growth system, of which ventilating property is to be evaluated, after it is left standing for a predetermined period of time under an environment of temperature of 25° C. and humidity of 30% (e.g., water evaporation rate Zd after one day (24 hours), water evaporation rate Zw after one week (7 days), and/or water evaporation rate Zm after one month (30 days)). BY use of the thus obtained weight Z, the water evaporation rate is determined by using the following calculation formula.

Water evaporation rate (%/24 hour)=100×(Y−Zd)/X,

Water evaporation rate (%/24 hour)=100×(Y−Zw)/(X×7), or

Water evaporation rate (%/24 hour)=100×(Y−Zm)/(X×30).

(Hydrogel-forming polymer)

The "hydrogel-forming polymer" to be disposed in the inside of the vessel according to the present invention refers to a polymer having a crosslinking or network structure, and has a property such that it retains water in the inside thereof on the basis of such a structure so as to form a hydrogel. Further, the "hydrogel" refers to a gel which at least comprise a crosslinked or network structure comprising a polymer, and water (as a dispersion liquid) retained by such a structure.

The "dispersion liquid" retained in the crosslinked or network structure is not particularly limited, as long as it is a liquid comprising water as a main component. More specifically, the dispersion liquid may for example be either of water per se, an aqueous solution and/or water-containing liquid (e.g., a mixture liquid of water and a monohydric or polyhydric alcohol).

In the present invention, it is preferred to use a product obtained by crosslinking a water-soluble or hydrophilic polymer compound, as the above-mentioned hydrogel-forming polymer. Such a crosslinked polymer has a property such that it absorbs water in an aqueous solution to be swollen, but is not dissolved therein. The equilibrium water absorption appearing hereinafter may be changed by changing the kind of the above-mentioned water-soluble or hydrophilic polymer and/or the degree of crosslinking thereof.

(Water-soluble or hydrophilic polymer compound)

Specific examples of the water-soluble or hydrophilic polymer constituting the support according to the present invention may include: methyl cellulose, dextran, polyethyleneoxide, polypropyleneoxide, polyvinyl alcohol, poly N-vinyl pyrrolidone, polyvinyl pyridine, polyacrylamide, poly-N-methyl acrylamide, polyhydroxymethyl acrylate, polyacrylic acid, polymethacrylic acid, polyvinylsulfonic acid, polystyrenesulfonic acid and their salts, poly-N,N-dimethylaminoethyl methacrylate, poly-N,N-diethylaminoethyl methacrylate, poly-N,N-dimethylaminopropyl acrylamide, and their salts, etc.

In the present invention, as the polymer constituting the above-mentioned hydrogel-forming polymer, it is particularly preferred to use a product obtained by chemically crosslinking a polymer compound having a negative solubility-temperature coefficient with respect to water, and/or a polymer compound having an LCST (Lower Critical Solution Temperature). Herein, the LCST refers to a temperature at which a polymer is finally converted into a non-soluble state so as to be precipitated, in the course wherein the polymer is changed from its water-soluble state into its hydrophobic state due to an increase in temperature. Such a phenomenon of changing between the water-soluble state and the hydrophobic state is reversible with respect to temperature (Haskins,M., et al., J. Macromol. Sci. Chem. A2(8); 1441, 1968).

Poly-N-isopropyl acrylamide (PNIPAAm) can be exemplified as a typical example of the above "polymer compound having an LCST". At a lower temperature, there is formed a hydrate (oxonium hydroxide) depending on the hydrogen bonding between the PNIPAAm molecule and the water molecule, whereby the PNIPAAm molecules show a water-solubility. On the other hand, at a higher temperature region, the hydrogen bonding between the PNIPAAm molecule and the water molecule is weakened so that it shows a tendency of decomposing the above hydrate and of being dehydrated, whereby the PNIPAAm molecules are converted into a hydrophobic state.

When a crosslinked structure is imparted to the above polymer having an LCST, the resultant polymer is not dissolved but retains a swollen gel state even in an aqueous solution at a temperature lower than the LCST. When the temperature is raised in such a swollen state, the polymer is converted into a hydrophobic state, whereby water is separated from the crosslinked material (hydrogel) in the swollen state.

As described above, the equilibrium water absorption of the above-mentioned hydrogel is remarkably decreased along with an increase in temperature, and the temperature-dependent change in the equilibrium water absorption is reversible. Accordingly, in the present invention, such a hydrogel is used so that it is disposed in a vessel, the water contained in the hydrogel (in some cases, a nutrient and/or plant growth-regulating substance which is in the state of being dissolved in such water) is pushed out from the inside of the hydrogel to the outside of the hydrogel along with an increase in temperature. On the other hand, when the temperature is decreased, water is again absorbed from the outside of the hydrogel (or from the inside of another carrier such as porous material and soil) into the hydrogel.

The LCST of the hydrogel-forming polymer constituting the vessel according to the present invention, may preferably be not lower than 0° C. and not higher than 70° C. (more preferably, not lower than 10° C. and not higher than 50° C.). When the LCST is lower than 0° C., the water-retaining property of the hydrogel-forming polymer is liable to be decreased in a lower temperature environment (e.g., in an environment of temperature of 10° C. or less). On the other hand, when the LCST exceeds 70° C., the water-discharging property of the hydrogel-forming polymer is liable to be decreased in an higher temperature environment (e.g., in an environment of a temperature 30° C. or more).

(Equilibrium water absorption)

<Method of measuring equilibrium water absorption $E_a$>

A hydrogel-forming is immersed in a large excess of water (ion exchange water) at a predetermined temperature for at least 3 days, until the polymer sufficiently absorbs water and the swelling of the polymer reaches an equilibrium. Thereafter, the weight (W) of the resultant hydrogel (i.e., "polymer+water") is measured. With respect to this "equilibrium of swelling", e.g., a paper of T. Tanaka, et al., Phys. Rev. Lett., 5, 2455 (1985) may be referred to.

Then, the above hydrogel is dried by vacuum drying at 100° C. for at least three days, and thereafter the weight (P) of the resultant dry hydrogel (that is, polymer) is measured. On the basis of the thus measured two weight values (W and P), the equilibrium water absorption Ea is defined by the following formula.

Equilibrium water absorption (Ea)={(W−P)/P}×100 (%).

(Temperature dependency and salt concentration dependency of equilibrium water absorption $E_a$)

In the hydrogel-forming polymer to be used in the present invention, in view of the water-retaining property of the hydrogel-forming polymer at a lower temperature environment, the equilibrium water absorption ($E_L$) at a low temperature (5° C.) may preferably be about 1,000% or more, more preferably about 3,000% or more, particularly about 5,000% or more (e.g., about 5,000–100,000%). On the other hand, in view of the water-discharging property of the polymer at a high temperature environment, the equilibrium water absorption ($E_H$) at a high temperature (50° C.) may preferably be about 6,000% or less, more preferably about 3,000% or less, particularly about 1,000% or less (e.g., about 1,000–500%).

In view of the balance between the above-mentioned water-retaining property and water-absorbing property of the above-mentioned polymer, the ratio ($E_L/E_H$) of these equilibrium water absorption values at a high temperature and a low temperature may preferably be about 2 or more, more preferably about 5 or more, particularly about 10 or more (e.g., about 10–200).

In the present invention, the hydrogel-forming polymer has a smaller salt concentration-dependency of equilibrium water absorption as compared with an usual highly water-absorbing polymer (e.g., crosslinked sodium acrylate-type polymer). More specifically, in the hydrogel-forming polymer to be used for the present invention, when an equilibrium water absorption $E_a$ of the polymer at 15° C. at an NaCl concentration of 0% (ion-exchange water) is denoted by "$E_N$", and an equilibrium water absorption Ea of the polymer at 15° C. at an NaCl concentration of 3 wt. % is denoted by "$E_S$", the ratio of these equilibrium water absorption values ($E_N/E_S$) may preferably be 20 or less, more preferably 10 or less (particularly 5 or less).

(Polymer having LCST)

Preferred examples of the polymer having an LCST to be used in the present invention may include: e.g., poly N-substituted acrylamide derivative, poly N-substituted methacrylamide derivative, and these copolymers of poly N-substituted acrylamide derivative/poly N-substituted methacrylamide derivative; polyvinyl methyl ether, polypropylene oxide, polyethylene oxide, etherified methyl cellulose., partially acetylated polyvinyl alcohol, etc. These polymers may also be used in various type of copolymers and/or mixtures, as desired. Among these, particularly preferred examples thereof to be used in the present invention may include: poly N-substituted acrylamide derivative or poly N-substituted methacrylamide derivative or these copolymers of poly N-substituted acrylamide derivative/ poly N-substituted methacrylamide derivative.

Preferred examples of the polymer to be used in the present invention are exemplified below in a sequence of from one having a lower LCST to one having a higher LCST:

poly-N-acryloyl piperidine;

poly-N-n-propyl methacrylamide;

poly-N-isopropyl acrylamide;

poly-N,N-diethyl acrylamide;

poly-N-isopropyl methacrylamide;

poly-N-cyclopropyl acrylamide;

poly-N-acryloyl pyrrolidine;

poly-N,N-ethyl methyl acrylamide;

poly-N-cyclopropyl methacrylamide;

poly-N-ethyl acrylamide

The above polymer may be either a homopolymer or a copolymer comprising a monomer constituting the above polymer and "another monomer". The "another monomer" to be used for such a purpose may be either a hydrophilic monomer, or a hydrophobic monomer.

Specific examples of the above hydrophilic monomer may include: N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinylsulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. However, the hydrophilic monomer to be usable in the present invention is not restricted to these specific examples.

On the other hand, specific examples of the above hydrophobic monomer may include: acrylate derivatives and methacrylate derivatives such as ethyl acrylate, methyl methacrylate, butyl methacrylate, and glycidyl methacrylate; N-substituted alkyl methacrylamide derivatives such as N-n-butyl methacrylamide; vinyl chloride, acrylonitrile, styrene, vinyl acetate, etc. However, the hydrophobic monomer to be usable in the present invention is not restricted to these specific examples.

In general, when the above polymer compound is copolymerized with a hydrophilic monomer, the resultant LCST may be increased. On the other hand, when the above polymer is copolymerized with a hydrophobic monomer, the resultant LCST may be decreased.

The above LCST may be regarded as one of the factors for determining the temperature dependency of the equilibrium water absorption of the hydrogel-forming polymer according to the present invention. That is, the LCST or the temperature dependency of the equilibrium water absorption of the hydrogel may also be controlled by selecting the component to be used for such copolymerization.

(Crosslinking)

As the method of imparting a crosslinked structure to a polymer, there are a method wherein a crosslinked structure is introduced into the polymer at the time of the polymerization of the monomer for providing the polymer; and a method wherein a crosslinked structure is introduced to a polymer after the completion of the polymerization of the monomer. Each of these methods can be used in the present invention.

The former method (i.e., introduction of crosslinking at the time of monomer polymerization) can generally be conducted by utilizing the copolymerization with a bifunctional monomer (or a monomer having three or more functional groups). For example, such a method may be conducted by using a bifunctional monomer such as N,N-methylene bis-acrylamide, hydroxyethyl dimethacrylate, and divinylbenzene.

The latter method (i.e., introduction of crosslinking after monomer polymerization) can generally be conducted by forming a crosslink between molecules by utilizing light, electron beam, γ-ray irradiation, etc.

Further, the latter method may also be conducted by crosslinking a polymer, e.g., by using, as a crosslinking agent, a multi-functional molecule having a plurality of functional groups (such as isocyanate group) which is capable of being bonded to a functional group (such as amino group) in the polymer.

In the present invention, the above-mentioned "equilibrium water absorption" (particularly, equilibrium water absorption at a lower temperature range below the LCST) of the hydrogel-forming is dependent on the above-mentioned crosslinked structure, particularly the density of crosslinking of the polymer. In general, as the crosslinking density becomes lower, the equilibrium water absorption tends to be increased. The degree of the effect of the crosslinking density on the equilibrium water absorption at a higher temperature range above the LCST is relatively small, and therefore the temperature dependency of the equilibrium water absorption tends to be increased as the crosslinking density becomes lower.

In the former method, the crosslinking density can arbitrarily be controlled, e.g., by changing the copolymerization ratio of the bifunctional monomer. In the latter method, the crosslinking density can arbitrarily be controlled, e.g., by changing the quantity of irradiation such as light, electron beam, and γ-ray.

In the present invention, the crosslinking density may preferably be in the range of about 0.02 mol % to 10 mol %, more preferably about 0.05 mol % to 4 mol %, in terms of the ratio of the moles of the branching point to the moles of all the monomer. Alternatively, when the crosslinked structure is introduced by the former method (introduction of crosslinking at the time of polymerization), the crosslinking density may preferably be in the range of about 0.03 wt. % to 3 wt. %, more preferably about 0.05 wt. % to 1.5 wt. %, in terms of the copolymerization weight ratio of the bifunctional monomer to all the monomers (inclusive of the bifunctional monomer per se).

When the crosslinking density exceeds about 10 mol %, the temperature dependency of the equilibrium water absorption of the hydrogel-forming polymer according to the present invention is decreased, whereby the effect of the hydrogel-forming polymer of water absorption-water discharge is decreased. On the other hand, when the crosslinking density is below about 0.02 mol %, the hydrogel-forming polymer becomes mechanically weak, and the handling thereof becomes difficult, and the possibility of mechanical breakage is increased in the course of the swelling and shrinkage thereof along with a temperature change.

The crosslinking density (molar ratio of the branching points with respect to all the monomer) may be determined quantitatively, e.g., by $^{13}$C-NMR (nuclear magnetic resonance absorption) measurement, IR (infrared absorption spectrum) measurement, or elemental analysis.

(Shape of hydrogel or polymer)

The shape or form of the hydrogel or hydrogel-forming polymer to be disposed in the inside of the vessel according to the present invention is not particularly limited, but may appropriately be selected depending on the kind of a plant, growth method therefor, etc. Specific examples of the shape of the hydrogel or polymer may include various shapes such as layer-like shape, micro-bead-like shape, fiber-like shape, film-like shape, and indeterminate shape.

The dimension or size of the hydrogel or polymer in the present invention may appropriately be selected depending on the kind of the plant, cultivation method therefor, etc. In order to enhance the follower property (or following property) of the change process in the equilibrium water absorption (i.e., the swelling and shrinkage process) of the hydrogel-forming polymer with respect to a temperature change, it is preferred to increase the surface area of the hydrogel or polymer per unit volume thereof, that is, to decrease the dimension of one object (e.g., one particle) of the hydrogel or polymer. For example, the dimension or size of the hydrogel or polymer in the present invention may generally be in the range of about 0.1 μm to 1 cm, more preferably in the range of about 1 μm to 5 mm (particularly about 10 μm to 1 mm), in a dried state thereof.

In the hydrogel or polymer according to the present invention, the above-mentioned "dimension in a dried state" refers to the average of maximum diameters (maximum dimensions) of the hydrogel or polymer (average of values obtained by measuring at least 10 objects). More specifically, for example, the following dimension may be treated as the "dimension in a dried state" in accordance with the shape of the above hydrogel or polymer.

Micro-bead shape: particle size (average particle size);

Fiber shape: average of lengths of respective fiber-like pieces;

Film shape, indeterminate shape: average of maximum dimensions of respective pieces; and Layer shape: thickness of a polymer layer.

In the present invention, in place of the above "average of maximum values", it is also possible to use the diameter of a "ball" having a volume equal to the average of the volumes of respective pieces (average of values obtained by measuring at least 10 pieces) as the "dimension in a dried state" of the particles of the above hydrogel or polymer.

(Shaping method)

The method of shaping of the hydrogel or polymer according to the present invention is not particularly limited. AS such a method, it is possible to use an ordinary method of shaping a polymer depending on the desired shape of the hydrogel or polymer.

When the simplest method is used, a monomer for providing the water-soluble or hydrophilic polymer, the above-mentioned multi-functional monomer (such as bifunctional monomer), and a polymerization initiator are dissolved in water, and the monomer, etc., is polymerized by use of heat or light, whereby a hydrogel or polymer can be prepared. The resultant hydrogel or polymer is mechanically crushed or pulverized, the unreacted monomer, the remaining polymerization initiator, etc., are removed therefrom by washing with water, and thereafter the resultant product is dried, thereby to provide a hydrogel-forming polymer for constituting the vessel or sheet according to the present invention.

Further, when the monomer for providing the water-soluble or hydrophilic polymer is liquid, the multi-functional monomer and polymerization initiator are added into the monomer, the monomer is polymerized by bulk polymerization by use of heat or light, the resultant product is mechanically crushed, the unreacted monomer and the remaining multi-functional monomer are removed therefrom by extraction with water, etc., and the product is dried, whereby a hydrogel or polymer according to the present invention can be provided.

On the other hand, when the hydrogel or polymer according to the present invention in a micro-bead shape is intended to be prepared, it is possible to use an emulsion polymerization method, a suspension polymerization method, a precipitation polymerization method, etc. In view of the control of the resultant particle size, a reverse-phase suspension polymerization method may particularly preferably be used. In the reverse-phase suspension polymerization method, as a dispersion medium, an organic solvent which does not dissolve the monomer and the resultant polymer is preferred. For example, a saturated hydrocarbon such as hexane is preferred as the above dispersion medium. In addition, it is also possible to use a surfactant (e.g., a nonionic surfactant such as sorbitan fatty acid ester) as a suspension auxiliary in combination with the above organic solvent.

The particle size of the resultant micro-bead can be controlled by the kind or amount of the surfactant to be added, the stirring speed, etc. As the polymerization initiator, either of a water-soluble polymerization initiator, and a water-insoluble polymerization initiator can be used.

When the hydrogel or polymer according to the present invention is formed into a fiber shape, film shape, etc., for example, it is possible to use a method wherein an aqueous solution of a water-soluble polymer is extruded into an organic solvent which is unmixable with water by using a die, etc., to form each of the predetermined shapes, and then the resultant product is irradiated with light, electron beam, γ-ray, etc., so as to impart a crosslinked structure to the polymer. Further, it is also possible to use a method wherein the above water-soluble polymer is dissolved in an organic solvent or water, is shaped by a solvent casting method, and then is irradiated with light, electron beam, γ-ray, etc., so as to impart a crosslinked structure to the polymer.

(Additives)

In the crosslinked structure of the hydrogel-forming polymer constituting the plant-cultivating support, soil-modifying agent, vessel or sheet according to the present invention, at least water is retained as desired so as to form a hydrogel. However, it is also possible to add another additive to the hydrogel as desired. As the additive to be incorporated into the inside of the hydrogel or polymer for such a purpose, it is possible to use known additives which can ordinarily be used in the usual plant cultivation in open-air field or facilities (such as greenhouse) without particular limitation.

Specific examples of such a known additive may include: various nutrients for a plant, agents participating in the cultivation of a plant other than the nutrients (such as plant growth-regulating substance, plant growth promoting substance, and plant-growth retardant) or agricultural chemicals (such as weed killer, insecticide, and bactericide).

(Nutrient)

Specific examples of the nutrient which can be introduced, as desired, into the inside of the hydrogel or polymer according to the present invention may include major elements such as N, P, K, Ca, Mg and S and/or minor elements such as Fe, Cu, Mn, Zn, Mo, B, Cl and Si.

When an inorganic nutrient or organic nutrient containing the above element is introduced into the inside of the hydrogel or polymer according to the present invention, the resultant hydrogel or polymer discharges to the outside thereof (e.g., into soil) a nutrient for which demand of the plant is increased along with an increase in temperature. On the other hand, the hydrogel or polymer stores in the inside thereof a nutrient for which demand of the plant is decreased at a lower temperature. As a result, persistence of the nutrient may be improved remarkably.

As the method of incorporating such a nutrient into the hydrogel or polymer, it is possible to use a method wherein an aqueous solution containing a substance such as urea, calcium nitrate, potassium nitrate, potassium hydrogen phosphate, magnesium sulfate, and ferrous sulfate is cooled to a temperature below the LCST, the above hydrogel or polymer per se in a dry state is immersed in the above-mentioned aqueous solution to be swollen, thereby to cause the resultant hydrogel or polymer to absorb thereinto the desired nutrient, etc.

(Plant-growing substance, etc.)

It is also possible to incorporate into the above hydrogel or polymer the above-mentioned plant growth-regulating substance, plant growth-promoting substance, plant-growth retardant, etc., or agricultural chemicals (such as weed killer, insecticide, and bactericide) as desired, which is a substance participating in the cultivation of the plant other than the above-mentioned nutrients.

In general, the crop cultivation under high-temperature over-humidity condition is liable to cause a phenomenon such as stem spindly growth, or branching or blooming defectiveness, so as to lower the value of the agricultural products. Further, the problem of such a value decrease can also occur in some cases, depending on the character of the race of the plant. In such a case, it is preferred to use a growth retardant having an effect of suppressing the extension of the stem, etc., so as to promote the branching and blooming, as desired. In the present invention, when the growth retardant is incorporated into the inside of the hydrogel or polymer, the plant-cultivating support, soil-modifying agent, vessel, or sheet comprising the resultant hydrogel or polymer as a constitution element thereof discharges therefrom the growth retardant to the outside (e.g., into soil) at a high temperature so as to suppress the stem elongation of the plant. On the other hand, at a lower temperature at which the demand for the growth retardant becomes low, the growth retardant is not discharged from the hydrogel or polymer, and therefore persistence of the effect of the growth retardant is improved remarkably.

In general, the necessity for the weed killer also becomes greater at a high temperature as compared with that at a low temperature. Accordingly, when the weed killer is incorporated into the hydrogel or polymer according to the present invention, the effect of the weed killer and the persistence thereof are remarkably improved on the basis of the same storage-discharge mechanism as described above.

(Method of incorporating additive)

As the method of incorporating one of the above various additives into the inside of the hydrogel or polymer, it is possible to use a method wherein the polymer is immersed in an aqueous solution of the additive at a temperature which is sufficiently lower than the LCST of the polymer so that the polymer is caused to absorb the above aqueous solution, thereby to prepare a hydrogel or polymer. Further, when a growth-regulating substance (such as growth retardant) such as inabenf ide and uniconazole which has a very low solubility in water is used, it is also possible to incorporate the growth-regulating substance into the inside of the hydrogel or polymer by using an organic solvent which is capable of dissolving the growth-regulating substance and is capable of swelling the hydrogel or polymer, whereby the growth-regulating substance can be incorporated into the inside of the hydrogel or polymer in a practically usable concentration.

(Method of using plant-cultivating support)

The plant-cultivating support according to the present invention comprises the above-mentioned hydrogel or polymer, and in general, it can retain a moderate "hardness" or shape-retaining property based on the gel structure thereof in the temperature range (e.g., range of about 15–35° C.) which is generally used for the cultivation of the plant. More specifically, for example, as shown in the schematic sectional view of FIG. 1, it is possible to cultivate a plant 3 by using a plant-cultivating support 2 according to the present invention singly or alone, which has appropriately been disposed in the inside of a vessel 1, without using soil or another cultivating carrier in combination therewith.

(Method of using soil-modifying agent)

Figure 2:
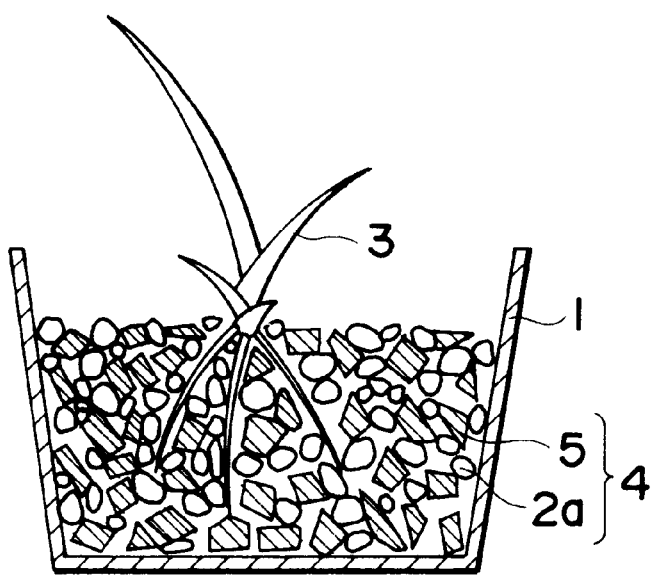
FIG. 2 is a schematic sectional view showing an embodiment of the method of using the soil-modifying agent according to the present invention.

On the other hand, in consideration of the easiness or cultivation cost in the cultivation of a plant, it is also possible to use the above hydrogel or polymer as a soil-modifying agent. In such a case, it is possible to appropriately add the soil-modifying agent according to the present invention to another plant-cultivating carrier. More specifically, for example, as shown in the schematic sectional view of FIG. 2, the soil-modifying agent 2a according to the present invention is substantially uniformly added into the inside of another plant-cultivating carrier 5 (such as soil) to prepare a support 4 for a plant, and the thus obtained support 4 for a plant is disposed in the inside of the vessel 1, whereby the plant 3 is cultivated.

The above "another plant-cultivating carrier" to be used in combination with the soil-modifying agent according to the present invention is not particularly limited. As such "another plant-cultivating carrier", it is preferred to use, e.g., soil or gravel, sand, pumice, carbide, peat, vermiculite, bark, pearlite, zeolite, rock wool, sponge, peat-moss, crushed coconut shell, crypto-moss, singly or as a mixture of two or kinds thereof as desired.

When a plant is cultivated by using the soil-modifying agent according to the present invention, it is preferred to mix the soil-modifying agent according to the present invention comprising a hydrogel or polymer in a mixing ratio of about 0.1–10 wt. % (more preferably about 0.3–3 wt. %) in terms of the weight percent in a dry state with respect to the above "another plant-cultivating carrier" such as soil.

Figure 3:
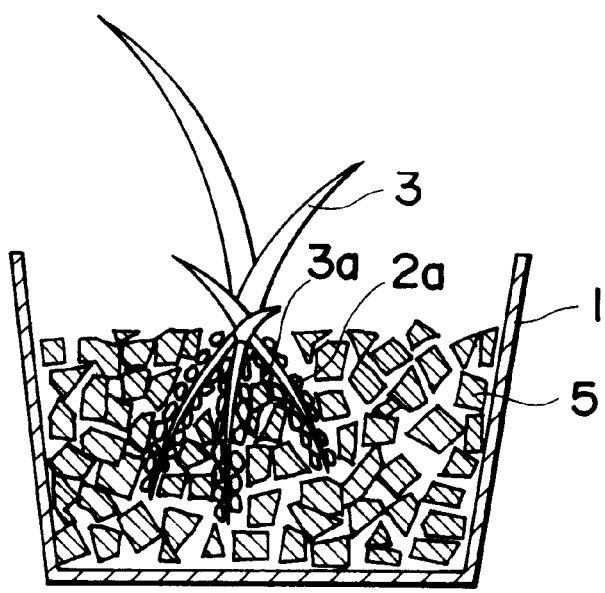
FIG. 3 is a schematic sectional view showing another embodiment of the method of using the soil-modifying agent according to the present invention.

Further, when the plant 3 is transferred to a usual plant-cultivating carrier such as soil, it is also possible that as shown in the schematic sectional view of FIG. 3, the soil-modifying agent 2a according to the present invention is physically attached to the root 3a of the plant 3, and then is buried or embedded in the above-mentioned plant-cultivating carrier 5 (such as soil) so as to bury the root 3a in the plant-cultivating carrier 5, thereby to cultivate the plant 3.

Figure 4:
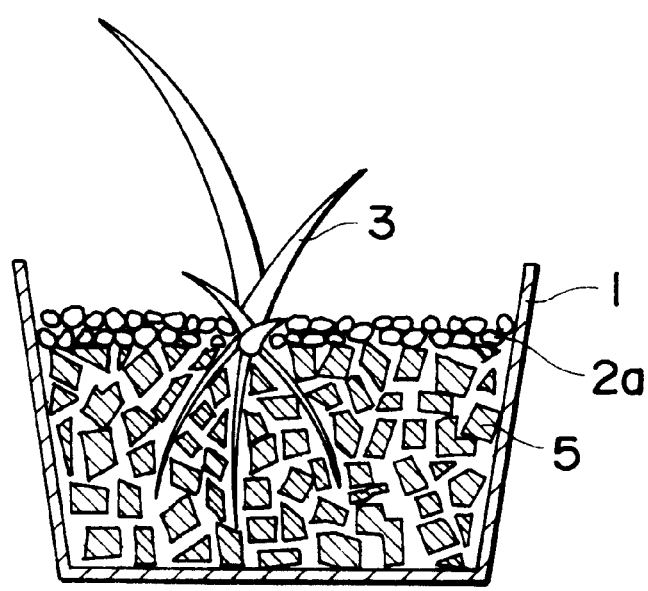
FIG. 4 is a schematic sectional view showing a further embodiment of the method of using the soil-modifying agent according to the present invention.

Further, as shown in the schematic sectional view of FIG. 4, it is also possible that a plant 3 is buried in a usual plant-cultivating carrier 5 (such as soil), and then the soil-modifying agent 2a according to the present invention is distributed thereinto or thereon.

(Plant)

The plant to which the plant-cultivating support or the soil-modifying agent according to the present invention is applicable is not particularly limited as long as it can be subjected to open-air field cultivation or facility cultivation (such as greenhouse), and may be either a plant (such as plantlet), or a part of the plant (such as stem). In view of the efficiency or yield in the open-air field cultivation or facility cultivation (such as greenhouse), it is preferred that a plant which has been grown in a culturing chamber (usually under a sterilized condition) to a certain extent, is subjected to the cultivation by using the plant-cultivating support or soil-modifying agent according to the present invention.

(Cultivation condition)

The plant-cultivating support or soil-modifying agent according to the present invention can be used under the "culturing" condition, but may be used under the "cultivation" condition rather preferably.

In the present specification, in the "culturing" of a plant, a part or entirety of the plant is usually grown, regenerated or subcultured in a glass vessel (in vitro) under a sterilized condition in many cases (with respect to an embodiment of such culturing, "Agricultural Encyclopedia" edited by Agricultural Encyclopedia Editing Committee, page 1024, (1991), Yokendo may be referred to). In many cases, this "culturing" is conducted in a culturing chamber wherein the plant growth condition is retained substantially constant (e.g., 25° C., illuminance 3000 lux, 16h-fluorescent light illumination).

On the other hand, in the "cultivation" of a plant, in many cases, a part or entirety of the plant is generally grown under a non-sterilized condition. In the "cultivation", the condition for the growth of the plant is changed by a change in the external environmental factor (such as temperature, humidity, quantity of solar radiation, light intensity).

Further, for the purpose of acclimation of a plant, etc., there is a case wherein the "culturing" condition is made closer to the "cultivation" condition (e.g., there is used a greenhouse having a temperature difference between night and day, or a culturing chamber, etc., which is set to 25° C. at daytime, and to 19° C. at night, with a temperature difference of 6° C.). Further, there is also a case wherein the "cultivation" condition is made closer to the "culturing" condition (e.g., vessel cultivation in a culturing chamber under a non-sterilized condition) for the purpose of controlling the "cultivation" condition for the plant in a preferred manner.

In the "cultivation" according to the present invention, the other conditions (such as vessel for accommodating a plant, and place or site for the cultivation) may arbitrarily be selected as long as the plant is grown under the non-sterilized condition. More specifically, for example, the shape of the cultivating vessel is not particularly limited, but a vessel having a known shape such as pot may appropriately be used. The material constituting the vessel is not particularly limited, but a known material such as paper, plastic, ceramic, and glass may appropriately be used. The site or place for cultivation is not particularly limited but an open-air place such as field or bare ground; and facility such as greenhouse, plant factory, and culturing chamber may appropriately be used.

As described above, the plant-cultivating support or soil-modifying agent according to the present invention may commonly be used under a sterilized condition and under a non-sterilized condition. Accordingly, when the plant-cultivating support or soil-modifying agent according to the present invention is used, the culturing and cultivation of the plant may be conducted by commonly using the cultivating support and the soil-modifying agent. In the operation or manipulation in the transfer from the culturing to cultivation, as desired, a part or entirety of the medium (component such as water, and/or another nutrient) to be retained or incorporated in the inside of the hydrogel or polymer may be exchanged by utilizing the above-mentioned temperature-responsive property of the hydrogel-forming polymer, while the hydrogel-forming polymer per se being attached to the plant. Accordingly, it is possible to effectively prevent the damage to the plant or a part thereof (such as root) at the time of the transfer of the plant.

(Shape and material of vessel/sheet)

The shape of the plant-growing vessel according to the present invention is not particularly limited as long as the above-mentioned "hydrogel-forming polymer having a crosslinked structure" is disposed inside thereof, but may be formed into one of known various shapes such as cotyle-type, pot-type, planter-type, tray-type, etc.

Figure 5:
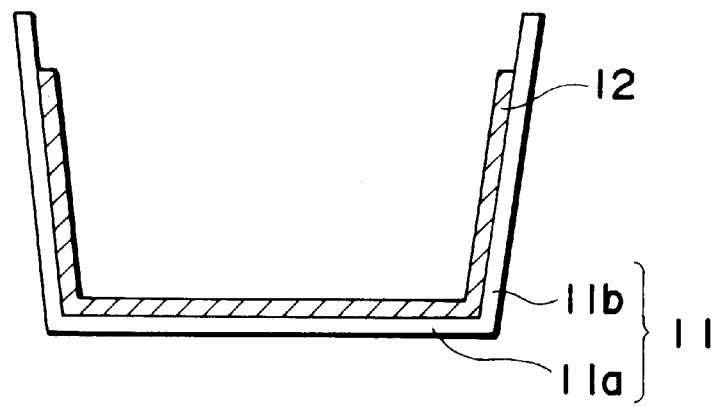
FIG. 5 is a schematic sectional view showing an embodiment of the plant-growing vessel according to the present invention.

The schematic sectional view of FIG. 5 shows an embodiment (pot-type) of the growing vessel according to the present invention. Referring to FIG. 5, a layer 12 comprising a "hydrogel-forming polymer having a crosslinked structure" is disposed in the inside of a pot-type vessel 11 having a bottom 11a and a sidewall portion 11b. Of course, it is possible that one or more openings (not shown) may be provided in the bottom 11a or side wall portion 11b as desired.

Similarly, the shape of the plant sheet according to the present invention is not particularly limited as long as the above-mentioned "hydrogel-forming polymer having a crosslinked structure" is disposed on the surface of at least a part thereof, but may be formed into one of known various kinds of shapes.

Figure 6:
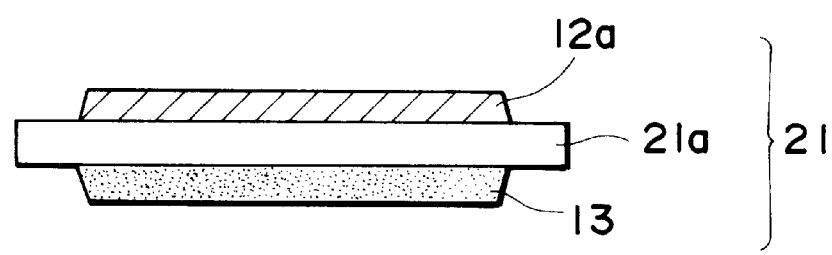
FIG. 6 is a schematic perspective view showing an embodiment of the plant-growing sheet according to the present invention.
Figure 7:
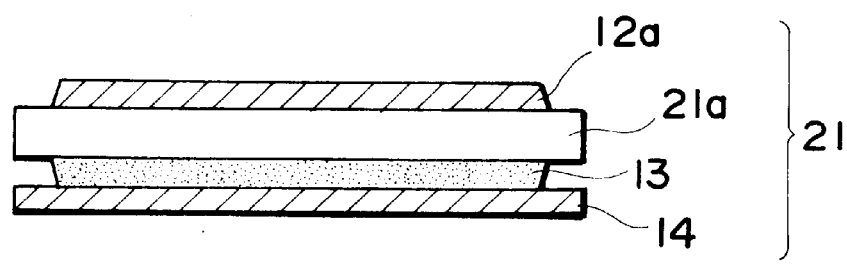
FIG. 7 is a schematic perspective view showing another embodiment of the plant-growing sheet according to the present invention.

The schematic sectional view of FIG. 6 shows an embodiment of the growing sheet according to the present invention. Referring to FIG. 6, a layer 12a comprising a "hydrogel-forming polymer having a crosslinked structure" is disposed on one of the surfaces of a sheet base material 21a. On the surface (back) of the sheet base material 21a disposed opposite to the face on which the polymer layer 12a is disposed, a layer 13 comprising a sticking agent or adhesive (comprising carboxymethyl cellulose (CMC), etc.) may be disposed as desired. Further, as shown in FIG. 7, a sheet 14 having a releasing property may be disposed on the sticking agent/adhesive layer 13 as desired. When the sheet 21 of such an embodiment as shown in FIG. 7 is used, the sheet 21 may easily be placed at a desired location of a conventional vessel (not shown) by tearing off the releasing sheet 14, and thereafter disposing the sheet 21 in the conventional vessel.

The sheet according to the present invention may be formed into a shape having a partition (inner dividing wall) as desired.

Figure 8A:
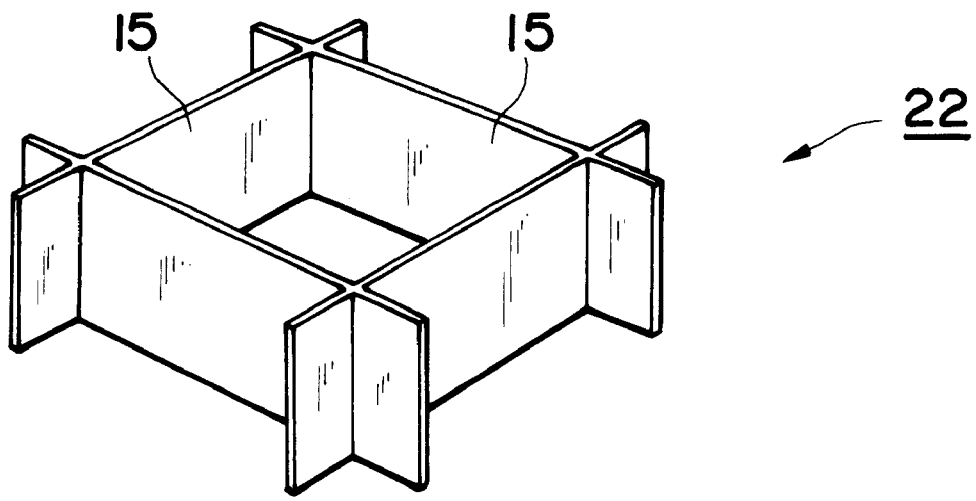
FIGS. 8A to 8B are schematic perspective views showing another embodiment of the plant-growing sheet (partition-type) according to the present invention.
Figure 8B:
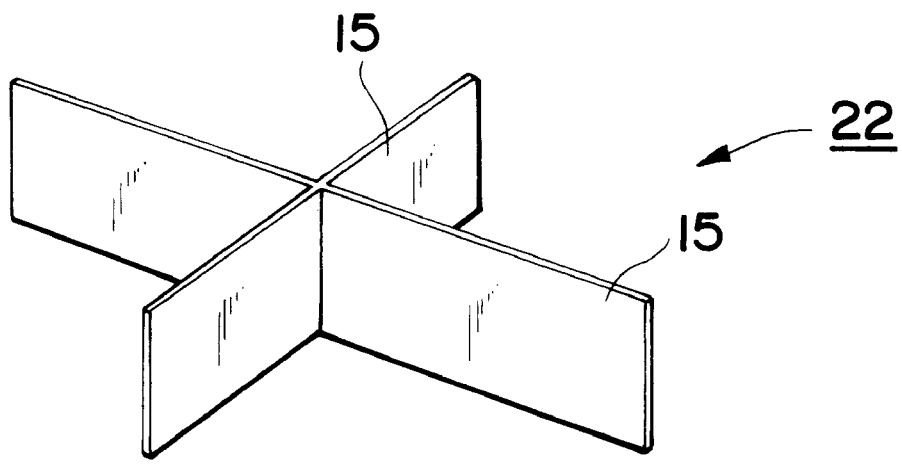

The schematic perspective views of FIG. 8A to FIG. 8B show an example of the embodiment of the sheet according to the present invention having a partition. FIG. 8A shows an example of the single cell-type partition form (with an extension portion), and FIG. 8B shows an example of the 4 (four) cell-type partition form. The number of "the cell" to be formed by these partitions is not particularly limited, but may preferably be about 1–10000 (more preferably about 10–1000) in view of efficient utilization or efficiency of the cultivating area. In these partition-type sheet 22 according to the present invention, the layer (not shown) comprising the "hydrogel-forming polymer having a crosslinked structure" is disposed on at least a part of the surface 15 of the partition on which a plant is to be disposed.

Figure 9:
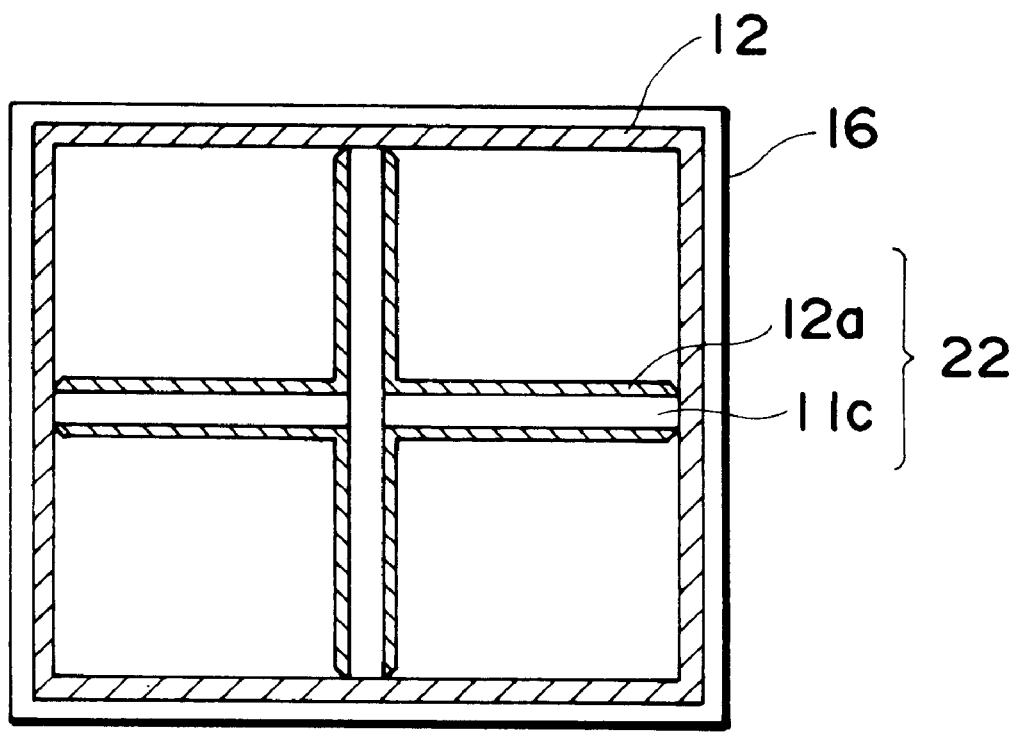
FIG. 9 is a schematic plan view showing a case wherein the partition-type sheet according to the embodiment of FIGS. 8A to 8B is used in combination with another vessel.

As shown in the schematic plan view of FIG. 9, when the partition-type sheet 22 according to the present invention is used in combination with "another vessel" 16 (conventional vessel is also usable), the removal of a plant at the time of the transfer thereof becomes very easy by utilizing the attachment and detachment between the sheet 22 and "another vessel" 16. In other words, when the grown plant (not shown) is intended to be removed from the vessel 6 or sheet 12, the removal of the plant becomes extremely easy by pulling out the partition 22 from the vessel 6 in advance. The above-mentioned "another vessel" 16 may also be a conventional vessel, or a plant-growing vessel (i.e., vessel according to the present invention) wherein a layer 12 of the "hydrogel-forming polymer" is disposed in the inside thereof as desired.

The material for the vessel or sheet according to the present invention is not particularly limited, but may appropriately be one of known materials such as ceramic or earthenware (unglazed pottery), metal, wood, plastic, and paper.

(Embodiment of polymer arrangement)

In the present invention, the location, area, shape (e.g., either of an intermittent layer or continuous layer), or measure of disposing the hydrogel-forming polymer is not particularly limited as long as the polymer is disposed in the inside of the growing vessel.

The location of the above-mentioned polymer disposed in the vessel may for example be either of the bottom face 11a or the side face 11b (FIG. 5) of the vessel, but the polymer may preferably be disposed on the side face 11b of the vessel in view of easiness in retaining the plant by the swelling of the polymer.

In the present invention, in order to effectively exhibit the function of the hydrogel-forming polymer, when the area of inner surface of the vessel (or the area of one of the side surfaces of a sheet) is denoted by $S_a$, and the area on which the hydrogel-forming polymer has been disposed is denoted by $S_p$, the ratio $(S_p/S_a) \times 100$ of these areas may preferably be about 10% or more, more preferably about 50% or more (particularly about 70% or more).

Figure 10A:
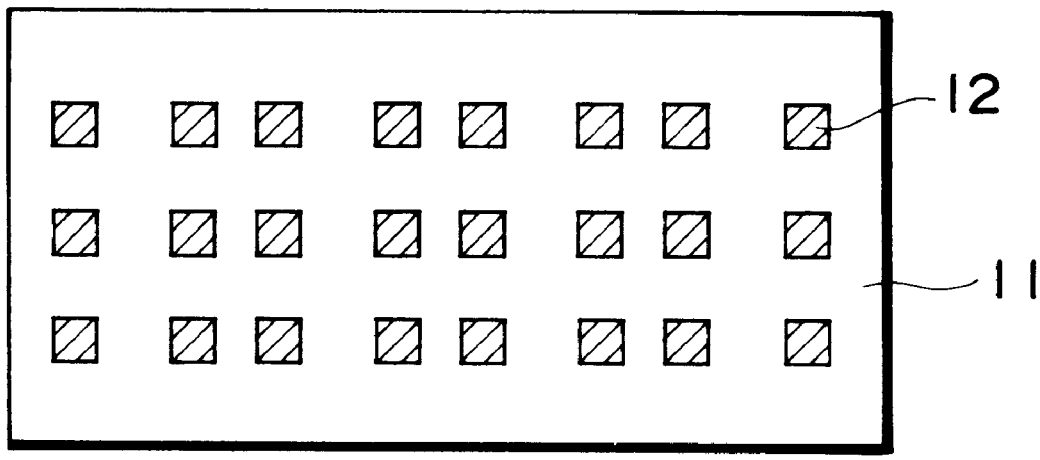
FIGS. 10A to 10B are schematic plan views showing an example of the embodiment wherein a hydrogel-forming polymer is disposed on the base material in the form of an intermittent layer.
Figure 10B:
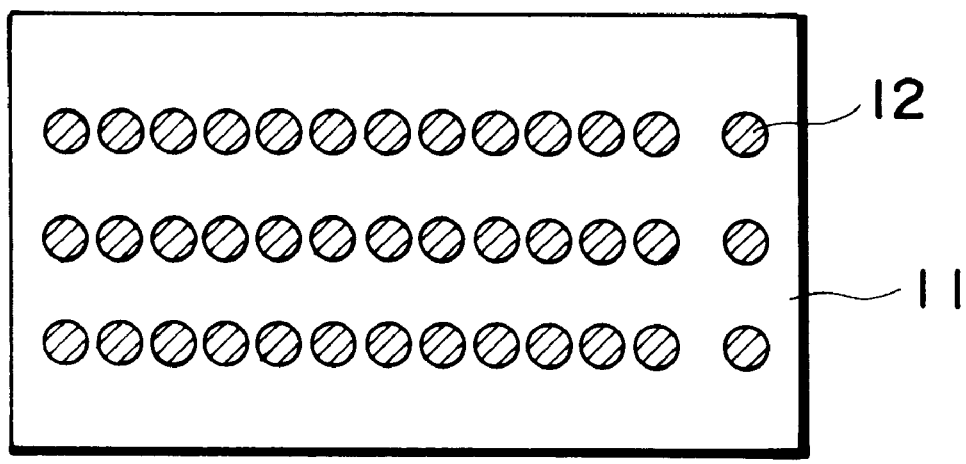

In the present invention, the layer 12 or 12a of the hydrogel-forming polymer may be a continuous layer or an intermittent layer. Such an intermittent layer may easily be formed by an arbitrary measure such as screen printing. When the intermittent layer is intended to be formed, the plan shape thereof can be an arbitrary shape such as checkered pattern-type as shown in FIG. 10 A, and spot-type as shown in FIG. 10B.

Figure 11A:
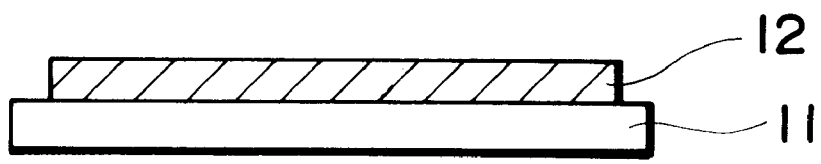
FIGS. 11A to 11C are schematic sectional views showing an example of the embodiment wherein a hydrogel-forming polymer is disposed on the base material of a vessel or sheet in the present invention.
Figure 11B:
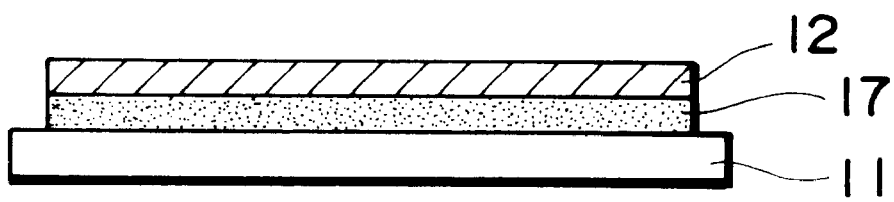
Figure 11C:
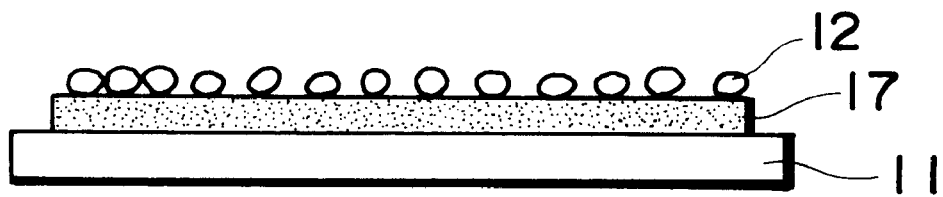

When the layer 12 or 12a of the hydrogel-forming polymer is disposed on the base material 11 of the vessel or sheet, the embodiment of the arrangement is not particularly limited. In view of easiness in the arrangement thereof, there may preferably be used any of an embodiment wherein the polymer layer 12 is disposed directly on the base material 11 (FIG. 11 A), an embodiment wherein the polymer layer 12 is disposed on a layer 17 of a sticking agent or adhesive which is disposed on the base material 11 (FIG. 11 B), or an embodiment wherein the polymer layer 12 in the shape of an arbitrary form such as particulate-type and indeterminate-type is disposed on a layer 17 of a sticking agent or adhesive which is disposed on the base material 1 (FIG. 11C). In the above-mentioned embodiment of FIG. 11 A, in order to impart an adhesive property to the polymer layer 12 with respect to the base material 11 or to enhance the adhesive property, it is possible that a hydrogel-forming polymer is mixed or dispersed in the sticking agent or adhesive, and then is formed into the above-mentioned polymer layer 12 as desired. In such a case, it is preferred to use the sticking agent or adhesive in an amount of about 0.01–10 wt. parts (more preferably, about 0.1–2 wt. parts) with respect to 10 wt. parts of the hydrogel-forming polymer.

As the above "sticking agent or adhesive", a known sticking agent or adhesive can be used without particular limitation, but it is preferred to use a substance which is substantially non-toxic or has a low toxicity to a plant to be cultivated, as the above-mentioned substance. Specific examples of such a sticking agent or adhesive, may include: rubber or latex-type (natural rubber-type, isoprene latex-type), acrylic resin-type (acrylic-type, cyano-acrylate-type), epoxy resin-type, urethane resin-type, protein-type (soybean protein-type, gluten-type), starch-type (starch-type, dextrin-type), cellulose-type (CMC-type, nitro-cellulose-type).

In any of the above-mentioned embodiments of the vessel or sheet, in order to effectively exhibit the function of the hydrogel-forming polymer, when the area of inner surface of the vessel (or the area of one of the side surfaces of a sheet) is denoted by $S_a$, and the weight of the disposed hydrogel-forming polymer is denoted by $M_p$, the amount of the application of the polymer ($M_p/S_a$) may preferably be about 0.0001 g/cm$^2$ (0.1 mg/cm$^2$) or more, more preferably about 0.001 g/cm$^2$ (1 mg/cm$^2$) to 0.2 g /cm$^2$ (particularly about 0.002 g/cm$^2$ (2 mg/cm$^2$) to 0.1 g /cm$^2$).

(Process for producing plant-growing vessel or sheet)

The process for producing a shaped product (vessel or sheet), the base material surface of which the hydrogel has been fixed is not particularly limited, but, for example, either of the following two processes may preferably be used.

The first process is one wherein the material to be used as the base material is shaped into a vessel or sheet such as pot and planter in advance, then a substance (such as sticking agent and adhesive) having a function of fixing the hydrogel-forming polymer or hydrogel is applied onto a face for forming the inner surface of the shaped product, and the hydrogel-forming polymer or hydrogel is fixed onto the thus applied substance.

The second process is one wherein a substance (such as sticking agent and adhesive) having a function of fixing the hydrogel-forming polymer or hydrogel is applied onto a surface of a sheet or film to be formed into the base material, the hydrogel-forming polymer or hydrogel is fixed onto the thus applied substance, and then the resultant product is shaped into a form such as pot or planter by a pressure molding process, etc.

When the above-mentioned first process is used, the material to be formed into a base material can be shaped into a form such as pot or planter by various kinds of molding processes such as injection molding, pressure molding, and blow molding. As the above substance for fixing the hydrogel-forming polymer or hydrogel to the inner surface of the shaped product, a known substance such as sticking agent or adhesive which is ordinarily commercially available can be used without particular limitation, but it is preferred to use a substance which is substantially non-toxic or has a low toxicity to a plant, as the above-mentioned substance. Specific examples of such a sticking agent or adhesive may include: sticking agents and adhesives of rubber-type, latex-type, acrylic resin-type, epoxy resin-type, urethane resin-type, protein-type, starch-type, and cellulose-type.

It is possible that the above adhesive or sticking agent is applied onto the inner surface of the above-mentioned shaped product by spraying, casting, or dipping, etc., and the hydrogel-forming polymer or hydrogel is fixed onto the thus applied adhesive or sticking agent. Further, in place of the above-mentioned adhesive, sticking agent, etc., it is also possible that a double-side adhesive-coated tape onto which the above-mentioned sticking agent, etc., has been applied in advance, is attached to the inner surface of the above-mentioned shaped product, and the hydrogel-forming polymer or a hydrogel is fixed onto the tape.

In the above first process, it is also possible that the material to be formed into the base material is shaped into a form such as pot and planter by injection molding, etc., a material obtained by dispersing a hydrogel-forming polymer or hydrogel in a thermoplastic elastomer, etc., is polymer or hydrogel in a thermoplastic elastomer, etc., is applied to the inner surface of the resultant shaped product by injection molding using a two-color molding process, whereby the hydrogel-forming polymer or hydrogel can be fixed onto the inner surface of the shaped product of the base material.

On the another hand, in the second process, it is possible that a substance (such as above-mentioned adhesive and sticking agent) capable of fixing the hydrogel-forming polymer or hydrogel is applied onto the surface of sheet or film to be formed into the base material by spraying, casting, etc., or the above-mentioned double-side adhesive-coated tape is attached thereonto, and then the hydrogel-forming polymer or hydrogel is fixed onto the thus applied or attached substance, and the resultant base material is shaped by pressure molding, etc. Further, a material obtained by dispersing the hydrogel-forming polymer or hydrogel in a thermoplastic elastomer, etc., is shaped into a multi-layer sheet or multi-layer film by a multi-layer extrusion process together with a material to be formed into the base material so that the hydrogel-forming polymer or hydrogel is fixed onto the base material sheet or base material film, and then the resultant base material is shaped by pressure molding, etc.

(Method of using plant-growing vessel or sheet)

As the method of effectively transferring (or plant-embedding) a plant by using the vessel or sheet having the hydrogel-forming polymer disposed therein according to the present invention, for example, the following methods of using the vessel or sheet may preferably be used.

(1) There is used a vessel or a sheet shaped into a vessel-type form which contains hydrogel-forming polymer particles disposed therein in an amount such that the inside of the vessel is filled with the resultant hydrogel when the polymer particles absorb water. Then, at least a part of a plant is placed in the vessel or sheet, and thereafter a (fertilizer) solution, etc., is added into the vessel so as to swell the hydrogel-forming polymer particles, thereby to fix the plant.

(2) There is used a vessel or a sheet shaped into a vessel-type form which contains hydrogel-forming polymer particles disposed therein in an amount such that the inside of the vessel is filled with the resultant hydrogel when the polymer particles absorb water. Then, a solution, etc., is added into the vessel or sheet so as to fill the vessel or sheet with the resultant hydrogel, and thereafter at least a part of a plant is inserted into the gel, thereby to fix the plant.

When the above-mentioned method (1) or (2) is used, since the swollen hydrogel particles containing water have an appropriate fluidity, the plant can smoothly be transferred without damaging the plant. Further, in the case of a minute tissue such as seed, adventive embryo to be provided by tissue culturing, and PLB (Protocorm Like Body; a tissue body provided by tissue culturing, which is similar to spherical tissue formed by the germination of a seed), it is also possible to use a method of simply placing the tissue, etc., on the hydrogel.

(3) There is used a vessel or a sheet shaped into a vessel-type form which contains hydrogel-forming polymer particles disposed therein in an amount such that the inside of the vessel is not fully filled with the resultant hydrogel when the polymer particles absorb water. At least a part of a plant is placed in the vessel together with a plant-supporting carrier, and then a solution, etc., is added into the vessel so as to swell the hydrogel-forming polymer, thereby to fix the plant.

(4) A plant is wrapped in a sheet (sheet according to the present invention) which has been coated with particles of the hydrogel-forming polymer, and is planted or embedded into an usual vessel or support, and then a solution, etc., is added into the vessel so as to swell the hydrogel-forming polymer, thereby to fix the plant.

When any of the above-mentioned (1) to (4) is used, the plant may easily be attached or fixed to the support immediately.

(Transferring method)

On the another hand, as the method of effectively transferring a plant (or taking out a plant) by using the vessel or sheet having the hydrogel-forming polymer disposed therein according to the present invention, for example, the following methods of using the vessel or sheet may preferably be used.

(1) A method wherein a large excess of water is supplied to the vessel or sheet so as to enhance the fluidity of the hydrogel, thereby to take out the plant without damaging the plant.

(2) A method of using a vessel or sheet having the hydrogel-forming polymer having an LCST disposed therein, wherein the vessel or sheet is warmed up to a temperature which does not adversely affect a plant so that the swollen hydrogel particles are caused to discharge the water content contained therein to be shrunk, whereby the plant is taken out without damaging the plant.

(3) A method wherein the vessel or sheet is supplied with warm water which does not adversely affect a plant adversely, so that the swollen hydrogel particles are caused to discharge the water content contained therein to be shrunk, and the fluidity of the gel particles is enhanced, whereby the plant is taken out without damaging the plant. The temperature of the above warm water may preferably be about 45° C. or less (more preferably about 40° C. or less), while the temperature can somewhat vary depending on the kind of the plant.

When any of the above-mentioned method (1) to (3) is used, the plant may easily be taken out from the vessel immediately without damaging the plant.

(Method of removing liquid substance such as water)

In a case where a plant is cultivated by using the vessel or sheet according to the present invention which has the hydrogel-forming polymer disposed therein, when the water content or liquid such as fertilizer solution in the vessel or sheet becomes unnecessary for a certain reason (e.g., those as described below), for example, the liquid may preferably be removed by the following method.

In view of an improvement in workability, reduction in transporting costs, etc., at the time of the transportation (such as shipment), it is important to reduce the weight of the cultivating vessel. Further, at the time of the transportation, the plant is put under a closed-type environment (e.g., a state wherein the plant is packed with cellophane together with a vessel, and put in a corrugated board) in many cases. Under such a condition, in order to prevent the damage to the plant even in a wetted state, it is important to reduce the amount of water contained in the cultivating vessel to as small amount as possible.

(1) When the vessel or sheet according to the present invention containing the hydrogel-forming polymer disposed therein, it is possible to use a method wherein the hydrogel particles are dried so that the hydrogel particles are caused to discharge water contained therein, and the weight thereof is reduced. However, it is necessary to conduct such a method in a certain range such that the resultant "concentration of nutrient" does not substantially affect the plant adversely.

(2) As a preferred method, it is possible to use a method wherein the vessel or sheet according to the present invention containing the hydrogel-forming polymer having an LCST disposed therein, the vessel or sheet is warmed up to a temperature which does not adversely affect the plant so as to shrink the hydrogel particles comprising the above polymer and cause the swollen hydrogel particles to discharge water contained therein, whereby the weight thereof is reduced, and the water content in the vessel or sheet is reduced.

In the prior art, the water which has been supplied to a plant before the shipment thereof can cause a problem such that it weaken the resistance to dryness so as to decrease the persistence of the flower, and it decrease the sugar content in the resultant fruit. Also in order to solve such a problem, it is preferred to remove water content, etc., by using the above-mentioned (1) or (2) (preferably, by the method (2)) in advance, before the shipment.

(Method of using gel-like support)

The gel-like support to be used for the plant-growing method according to the present invention comprises the above-mentioned hydrogel or polymer, and can have an appropriate "hardness" and shape-retaining property based on the gel structure in the range of temperature which is ordinarily be used for the growth of a plant (e.g., a range of about 15–35° C.). More specifically, for example, as shown in the schematic sectional view of FIG. 12, it is possible that the gel-like support 32 to be used in the present invention which is optionally disposed in the inside of a vessel 31 singly or alone without using another growing carrier such as porous material in combination therewith, thereby to grow the plant 33.

Figure 12:
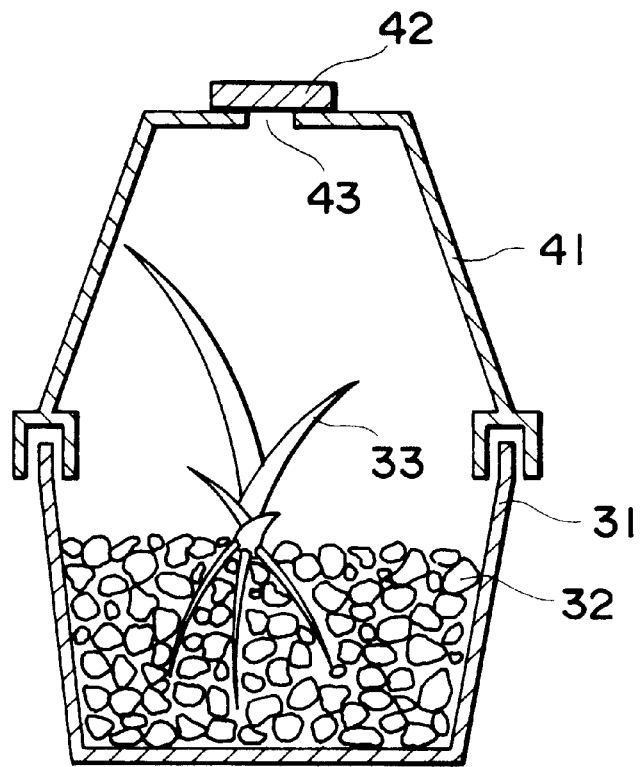
FIG. 12 is a schematic sectional view showing an embodiment of the method using a gel-like support as the support for growing a plant.

As shown in the above-mentioned FIG. 12, in the culturing stage of the plant 33, it is preferred to dispose a cap or lid 41 on the upper portion of the vessel 31 for the purpose of controlling the ventilation property of the growing system. On the top of the lid 41, an opening 43 as shown in the figure may be provided as desired. In the embodiment wherein the opening 43 is provided, a filter member 42 may further be disposed so as to cover the opening 43 as desired. It is preferred to dispose the filter member 42 in view of the prevention of contamination such as dust and bacteria. As the filter member 42, a known filter may be used without particular limitation. Preferred examples thereof may include a filter paper ("Filter Paper" (having an adhesive attached thereto) mfd. by Watanabe Tai K. K.), a membrane filter (Milli-Seal mfd. by Millipore Co.), etc. The opening 43 of the lid 41 may be single, or plural as desired. In general, the dimension of the opening 43 may preferably be about several millimeters to about several centimeters (preferably about 5 mm–1 cm).

The material, thickness, dimension, etc., of the above-mentioned vessel 31 or lid 41 is not particularly limited, but it is preferred to use polycarbonate having a thickness about several millimeters (e.g., about 1 mm) in view of the heat resistance in sterilization and transparency.

Figure 13:
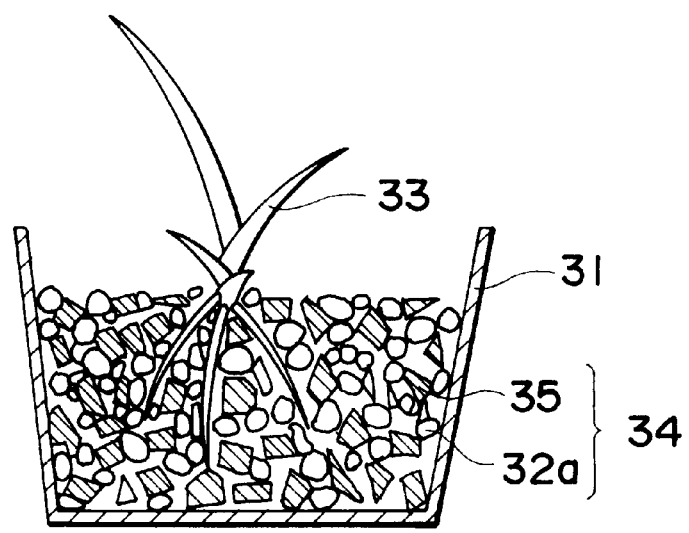
FIG. 13 is a schematic sectional view showing an embodiment of the method of using a mixture of a gel-like support and a porous material as the support for growing a plant.

In the culture stage, the lid 41 may preferably be disposed on the vessel 31 as shown in FIG. 12, but in the cultivation stage (such as greenhouse, farm), it is preferred that the lid 41 is not disposed in view of the ventilation property (as shown in FIG. 13 appearing hereinafter).

(Porous material)

The above-mentioned gel-like support may singly be used as a plant-growing support or planting (embedding) support by itself, but may also be used in combination with another porous material in consideration of the easiness or growth cost in the growth of the plants body. According to the present inventors' experiments, it has been found that when a support comprising 100% of hydrogel is used in the cultivation (e.g., farm cultivation), the oxygen in the subsurface zone can be insufficient and the elongation of the root can be obstructed in a certain case depending on the kind of such a gel.

In order to effectively prevent the oxygen deficiency in such a subsurface zone, it is preferred that the above-mentioned gel-like support is appropriately added to another porous material, and the resultant mixture is used. More specifically, for example, as shown in the schematic sectional view of FIG. 13, the gel-like support 32a to be used for the present invention is substantially uniformly added to another porous material 35 to prepare a support for a plant 34, and the thus obtained support 34 for a plant is disposed in the inside of an appropriate vessel 31, thereby to grow the plant 33.

FIG. 13 shows a state in the cultivation stage. In the cultivation stage, a lid 41 is usually disposed on the upper portion of the vessel 31 as shown in FIG. 12 (in the same manner as those shown in FIGS. 14 and 15 appearing hereinafter).

As described above, the kind, ratio at the time of use thereof, etc., of "another porous material" to be usable in combination with the gel-like support used for the present invention is not particularly limited as long as it is a porous material having pores or voids. While the mixing ratio of the gel-like support with the porous material can appropriately be regulated depending on the kind of the gel and/or porous material, etc., but, in view of the efficiency in the exhibition of the function of the gel-like support, the mixing ratio may preferably be about 1%–80% (more preferably about 10–70%, particularly about 30–50%) in terms of the "apparent volume" of the porous material to be mixed on the basis of the "apparent volume" of the polymer gel as the reference (100%).

Herein, the above-mentioned "apparent volume" refers to the volume of the "scale" of a graduated cylinder corresponding to the gel surface when the polymer gel of in an equilibrium water absorption state is calmly poured into the graduated cylinder. Further, the apparent volume of the porous material to be mixed refers to the volume measured in the same manner as described above.

As such a porous material, it is preferred to use, e.g., pearlite, vermiculite, pumice, ceramic, zeolite, sponge, sponge gourd fiber, rock wool, crushed coconut shell, bark, peat moss, Bakuhan-stone, carbide, wool, singly or as a mix of two or more kinds thereof as desired.

Figure 14:
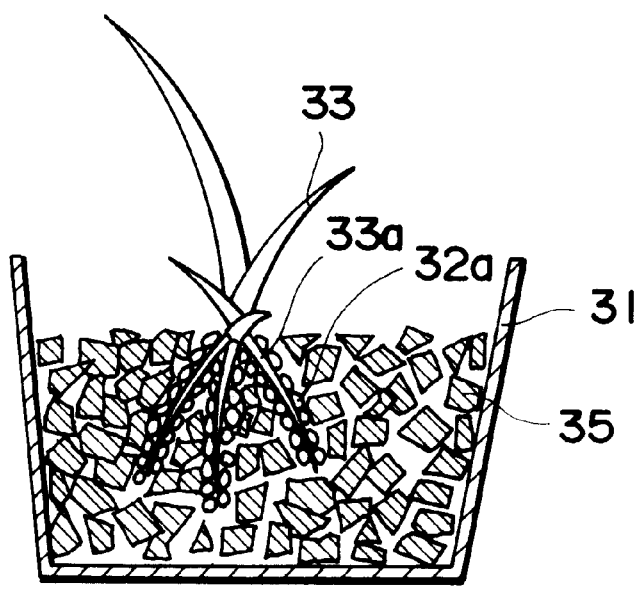
FIG. 14 is a schematic sectional showing an embodiment of the method of using a gel-like support which has been attached to the root of a plant in combination with a porous material.

Further, when the plant 33 is transferred to an ordinary plant-growing carrier such as porous material, as shown in the schematic sectional view of FIG. 14, it is possible that the gel-like support 32a to be used for the present invention is physically attached to the root 33a of the plant 33, and then the plant is embedded in the above-mentioned plant-growing carrier (such as porous material) 35 to bury the root 33a in the plant-growing carrier 35, thereby to grow the plant (as the cultivation after the culturing).

Figure 15:
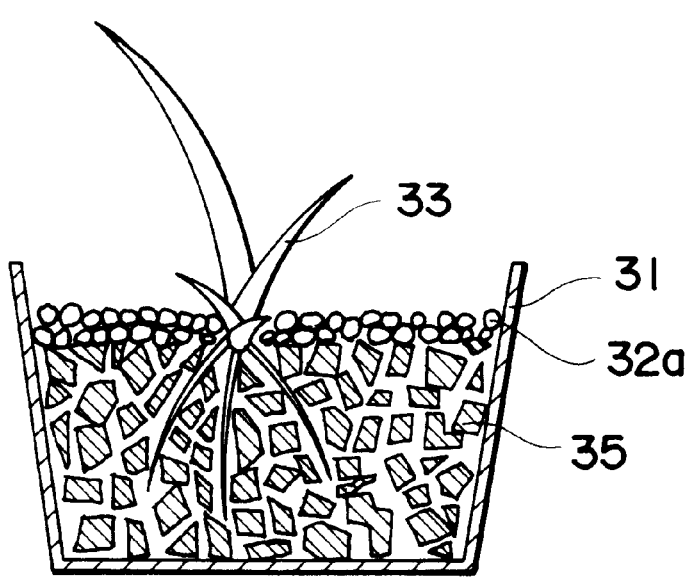
FIG. 15 is a schematic sectional showing an embodiment of the method of using a gel-like support disposed on the surface of a porous material.

Further, as shown in the schematic sectional view of FIG. 15, the plant 33 is embedded in an ordinary porous material 35, and then the gel-like support 32a to be used for the present invention is distributed or sprinkled onto the surface of the porous material 35, thereby to grow the plant (as the cultivation after the culturing).

In the above-mentioned embodiments shown in FIGS. 12–15, the gel-like support 32 and the vessel 31 which have been used in the culture stage, are also used in the cultivation stage as they are. However, it is also possible to use a vessel to be used in the cultivation stage which is different from the vessel used in the culture stage as desired.

Figure 16:
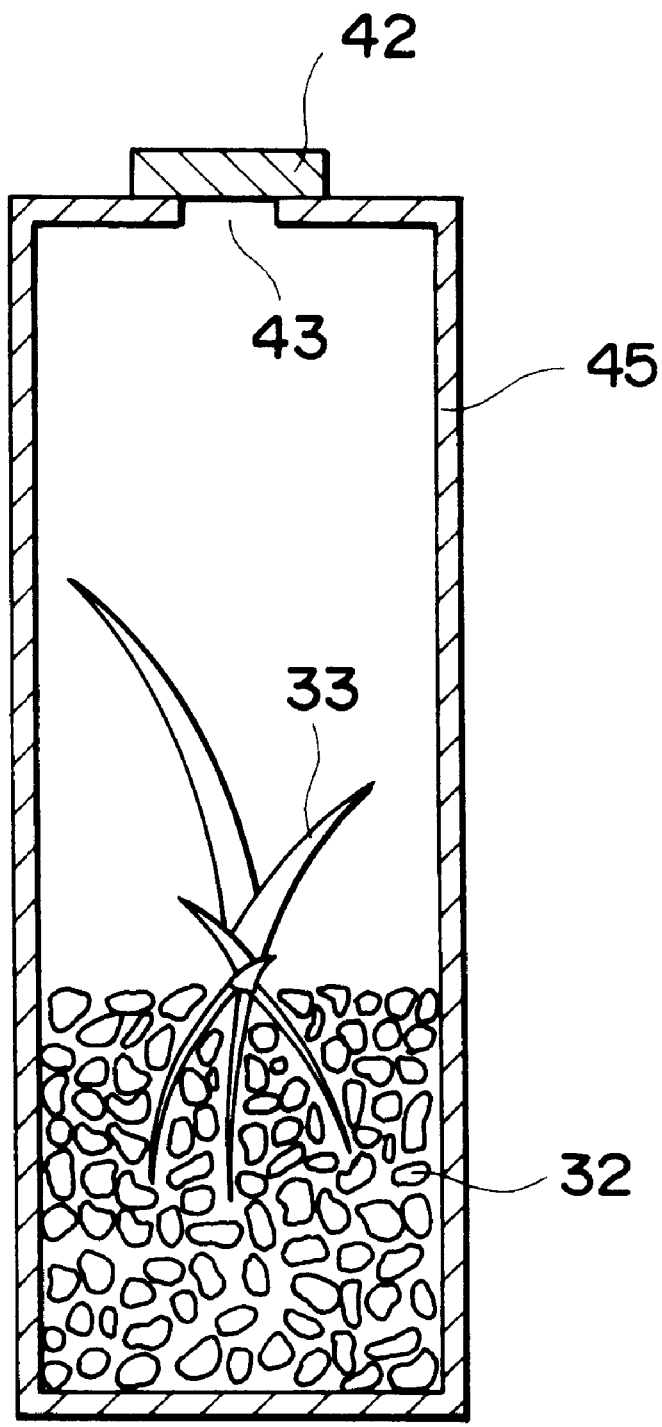
FIG. 16 is a schematic sectional view showing an embodiment of the method of using a gel-like support as the support for growing a plant in a culturing vessel.
Figure 17:
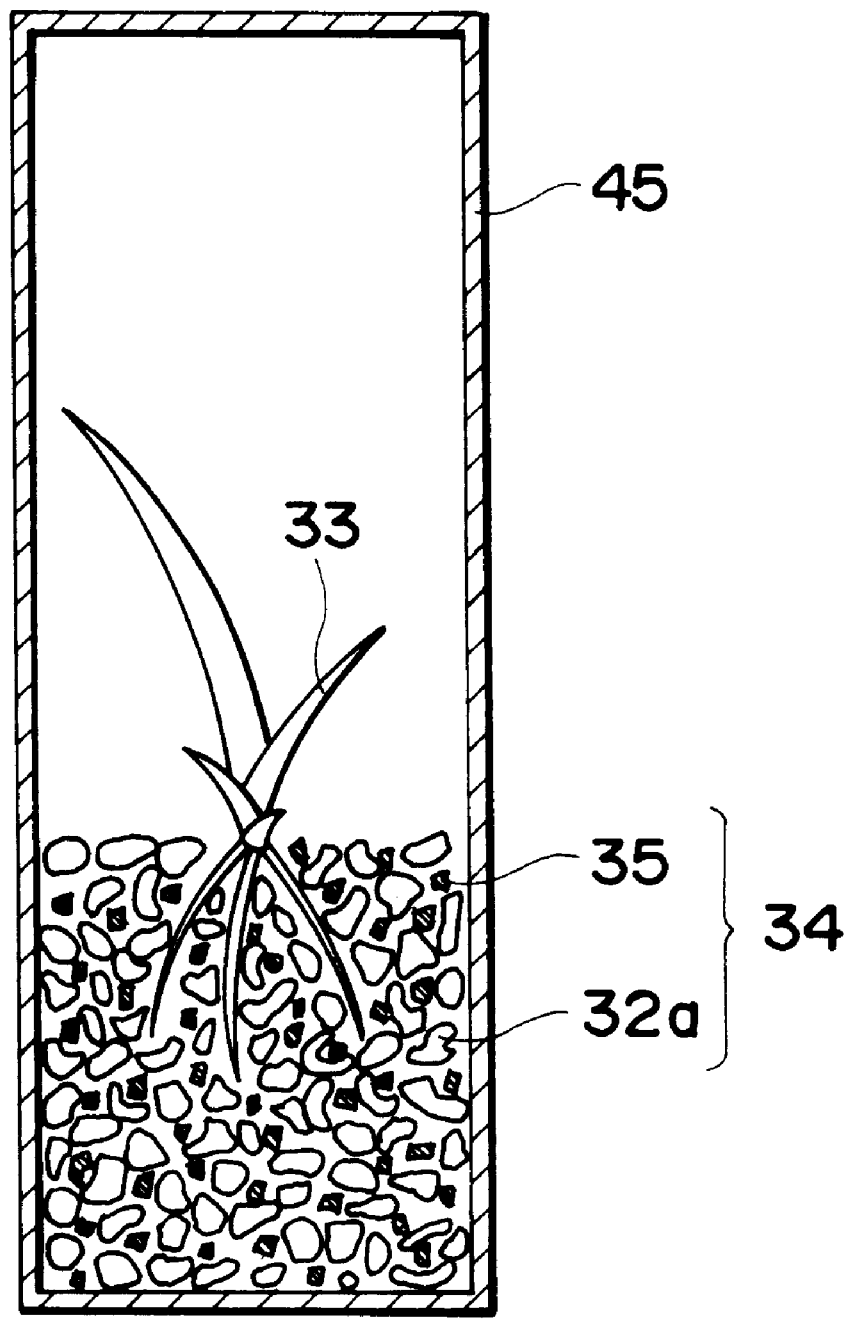
FIG. 17 is a schematic sectional showing an embodiment of the method of using a mixture of a gel-like support and a porous material as the support for growing a plant in a culturing vessel.
Figure 18:
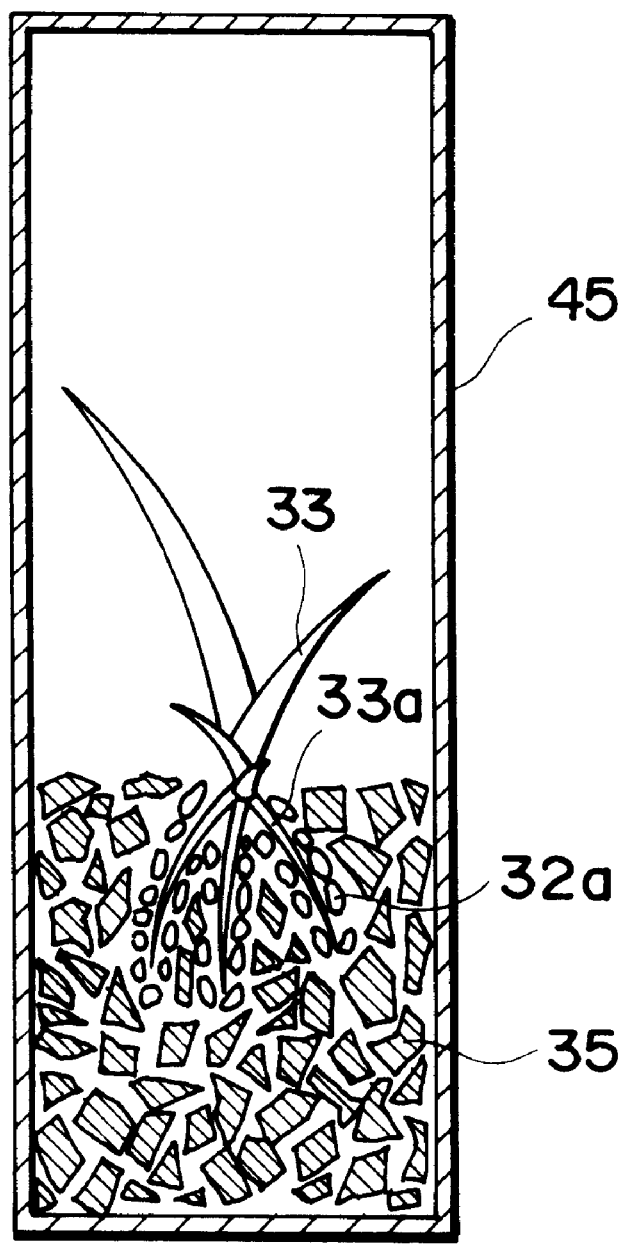
FIG. 18 is a schematic sectional view showing an embodiment of the method of using a gel-like support which has been attached to the root of a plant in combination with a porous material in a culturing vessel.
Figure 19:
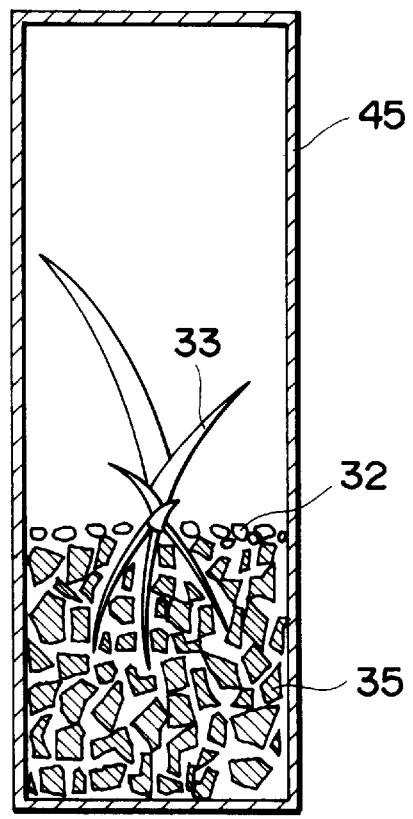
FIG. 19 is a schematic sectional view showing an embodiment of the method of using a gel-like support disposed on the surface of a porous material in a culturing vessel.

The latter embodiment is shown in the schematic sectional view of FIG. 16. Referring to FIG. 16, this embodiment may be conducted in the same manner as in the embodiment of FIG. 12 except for using a vessel 45 to be used for the cultivation exclusively, instead of the vessel 31 and lid 41 as shown in FIG. 12 which are usable in both of the culture and cultivation stages. Each of the embodiments shown in the schematic sectional views of FIGS. 17–19 (the opening 43 of the vessel 45 and the filter member 42 are omitted from these views) may be conducted in the same manner as in the embodiments of FIGS. 13–15 except for using a vessel 45 to be used for the cultivation exclusively, instead of the vessel 31 and lid 41 as shown in FIGS. 13–15 which are usable in both of the culture and cultivation stages.

The embodiments in the cultivation stage corresponding to the embodiments of FIGS. 16–19 (culture stage) are respectively shown in schematic sectional views of FIGS. 20–23.

Figure 20:
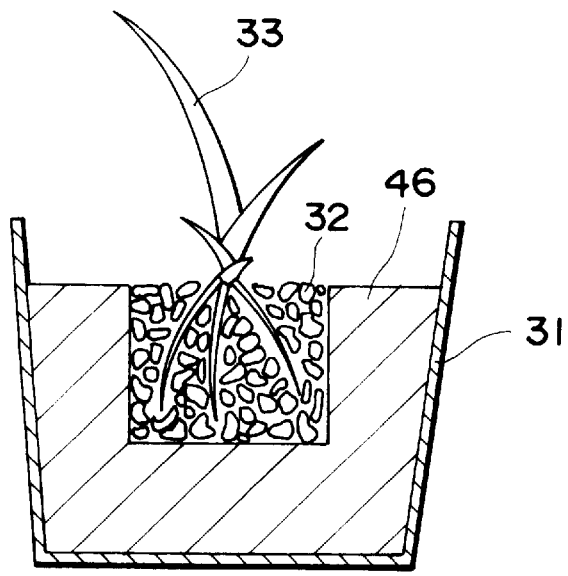
FIG. 20 is a schematic sectional view showing an embodiment of the method of using a mixture of a gel-like support and a porous material as the support for growing a plant in a cultivating vessel.
Figure 21:
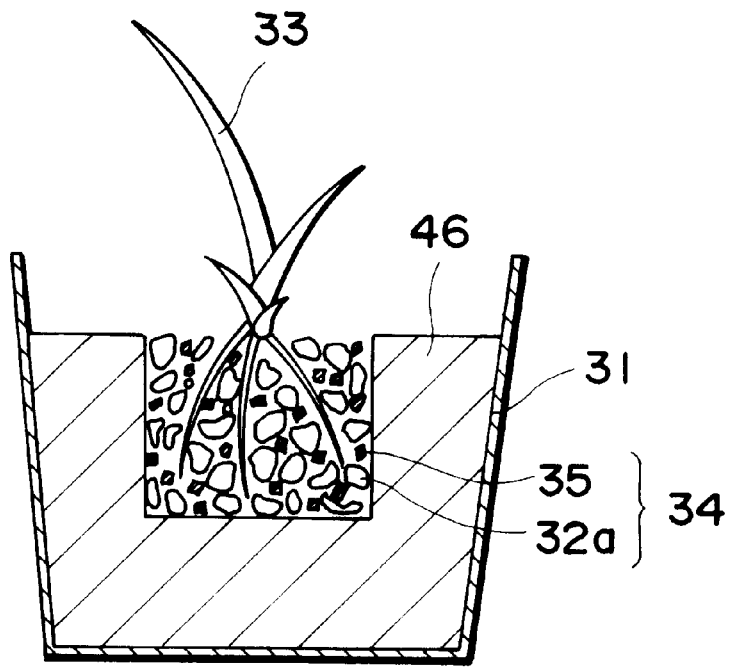
FIG. 21 is a schematic sectional view showing an embodiment of the method of using a gel-like support as the support for growing a plant in a cultivating vessel.
Figure 22:
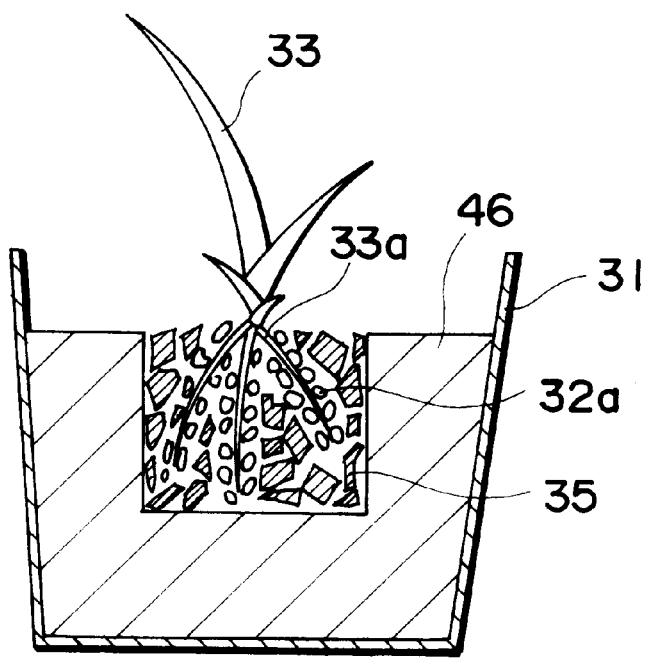
FIG. 22 is a schematic sectional view showing an embodiment of the method of using a gel-like support which has been attached to the root of a plant in combination with a porous material in a cultivating vessel.
Figure 23:
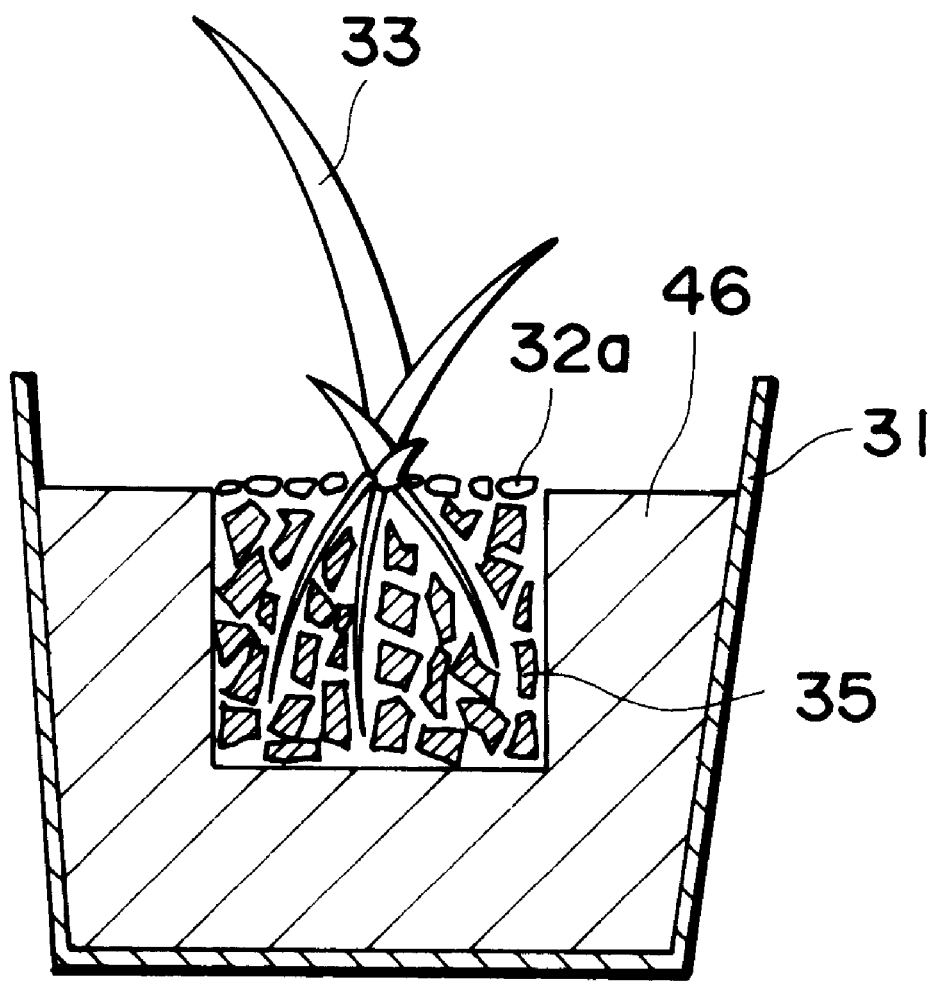
FIG. 23 is a schematic sectional view showing an embodiment of the method of using a gel-like support disposed on the surface of a porous material in a cultivating vessel.

Referring to FIG. 20, in this embodiment, the plant 33 and support 22 which have been taken out from the cultivation vessel 45 of FIG. 16, are disposed in the vessel 31 together an planting material 46 for cultivation (to be used as desired). As the cultivation planting material 46 to be used in embodiment of FIG. 20, a known planting material (such as the above-mentioned porous material and soil) can be used without particular limitation. For example, it is possible to use the above-mentioned gel-like support 32, (gel-like support 32+porous material 35), or porous material 35, etc. Depending on the kind of the plant 33, ordinary soil can also be used as the embedding material 46 for cultivation.

(Plant)

The plant to which the gel-like support used for the present invention is applicable is not particularly limited, but may be either of a plant per se (such as plantlet and seed), or a part of the plant (such as adventive embryo, callus and stem). In view of the efficiency or yield in open-air field (or bare ground) cultivation or facility cultivation (such as greenhouse), it is preferred that the plant is grown in a culturing chamber (ordinarily, under a sterilized condition) to a certain extent, and then is transferred to cultivation as it is.

(Growth condition)

The gel-like support used for the present invention can preferably be used either under the "culture" condition and the "cultivation" condition. Further, the gel-like support can preferably be used either under a sterilized or non-sterilized condition, and/or under sugar-free or sugar-involving condition. At the time of the transfer of from the culture to cultivation, when there is a difference between the composition of the culturing and fertilizer solutions (e.g., sugar-free or sugar-involving) and the exchange of the solution is preferred on the basis of such a difference, it is preferred that the above-mentioned gel-like support is once shrunk by using a temperature change, etc., so as to remove the culturing solution from the gel-like support or to wash the support, as desired, as shown in Example appearing hereinafter.

In view of the reproducibility in the growth of a plant, "culture" may preferably be conducted in a culturing chamber wherein the plant growth condition is retained substantially constant (e.g., 25° C., illuminance 3000 lux, 16h-fluorescent light illumination).

On the other hand, in the "cultivation" in the present invention, the condition for the growth of the plant is changed by a change in the external environmental factor (such as temperature, humidity, quantity of solar radiation, light intensity).

Further, for the purpose of acclimation of a plant, etc., there is a case wherein the "culturing" condition is made closer to the "cultivation" condition (e.g., there is used a greenhouse having a temperature difference between night and day, or a culturing chamber which is set to 25° C. at daytime, and 19° C. at night, with a temperature difference of 6° C.). Further, there is also a case wherein the "cultivation" condition is made closer to the "culture" condition (e.g., vessel cultivation in a culturing chamber under a non-sterilized condition) for the purpose of controlling the "cultivation" condition in a preferred manner with respect to the plant.

In the "cultivation" according to the present invention, the other conditions (such as vessel for accommodating a plant, and cultivation place or site) may arbitrarily be selected as long as the plant is grown under the non-sterilized condition. More specifically, for example, the shape of the cultivating vessel is not particularly limited, but vessel having a known shape such as pot may appropriately be used. The material constituting the vessel is not particularly limited, but and a known material such as paper, plastic, ceramic, and glass may appropriately be used. The site or place for cultivation is not particularly limited but an open-air place such as field or bare ground; and facility such as greenhouse, plant factory, and culturing chamber may appropriately be used.

As described above, the gel-like support to be used in the present invention may commonly be used under a sterilized condition and under a non-sterilized condition. Accordingly, when the plant-cultivating support or soil-modifying agent according to the present invention is used, the culture and cultivation of the plant may be conducted by commonly using the cultivating support or gel-like support. In the operation or manipulation in the transfer from the culture to cultivation by using such a common cultivating support or gel-like support, as desired, a part of entirety of the medium (component such as water, and/or another nutrient)to be retained or incorporated in the inside of the hydrogel or polymer may be exchanged by utilizing the above-mentioned temperature-responsive property of the hydrogel-forming polymer, while the hydrogel-forming polymer being attached to the plant. Accordingly, it is possible to effectively prevent the damage to the plant or a part thereof (such as root) at the time of the transfer of the plant.

(Vessel)

Figure 31:
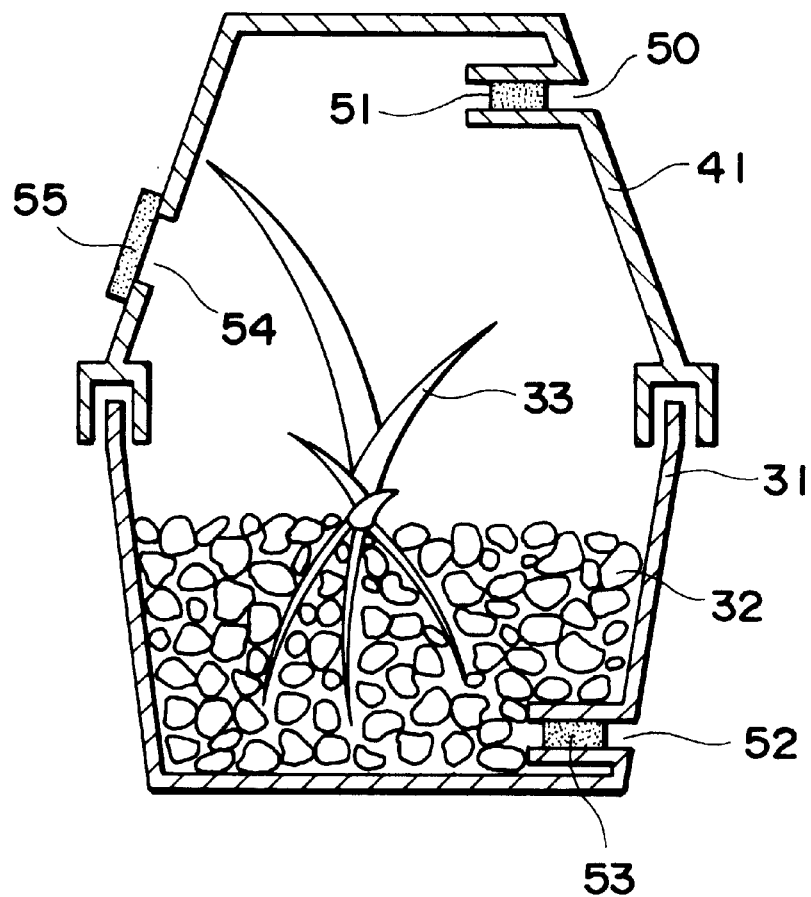
FIG. 31 is a schematic sectional view showing an embodiment of the vessel having feed and discharge ports for a liquid culture medium and a filter portion for air circulation provided therein.

When a liquid culture medium is supplied during the growth of a plant, as shown in the schematic sectional view of FIG. 31, a liquid culture medium feed port 50 may preferably be provided in the upper portion (lid portion) 41 of the a vessel for cultivating a plant 33a. Similarly, when the liquid culture medium is to be removed, a liquid culture medium outlet 52 may preferably be provided in the lower portion 31 of the vessel. When the liquid culture medium is sterilizedly supplied to the plant, the supply and discharge operations for the liquid culture medium may easily be conducted by using these two or more ports.

The above feed port 50 can be disposed on the top of the lid 41. However, in order to prevent the contamination from the air, or to enable the supply of the liquid culture medium to the vessel as shown in FIG. 31, which is in the stacked or superposed state, the above feed port 50 may preferably be disposed on the side face of the lid 41, as shown in FIG. 31. A plurality of the feed port 50 and outlet 52 may be disposed as desired.

It is preferred to respectively dispose stoppers 51 and 53 ordinarily comprising a soft or porous material such as rubber, silicone rubber, and sponge on the feed port 50 and outlet 52. When such a stopper is disposed, it is possible that the liquid culture medium is sterilizedly supplied or discharged through the stopper 51 or 53 by using a feeding or discharging measure such as syringe (not shown).

Further, in order to increase the feed of $CO_2$ to a plant, or to increase the resistance of the plant to dryness, it is preferred to provide an opening 54 for conducting air circulation in the lid 41 shown in the figure, and to dispose a filter member 55 on the opening 54.

Figure 32:
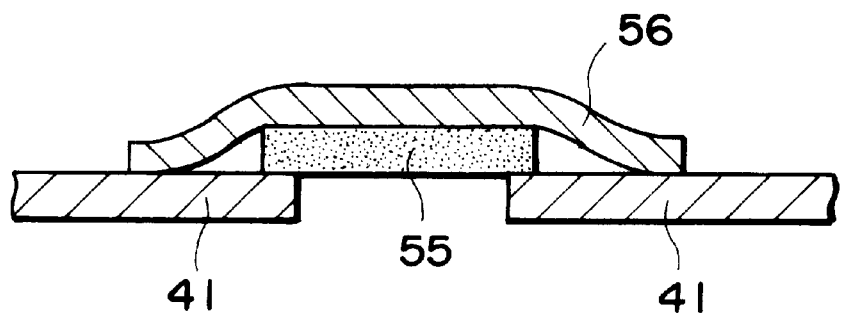
FIG. 32 is a schematic sectional view showing an embodiment of the plant-growing vessel wherein a sealing member is disposed on the filter portion of FIG. 31.

Along with the elongation of the plant, the ventilating property of the growing vessel may preferably be increased. In such a case, as shown in the partially enlarged schematic sectional view of filter portion of FIG. 32, for example, it is preferred to dispose a seal member 56 on the filter member 55 so as to seal the filter member 55. When such an arrangement is used, the air circulation in the vessel is increased so as to easily conduct the acclimation of the plant, by gradually tearing off the seal 56 with the elapse of time (extension of the plant).

The above filter 55 can be disposed on the top of the lid 41. However, in order to prevent the contamination from the air, or to enable the air circulation in the vessel as shown in FIG. 31, which is in the stacked or superposed state, the above filter 55 may preferably be disposed on the side face of the lid 41, as shown in FIG. 31. A plurality of the filter 55 may be disposed as desired.

(Method of disposing gel in the inside of vessel)

In the present invention, it is possible to dispose one plant (such as plantlet) in one vessel so as to grow the plant. However, in view of the reduction in the space, labor or cost, it is preferred to dispose a plurality of plant in one vessel.

When a plurality of plant are disposed in one vessel in such a manner, in the process of the elongation of the plant, it is possible that the roots of the plural plants are entangled with each other, and particularly in the case of a certain kind of plant wherein root hair is to be developed, the degree of entanglement becomes larger. In such a case, at the time of the transfer to farm cultivation, it is usually necessary to divide the plants into each one plant (conversion into a single plantlet).

In order to prevent entanglement between plural roots of the plants so as to avoid the damage to the root in the conversion into a single plantlet, and to simplify or facilitate the conversion into a single plantlet, it is preferred to dispose a barrier (partition) between the plural plants disposed in the vessel. As the method of disposing the barrier or partition, a known method can be used without particular limitation, as long as it reduces the entanglement between roots of plural plants so as to facilitate the conversion into a single plantlet. In order to reduce the root entanglement as effectively as possible, the "partition" may preferably disposed in a region of from the surface of the culture medium (the upper end of the gel-like support) to the bottom of the vessel. More specifically, for example, it is possible to use a vessel having therein the "partition", or to divide a vessel by using a partition in the shape of lattice or grid-type. In the former case, it is preferred to use a known vessel having a partition such as so-called tray for plug-type plantlet, mix-compost, etc., comprising plastic or foam styrol.

On the other hand, in the latter case, as the shape of the partition, the material (e.g., film or sheet comprising plastic, paper, fabric, non-woven fabric, etc.), a known product can be used without particular limitation.

When the plant before the culturing is sterilized by using an autoclave, etc., at a high temperature, the above vessel and/or partition may preferably have a predetermined heat resistance.

Hereinbelow, the present invention will be described in more detail with reference to Examples.

EXAMPLE

Example 1

15 g of N-isopropyl acrylamide (NIPAAm, mfd. by Kojin K. K.), 0.47 g of acrylic acid, 0.1 g of N,N'-methylenebisacrylamide (Bis), 0.2 g of ammonium persulfate, 6.6 mL of 1N-NaOH, and 0.1 mL of N,N,N',N'-tetramethylethylene diamine were dissolved in 90 mL of distilled water. The resultant mixture was subjected to polymerization for 4 hours at room temperature, thereby to obtain a poly-N-isopropyl acrylamide (PNIPAAm) hydrogel having a crosslinked structure.

The resultant gel was mechanically crushed by means of a mixer, thereby to prepare indeterminately shaped blocks (C-PNIPAAm-H). The C-PNIPAAm-H was dispersed in one liter of distilled water and cooled to 4° C. Thereafter, the resultant mixture was warmed to 50° C. so as to shrink the C-PNIPAAm-H, and the resultant supernatant liquid was discarded. Such awashingoperationwas repeated two times, thereby to remove the unreacted monomer and the remaining polymerization initiator. Further, the C-PNIPAAm-H was dried under vacuum, thereby to obtain powdery C-PNIPAAm-H (hydrogel-forming polymer).

Figure 24:
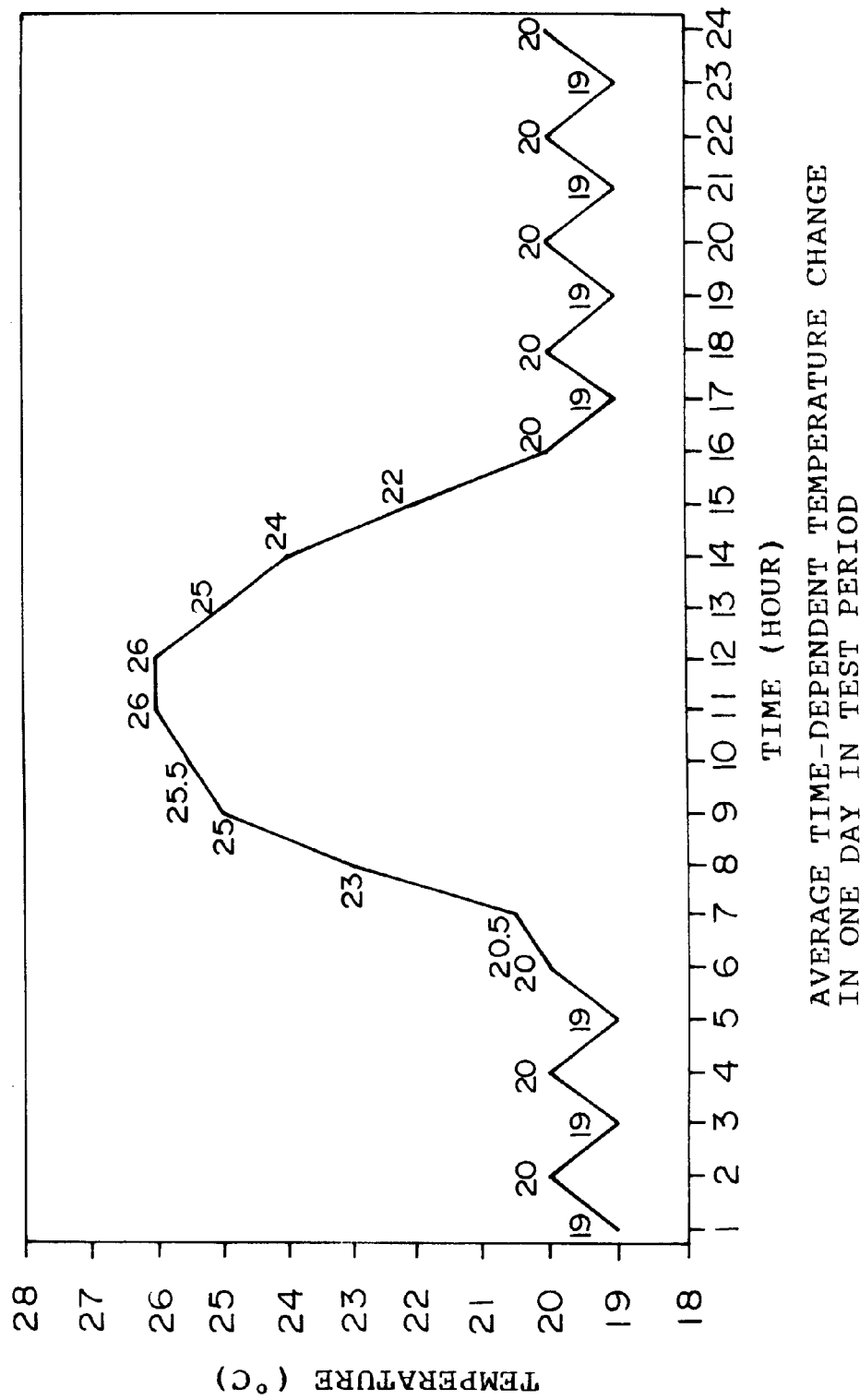
FIG. 24 is a graph showing an average temperature change with the elapse of time in one day in a greenhouse used in Example appearing hereinafter.

The equilibrium water absorption of the thus obtained C-PNIPAAm-H powder with respect to a commercially available powder horticultural fertilizer (trade name: Hyponex 20-20-20, mfd. by Hyponex Japan K. K.; 1 g/L) was measured at 19° C. and 26° C. according to the method as described hereinabove. The thus measured equilibrium water absorption was about 7200% at 19° C., and 5200% at 26° C. The temperatures of 19° C. and 26° C. used herein are those corresponding to the lowest and highest temperatures in a greenhouse wherein a plant was cultivated in Example appearing hereinafter (as shown in the graph of FIG. 24 appearing hereinafter).

Example 2

(Use of hydrogel-forming polymer plant-cultivating support)

Into an Erlenmeyer flask (mfd. by Shibata Harno K. K., capacity: 500 ml), 200 ml of a commercially available powder horticultural fertilizer (Hyponex 7-6-19, mfd. by Hyponex Japan K. K, 3.5 g/L) containing 20 g/L of sucrose, 100 g/L of banana, and 6 g/l of agar was poured, was sterilized by an autoclave treatment (121° C., 1.2 Kg/cm2, 20 minutes), and then left standing at room temperature so as to be solidified.

On the surface of the above sterilized culture medium, orchid plantlets of YT-57 (Cym. LOVELY ANGEL 'The Two Vergins') which had been grown so as to provide a length of 2 cm were transferred in a number of 25 plantlets per one flask, and were sterilizedly cultured in a culturing chamber (25° C., 3000 lux, 16h-fluorescent light illumination). After four months counted from the initiation of the culturing, the thus obtained YT-57 plantlets were taken out from the flask together with the culture medium, and then the agar containing the liquid culture medium attached to the root thereof was removed under flow of water. Among the resultant plantlets, 10 plantlets having a fresh weight of 2.4 g were selected.

Then, 8 g of the dry C-PNIPAAm-H powder, which had been obtained in Example 1 was mixed and dispersed in 500 ml of a powder horticultural fertilizer (trade name: Hyponex 20-20-20, mfd. by Hyponex Japan K. K., 1 g/L), and was left standing at room temperature so that the above-mentioned C-PNIPAAm-H powder completely absorbed the Hyponex solution, thereby to prepare a hydrogel.

The thus obtained hydrogel was disposed in a black vinyl pot having a diameter of 12 cm (mfd. by Kaneya Shoten), the above-mentioned ten YT-57 plantlets were inserted into the hydrogel (transferring) per one pot, and was subjected to ordinary cultivation in a greenhouse (temperature: 18–30° C.). In this cultivation in the greenhouse, watering was effected every three or four days so that the weight of the whole pot becamethesameastheinitialvaluethereof. Anaverage temperature change in one day in the cultivation in above-mentioned greenhouse with the elapse of time in the test period was one as shown in graph of FIG. 24.

After 50 days counted from the initiation of the cultivation in the above-mentioned greenhouse, the fresh weight of each plantlet was measured, the average thereof was 4.1 g/one plantlet (as shown in the following Table 1). In the appearance of thus obtained plantlets, the root was well extended, and there were observed many plantlets wherein a new root was originated from the base portion thereof. The leaf color was thick in the stem and leaf portion, the increase in the number of leaves was two or more in average, and the growth of the above-ground portion was also very good.

Example 3

In a plant box (Shibata Hario K. K., made of polycarbonate, upper part=75×75 mm, lower part 65×65 mm, height=100 mm), 1.7 g of the dry C-PNIPAAm-H powder prepared in Example 1 was mixed with and dispersed in 105 mL of a Hyponex culture medium used in Example 2. The thus obtained dispersion liquid was divided into nine portions by using a paper pot (mfd. by Nippon Tensai Seito K. K.), and was sterilized by an autoclave treatment (121° C., 1.2 Kg/cm2, 20 minutes), and left standing at room temperature. As a result, the C-PNIPAAm-H polymer powder completely absorbed the culture medium to be converted into a gel state.

In the above plant box, on the surface of the above gel divided into nine portions, 9 plantlets of YT-57 which had been grown so as to provide a leaf length of about 2 cm were transferred per one portion thereof, and were sterilizedly cultured in a culturing chamber (25° C., 3000 lux, 16h-fluorescent light illumination).

After three months counted from the initiation of the culturing, when the plantlets were grown so as to provide a length thereof of about 10 cm, the plant box was non-sterilizedly immersed in warm water at 35° C. for 20 minutes. As a result, the C-PNIPAAm-H was shrunk to be completely aggregated, and almost all of the Hyponex culture medium which had been contained in the carrier was discharged from the completely aggregated carrier.

The stopper (made of silicone) for a 5 mm-diameter opening which had been provided in the above plant box in advance, was removed, and the culture medium discharged in the above step was flown out and removed. Then, the above stopper was again provided to the opening of the plant box.

About 100 mL of aqueduct water at a temperature of about 16° C. was added into the plant box, whereby the aqueduct water was absorbed into the (completely aggregated) C-PNIPAAm-H. Then the plant box was immersed in warm water of 40° C. so that the temperature of the water was again raised to about 35° C. to shrink the C-PNIPAAm-H to be converted into a completely aggregated form, whereby the aqueduct water was discharged from the beads-type carrier. In this manner, the Hyponex culture medium used for the above culture step was completely removed from the aggregated C-PNIPAAm-H carrier.

Wile the aggregated C-PNIPAAm-H carrier and the paper pot being attached to the root thereof, the above YT-57 after the culture was transferred into a black vinyl pot having a diameter of 12 cm (mfd. by Kaneya Shoten) by using the gel used in Example 2 as a support. By using the thus transferred YT-57, ordinary cultivation was conducted in a greenhouse. In this cultivation in the greenhouse, watering was effected every three or four days so that the weight of the whole pot became the same as the initial value thereof. An average temperature change in the cultivation in above-mentioned greenhouse in one day with the elapse of time in the test period was one as shown in graph of FIG. 24.

After 50 days counted from the initiation of the cultivation in the above-mentioned greenhouse, the appearance of thus obtained plantlet was observed. As a result, the root was well extended, and there were observed many plantlets wherein new root was originated from the base portion thereof. The leaf color was thick in the stem and leaf portion of the YT-57, the increase in the number of leaves was two or more in average per one plantlet, and the growth of the above-ground portion was also very good.

Reference Example 1

Ten plantlets of YT-57 having a fresh weight of 2.4 g were selected in the in the same manner as in as Example 2. These plantlets were transferred into a black vinyl pot having a diameter of 12 cm (mfd. by Kaneya Shoten) by using commercially available Peat-moss (produced in New Zealand) which has been used as the support for orchid most popularly. Then, the plantlets were subjected to ordinary cultivation in a greenhouse (the temperature change in one day was that as shown in the graph of FIG. 24; in the same manner as in the description appearing hereinafter).

After 50 days counted from the initiation of the cultivation, the above-mentioned fresh weight of YT-57 was 3.4 g/one plantlet (as shown in the following Table 1) in average. When the thus obtained results were compared with those in the case of using the cultivating support comprising the hydrogel or polymer according to the present invention in Example 2, it was found that the growth of the plantlet was slower in this Reference Example. In the plantlet after the above-mentioned cultivation, the root extended in its appearance, but the leaf and stem portion thereof had a thin leaf color, and the increase in the number of leaves was only one piece per one plantlet, and further, the growth of the above-ground portion of the plantlet was also slow.

Reference Example 2

Ten plantlets of YT-57 having a fresh weight of 2.4 g were selected in the same manner as in as Example 2. These plantlets were transferred into a black vinyl pot having a diameter of 12 cm (mfd. by Kaneya Shoten) by using commercially available soil of Growell MO-2 (bark produced in New Zealand, available from Mukoyama Orchid Ltd.). Then, the plantlets were subjected to ordinary cultivation in a greenhouse.

After 50 days counted from the initiation of the cultivation, the above-mentioned fresh weight of YT-57 was 3.2 g/one plantlet (as shown in the following Table 1) in average. In the plantlet after the above-mentioned cultivation, the root extended in its appearance, but the leaf and stem portion thereof had a thin leaf color, and the increase in the number of leaves was only one piece per one plantlet, and further, the growth of the plantlet per se was also slow.

The results of the growth of YT-57 obtained in Example 2 and Reference Examples 1 and 2 are inclusively shown in following Table 1.

TABLE 1

<influence of various support on growth of YT-57>

| <support name> | <fresh weight (g/one platelet)> |
| --- | --- |
| C-PNIPAAm-H | 4.1 |
| Peat-moss | 3.4 |
| Bark | 3.2 |

In the above Table 1, the weight of a plantlet before the transferring was all 2.4 g, and all the value of the "fresh weight" was determined as the average of ten plantlets (YT-57=Cym. LOVELY ANGEL 'The Two Vergins').

Reference Example 3

Ten plantlets of YT-57 having a fresh weight of 2.4 g were selected in the same manner as in as Example 2. Then, 8 g of commercially available water-absorbing polymer of dried Aquaric CA-H (mfd. by Nippon Shokubai K. K., crosslinked polyacrylic acid product, indeterminate bulk shape, dimension=1–3 mm) was mixed with and dispersed in 500 ml of solution of powder horticultural fertilizer (trade name: Hyponex 20-20-20, mfd. by Hyponex Japan K. K.; 1 g/L), and then was left standing at room temperature so that the Aquaric CA-H carrier completely absorbed the Hyponex solution, thereby to prepare a gel.

The above YT-57 plantlets were transferred into a black vinyl pot having a diameter of 12 cm (mfd. by Kaneya Shoten) by using the thus obtained gel as a support, and then, the plantlets were subjected to ordinary cultivation in a greenhouse.

In this cultivation, watering was effected every three or four days so that the weight of the whole pot became the same as the initial value thereof. After 50 days counted from the initiation of the cultivation, the state of the above-mentioned plantlet was observed. As a result, the root was not substantially extended in its appearance, but the root tip assumed necrosis. Further, the leaf and stem portion thereof had a thin leaf color, and the increase in the number of leaves was not observed, and further, the plantlet per se was not substantially grown.

Example 4

(Use of hydrogel-forming polymer as soil-modifying agent)

Plantlets of orchid MBDB (Cym. MUSIC BOX DANCER 'Ballerina') which had been cultured under a sterilized condition in the same manner as in as Example 2 were taken out from the Erlenmeyer flask used in the culture. The agar containing the liquid culture medium attached to the root was removed under flow of water, and then 10 plantlets having a fresh weight of 2.0 g were selected.

The dry C-PNIPAAm-H powder prepared in Example 1 was mixed with the commercially available soil of "Growell MO-2" used in Reference Example 2 in a mixing ratio of 0.5 wt. %, 1.0 wt. %, 1.5 wt. % and 2.0 wt. %, respectively. Byusingeach of the thus obtained supports, ten plantlets selected above were transferred into a black vinyl pot having a diameter of 12 cm (mfd. by Kaneya Shoten). A solution (0.5 g/L) of commercially available liquid horticultural fertilizer of Hyponex 20-20-20 was sufficiently supplied to the above soil by watering (irrigation), and then the plantlets were subjected to ordinary cultivation in a greenhouse.

The time-dependent temperature change on average in one day in the test period was that as shown in the graph of FIG. 24.

After 30 days counted from the initiation of the cultivation, the state of the plantlet was investigated. As a result, it was observed that the transferring (or rooting) damage (damage to the root caused by the transferring) was little, thick roots were well extended, new roots were moved from the base portion of the plantlet. Further, it was also observed that the ratio of living tissue in the neighborhood of the growing point of the root was somewhat increased, as the addition amount of the soil-modifying agent comprising the hydrogel or polymer according to the present invention was increased (as shown in the following Table 2).

Reference Example 4

Ten plantlets of MBDB having a fresh weight of 2.0 g were selected in the same manner as in as Example 4, and transferred into a black vinyl pot having a diameter of 12 cm by using the Growell MO-2 as the support. A Hyponex 20-20-20 solution of 0.5 g/L was sufficiently supplied to the above soil by irrigation, and then was subjected to ordinary cultivation in a house. After 30 days counted from the initiation of the cultivation, the state of the plantlet was investigated. As a result, it was found that in many plantlets, the tissue in the neighborhood of the growing point of the root assumed necrosis (as shown in the following Table 2).

TABLE 2

<Influence of addition concentration of soil-modifying agent C-PNIPAAm-H on root of MBDB>
(when Hyponex 20-20-20 solution was incorporated)
<Addition amount of C-PNIPAAm-H>

| (wt.) % | <root apex (tip) survival rate> (%) |
|---|---|
| 0 | 67.5 |
| 0.5 | 74.5 |
| 1 | 73.1 |
| 1.5 | 81.6 |
| 2 | 93.4 |

In the above-mentioned Table 2, "root apex survival rate" denotes the ratio of the total number of roots of which root apex portion was living, with respect to the total number of roots of ten MBDB plantlets. The "living" of the root apex was determined by observing whether the tip portion of each root assumed "browning" or not, by naked eye observation (MBDB=Cym. MUSIC BOX DANCER 'Ballerina').

Reference Example 5

Ten plantlets of MBDB having a fresh weight of 2.0 g were selected in the same manner as in Example 4. Separately, 2 wt. % of commercially available water-absorbing polymer of dried Sumicagel S-50 (mfd. by Sumitomo Kagaku Kogyo K. K., poly (acrylic acid-vinyl alcohol) copolymer, spherical shape, diameter=180–290 $\mu$m) was mixed with the commercially available soil Growell MO-2 used in Reference Example 2. By using the thus obtained support, the above ten plantlets of MBDB were transferred into a black vinyl pot having a diameter of 12 cm (mfd. by Kaneya Shoten). A Hyponex 20-20-20 solution of 0.5 g/L was sufficiently supplied to the above pot after the transferring by irrigation, and then was subjected to ordinary cultivation in a greenhouse.

After 30 days counted from the initiation of the cultivation, the state of the plantlet was investigated. As a result, it was found that the transferring damage was little in its appearance similarly as in Example 4. However, most of roots were very thin, as compared with those obtained in the plantlets after the cultivation in Example 4.

Example 5

A commercially available growth retardant of Sumi-Seven formulated concentrate (uniconazole concentration 250 ppm, mfd. by AGROS K. K.), which had usually been used as a growth retardant for a plant, was diluted by a factor of 10 times. 1000 ml of the thus obtained solution was absorbed into 50 g of the dry C-PNIPAAm-H powder prepared in Example 1, and dried at ordinary temperature, and then pulverized, thereby to prepare C-PNIPAAm-H powder containing the uniconazole.

Then, there was provided a black vinyl pot having a diameter of 12 cm (support: Growell MO-2) containing an orchid plantlet of YN-74 (Cym. SYLVAN STAR 'Venus') which had been cultivated in a greenhouse for one year, so that the reed length thereof was extended to 23 cm. Onto the surface of the support in the above vinyl pot, 0.5 g of the above-mentioned C-PNIPAAm-H powder (containing the uniconazole) was added by scattering, watering was conducted thereon for five minutes by spraying, and was subjected to ordinary cultivation in a greenhouse.

After 50 days counted from the initiation of the cultivation experiment, the reed length of the above orchid was measured, and the reed length was found to be 29.0 cm, which was only 6.0 cm longer in elongation, as compared with the original value of the reed length (23 cm). That is, it was confirmed that the uniconazole contained in the above-mentioned C-PNIPAAm-H powder exhibited its growth retardant effect (as shown in the following Table 3).

Reference Example 6

An orchid plantlet of YN-74 which had been cultivated so that the reed length thereof was extended to 16.5 cm was subjected to ordinary cultivation in the same manner as in Example 5 except for using this YN-74 was placed in a division of a black vinyl pot to which the growth retardant was not added.

After 50 days counted from the initiation of the cultivation experiment, the reed length of the above orchid was measured, and the reed length was found to be 30.5 cm, which was 14.0 cm longer in elongation, as compared with the original value of the reed length (16.5 cm) (as shown in the following Table 3).

Reference Example 7

100 ml of a solution obtained by diluting the Sumi-Seven formulated concentrate used in Example 5 by a factor of 100 times was supplied by irrigation to the soil of a stock of YN-74 which had been cultivated so that the reed length thereof was extended to 21 cm, and was subjected to ordinary cultivation in the same manner as in Example 5.

After 50 days counted from the initiation of the cultivation experiment, the reed length of the above orchid was measured, and the reed length was found to be 27.0 cm, which was only 6.0 cm longer in elongation, as compared with the original value of the reed length (21 cm). That is, it was confirmed that the growth retardant exhibited its growth retardant effect (as shown in the following Table 3).

TABLE 3

<Effect of C-PNIPAAm-H containing growth retardant on growth of reed>

| <Method of adding growth retardant> (Addition amount) | <Before growth retardant treatment (A)> Reed length (cm) | <After growth retardant treatment (B)> Reed length (cm) | <(B − A)> (cm) |
| --- | --- | --- | --- |
| C-PNIPAAm-H (0.5 g) | 23.0 | 29.0 | 6.0 |
| Soil irrigation | 21.0 | 27.0 | 6.0 |
| No addition | 16.5 | 30.5 | 14.0 |

In the above-mentioned Table 3, "C-PNIPAAm-H 0.5 g" contained 0.25 mg of uniconazole. The "soil irrigation" used 100 mL of liquid (containing 0.25 mg of uniconazole) obtained by dilution by a factor of 100 times (YN-74=Cym. SYLVAN STAR 'Venus')

Example 6

Figure 25:
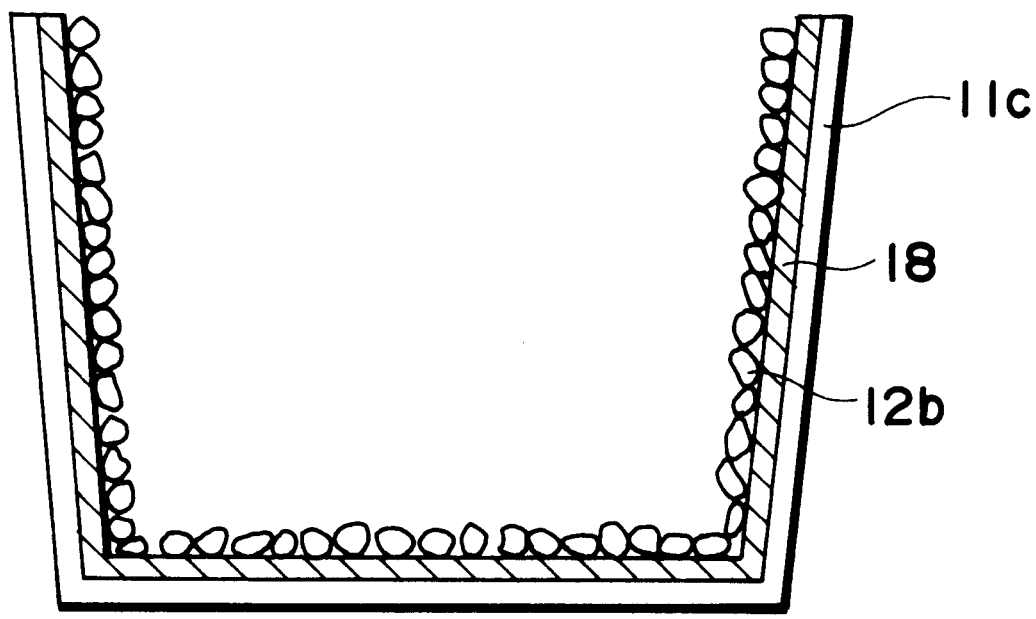
FIG. 25 is a schematic sectional view showing the plant-growing vessel according to the present invention which has been prepared in Example.

A double-side adhesive-coated paper tape (trade name: Double-side Adhesive-coated Tape, mfd. by Teraoka Seisakusho K. K.) was attached to almost all the inside surfaces (bottom and side faces) of a pot made of polyethylene (diameter ø9 cm×height 7 cm). Then, the dry PNIPAAm particles prepared in Example 1 were poured into the pot, and the pot was sufficiently shaken by manual operation, whereby the particles were substantially uniformly attached onto the above double-side paper adhesive tape. The PNIPAAm particles which had not been attached to the tape were removed by inverting the above-mentioned pot, thereby to prepare a pot (FIG. 25) wherein the inside of the pot base material 11c was coated with the PNIPAAm particles 12b by the medium of the double-side adhesive tape 18 disposed therebetween. The area of the inner surface (calculated value) was 261 cm$^2$, and the weight of the PNIPAAm particles attached to inside surface of the above-mentioned pot was 3.0 g, and therefore the application amount of the PNIPAAm particles was 0.0115 g/cm$^2$ (11.5 mg/cm$^2$).

Example 7

Onto a 0.5 mm-thick polyethylene sheet (mfd. by Takiron Co.), a rubber-type sticking agent (trade name: Three-Bond No. 1500, mfd. by Three-Bond Co.) was applied so as to provide a thickness of about 0.1 mm by means of a coater (mfd. by Yasuda Seiki Co.), and then the dry PNIPAAm particles prepared in Example 1 were applied onto the coating layer of the sticking agent so as to provide a thickness of about 0.1 mm by means of a coater. The resultant application amount of the PNIPAAm particles was 0.005 g/cm$^2$ (5 mg/cm$^2$).

By using the thus obtained sheet having a three-layer structure (dry PNIPAAm particles/sticking agent/polyethylene) as a shaping material, a pot (diameter ø9 cm×7 cm, FIG. 25) wherein the inner surface was coated with the PNIPAAm particles was prepared by means of a pressure molding machine (mfd. by Sumitomo Juki Co.).

Example 8

Onto a 0.15 mm-thick filter paper (trade name: Filter Paper, mfd. by Watman International Co.), a starch-type sticking agent (trade name: Yamato Paste mfd. by Yamato K. K.) was applied so as to provide a thickness of about 0.1 mm by means of a coater, and then the dry PNIPAAm particles prepared in Example 1 were applied onto the coating layer of the sticking agent so as to provide a thickness of about 0.1 mm by means of a coater. The resultant application amount of the PNIPAAm particles was 0.005 g/cm$^2$ (5 mg/cm$^2$).

Figure 26:
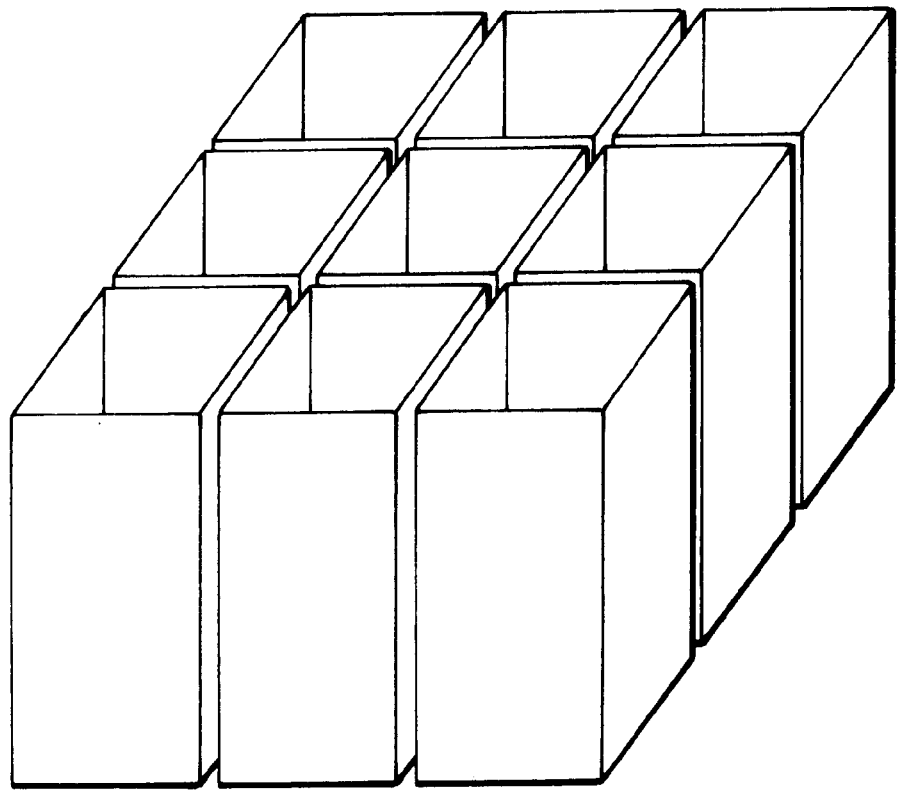
FIG. 26 is schematic perspective view showing the plant-growing sheet (partition-type) which has been prepared in Example 1.
Figure 27:
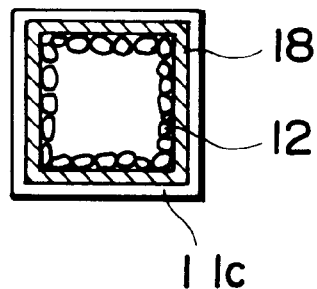
FIG. 27 is a schematic plan view showing one division of the partition-type sheet of FIG. 26 as viewed from the above.

By using the thus obtained sheet having a three-layer structure (dry PNIPAAm particles/sticking agent/filter paper) as a shaping material, there was prepared a grid-type sheet (as shown in FIG. 26) having compartments of 3×3=9, each of which had a dimension of (a length 2 cm×side 2×height 4 cm). FIG. 27 is a schematic plan view of one of the thus obtained compartments as viewed from upward.

Example 9

Into an Erlenmeyer flask (mfd. by Shibata Hario K. K., capacity: 500 ml), 200 ml of a commercially available culture medium (Hyponex 7-6-19, mfd. by Hyponex Japan K. K, 3.5 g/L) containing 20 g/L of sucrose, 100 g/L of banana, and 6 g/l of agar was poured, was sterilized by an autoclave treatment (121° C., 1.2 Kg/cm2, 20 minutes), and then left standing at room temperature so as to be solidified.

On the surface of the above sterilized culture medium, 25 young orchid plantlets of SJIC (Cym. SARAH JEAN "Ice cascade") which had been grown so as to provide a length of about 2 cm were transferred per one Erlenmeyer flask, and were sterilizedly cultured in a culturing chamber (25° C., 3000 lux, 16h-fluorescent light illumination). After four months counted from the initiation of the culturing, the thus obtained SJIC plantlets were taken out from the flask together with the culture medium, and then the agar containing the liquid culture medium attached to the root thereof was removed under flow of water. Among the resultant plantlets, many plantlets having a fresh weight of 2.8 to 3.2 g (average: 3.0 g) were selected.

Commercially available Growell MO-2 (available from Mukoyama Orchids Ltd., bark produced in New Zealand) and VAPO (available from Mukoyama Orchids Ltd., peat moss produced in North Europe) were mixed with each other in a mixing ratio of 8:2 (volume ratio). By using 250 ml of the thus obtained support, nine of the above plantlets were transferred into the pot-type vessel prepared in Example 6.

At the time of this transferring, the above-mentioned support was spread on the bottom of the pot so as to provide a thickness of about 5 mm, while retaining the above-mentioned SJIC plantlet with one hand in the space in the pot, the above mixed support was poured into the pot to fill the pot with the support so that the upper portion of the support reached a level which was about 4 cm higher than the bottom end of the pot. The operation of pressing the support (by hands) after the filling of the pot was not conducted, since such an operation is effective in fixing the plant, but on the other hand, it can damage the root.

Figure 28:
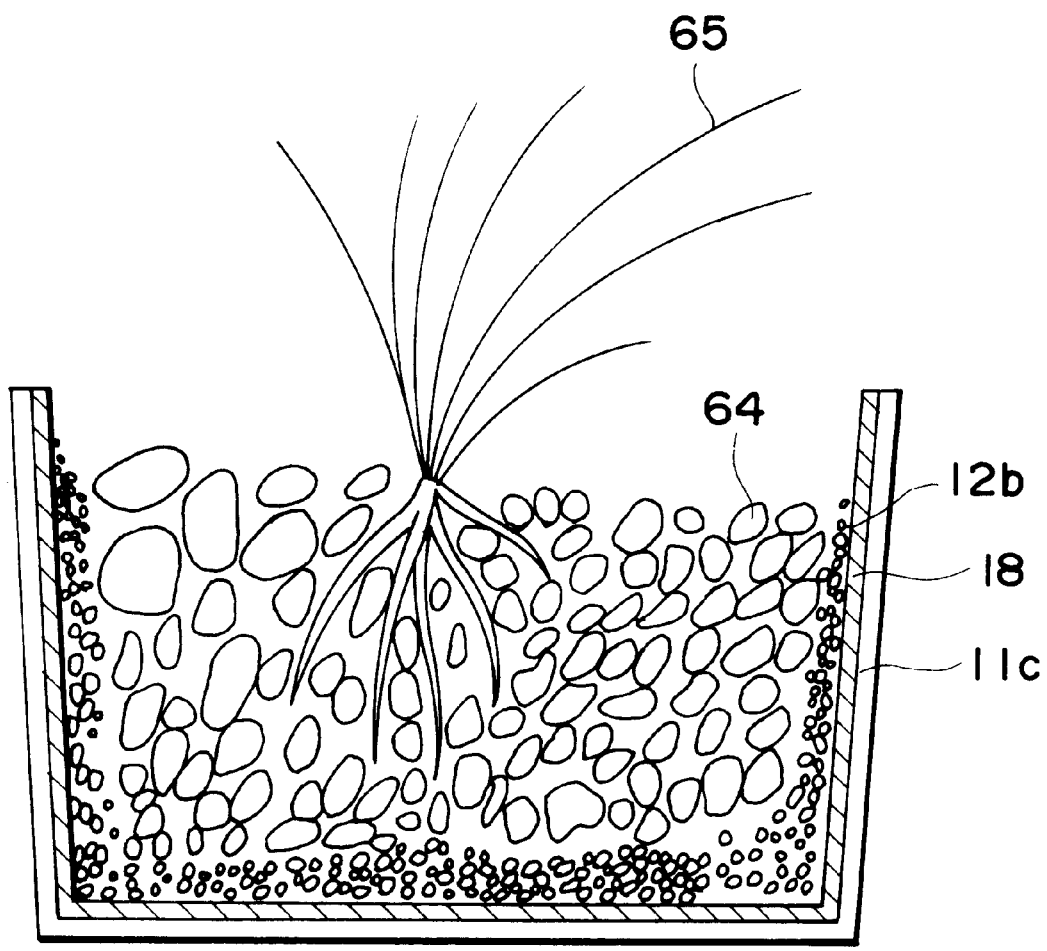
FIG. 28 is a schematic sectional view showing an embodiment wherein a support and a plant are disposed in the plant-growing vessel of FIG. 25, and water is supplied thereinto.

Into the above-mentioned pot which had been filled with the plantlet of SJIC and the support, 175 ml of a solution of powder horticultural fertilizer (trade name: Hyponex 20-20-20, mfd. by Hyponex Japan K. K., 1 g/L) was added. As a result, as shown in the schematic sectional view of FIG. 28 (only one plantlet is shown in FIG. 28), the PNIPAAm particles 12b disposed on the wall surface of the vessel were swollen toward the center of the vessel while absorbing the solution, and pressed the inner support (mixture of Growell MO-2 and VAPO) 64, whereby the fixing of the plant 65 and the attachment thereof to the support 64 were conducted indirectly without damaging the root.

The plantlet which had been transferred into the pot in this manner was subjected to ordinary cultivation in a greenhouse (average lowest temperature 19° C., average highest temperature 26° C.). Watering during the cultivation was conducted every two or three days so that the weight of the whole vessel became the same as the initial value thereof.

After 36 days counted from the initiation of the cultivation, the plantlet was taken out from the vessel and the fresh weight thereof was measured. As a result, it was found to be 4.5 g/one plantlet on average.

In the plantlet after the above-mentioned growth, the growth of the root is normal in its appearance. Particularly, the root which had reached the vessel wall surface grew very well, and there were observed many roots which further grew from the base portion. Further, when the cross section of the root which had reached the vessel wall surface (about 2 cm toward the base portion side counted from the root tip) was observed with a microscope, it was found that an innumerable number of root hairs grew between the PNIPAAm particles. Further, the leaf and stem portion had a thick leaf color, and the growth of the whole plantlet was smooth.

The temperature change in one day on average in the test period in the cultivation in the above-mentioned greenhouse was that as shown in the graph of FIG. 24.

Reference Example 8

In the same manner as in Example 9, nine SJIC plantlets having an average fresh weight of 3.0 g were selected, and were transferred into the pot-type vessel used in Example 6 by using as the support 400 ml of a mixture comprising Growell MO-2 and VAPO in a mixing ratio of 8:2 (volume ratio), except for using the commercially available pot used in Example 6 as it is (without the application of the PNIPAAm particles). At this time, since it was difficult to fix the plant by using the support occupying the pot alone, the plant was fixed by lightly pressing the support downward by hands. Into the above-mentioned pot wherein the plant had been fixed, 175 ml of a solution of powder horticultural fertilizer used in Example 9 was added.

The plantlet was subjected to ordinary cultivation in a greenhouse (average lowest temperature 19° C., average highest temperature 26° C.) in the same manner as in Example 9 except for using the thus fixed pot. Watering during the cultivation was conducted every two or three days in the same manner as in Example 9 so that the weight of the whole vessel became the same as the initial value thereof.

After 36 days counted from the initiation of the cultivation, the plantlet was taken out from the vessel and the fresh weight thereof was measured. As a result, it was found to be 3.5 g /one plantlet on average. In the resultant plantlet, lower leaves in the leaf and stem portion were withered in its appearance, and it was observed that the tips and side faces of roots caused browning and fatal withering (According to the investigations of the present inventors, it is presumably considered that an excess of water content adversely affected the root as one of the causes for such a phenomenon). Further, when the cross section of the root which had reached the vessel wall surface (about 2 cm toward the base portion side counted from the root tip) was observed with a microscope, substantially no root hairs were observed.

Reference Example 9

In the same manner as in Example 9, nine SJIC plantlets having an average fresh weight of 3.0 g were selected, and were transferred into the pot-type vessel used in Example 6 by using as the support 400 ml of a mixture comprising Growell MO-2 and VAPO in a mixing ratio of 8:2 (volume ratio), except for using a commercially available black vinyl pot with a diameter of 9 cm (mfd. by Kaneya Shoten, having an opening with a diameter of 1 cm in the lower portion of the vessel) instead of the pot used in Example 9 which had been coated with the PNIPAAm particles. At this time, the plant was fixed by lightly pressing the support occupying the pot downward by hands in the same manner as in Reference Example 8. Further, the solution of powder horticultural fertilizer used in Example 9 was sufficiently supplied by watering onto the above support until an excess of the solution was discharged from the opening provided in the lower portion of the pot.

The plantlet was subjected to ordinary cultivation in a greenhouse (average lowest temperature 19° C., average highest temperature 26° C.) in the same manner as in Example 9 except for using the thus fixed pot. Watering during the cultivation was conducted every two or three days until an excess of water was discharged from the opening provided in the lower portion of the pot (until the support in the vessel reached the equilibrium water absorption thereof).

After 36 days counted from the initiation of the cultivation, the plantlet was taken out from the vessel and the fresh weight thereof was measured. As a result, it was found to be 3.9 g/one plantlet on average. The thus obtained plantlet showed the growth thereof which was clearly poorer than that of the plantlet which had been grown in the vessel coated with PNIPAAm particles in Example 9. When the cross section of the root which had reached the vessel wall surface or the root which had been extended in the support was observed with a microscope, substantially no root hairs were observed.

Reference Example 10

A pot was prepared in the same manner as in Example 6 except for using commercially available dried Aquaric CA-H (mfd. by Nippon Shokubai K. K., crosslinked polyacrylic acid product, indeterminate bulk shape, dimension=1 mm) instead of the PNIPAAm particles used in Example 6.

In the same manner as in Example 9 except for using the thus obtained pot, nine SJIC plantlets having an average fresh weight of 3.0 g were selected, and were transferred by using as the support 250 ml of a mixture comprising Growell MO-2 and VAPO in a mixing ratio of 8:2 (volume ratio). Further, 175 ml of a solution of powder horticultural fertilizer used in Example 9 was added to the pot.

The plantlet was subjected to ordinary cultivation in a greenhouse (average lowest temperature 19° C., average highest temperature 26° C.) by using the pot which had been fixed in the above-mentioned manner. watering during the cultivation was conducted every two or three days so that the weight of the whole vessel became the same as the initial value thereof.

Even after 36 days counted from the initiation of the cultivation of the plant, substantially no growth was observed in both of the leaf and stem portion and underground potion in its appearance. Further, when the root was observed with a microscope, substantially no root hairs were observed.

Example 10

A plantlet of SFBB (Cym. SUNSHINE FALLES "Butterball") having a leaf length of 16 cm which had been grown by use of ordinary cultivation in a greenhouse was transferred into a pot-type vessel prepared in Example 7 by using commercially available Growell MO-2 (400 ml) as the support. At this time, the operation of pressing the support (by hands) after the filling of the pot was not conducted, since such an operation is effective in fixing the plant, but it can damage the root. Into the above-mentioned pot, 175 ml of a solution of powder horticultural fertilizer used in Example 9 was added. As a result, the PNIPAAm particles disposed on the wall surface of the vessel were swollen toward the center of the vessel while absorbing the solution, and pressed the inner support (mixture of Growell MO-2 and VAPO), whereby the fixing of the plant and the attachment thereof to the support were conducted indirectly without damaging the root.

The thus fixed pot was subjected to ordinary cultivation in a greenhouse (average lowest temperature 19° C., average highest temperature 26° C.). Watering during the cultivation was conducted every two or three days so that the weight of the whole vessel became the same as the initial value thereof.

After 100 days counted from the initiation of the cultivation, the plantlet was taken out from the vessel and the fresh weight thereof was measured. As a result, it was found to be 18.2 g /one plantlet on average. The removal of the plantlet could easily be effected by immersing the plantlet together with the pot used for growth thereof in warm water (38° C.) so as to shrink the PNIPAAm particles 2b disposed on the vessel wall.

Figure 29:
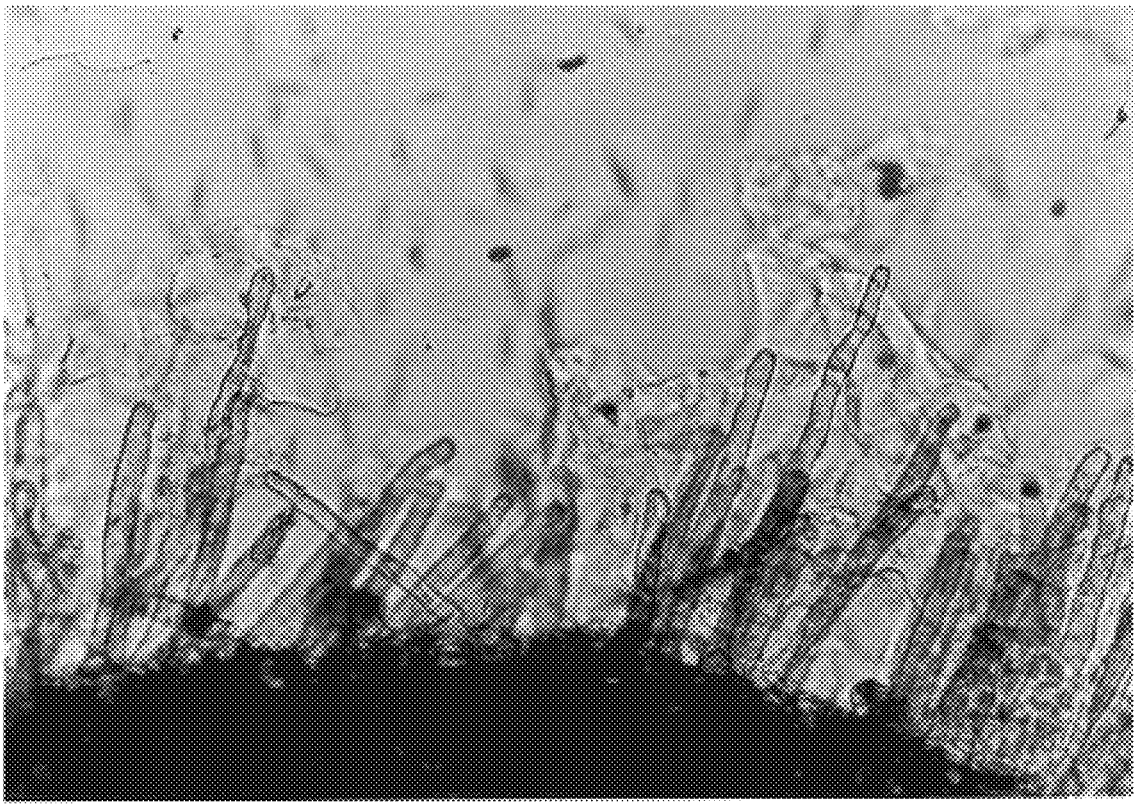
FIG. 29 is an enlarged microscopic photograph (magnification: x100 times) showing the section of a root portion of an orchid plantlet which has been grown in Example.

In the plantlet after the above-mentioned growth, the growth of the root is smooth in its appearance. Particularly, the root which had reached the vessel wall surface grew very well. Further, when the cross section of the root which had reached the vessel wall surface (about 2 cm toward the base portion side counted from the root tip) was observed with a microscope, it was found that an innumerable number of root hairs grew between the PNIPAAm particles (as shown in the microscopic photograph of FIG. 29, magnification:× 100 times). Further, the leaf and stem portion had a thick leaf color, and the growth of the whole plantlet was smooth.

Reference Example 11

In the same manner as in Example 10, an SFBB plantlet having a leaf length of 16 cm which had been grown by use of ordinary cultivation in a greenhouse was transferred into a commercially available black vinyl pot (mfd. by Kaneya Shoten, diameter ø9 cm×7 cm) in the same manner as in Example 10 by using as the support commercially available Growell MO-2 (400 ml), except for using the above black vinyl pot instead of the pot used in Example 10 which had been coated with the PNIPAAm particles. At this time, the plant was fixed by lightly pressing the support occupying the pot downward by hands. Further, the solution of powder horticultural fertilizer used in Example 10 was sufficiently supplied by watering onto the support until an excess of the solution was discharged from the opening provided in the lower portion of the pot.

The plantlet was subjected to ordinary cultivation in a greenhouse by using the thus fixed pot. Watering during the cultivation was conducted every two or three days until an excess of water was discharged from the opening provided in the lower portion of the pot (until the equilibrium water absorption of the support in the vessel was accomplished).

Figure 30:
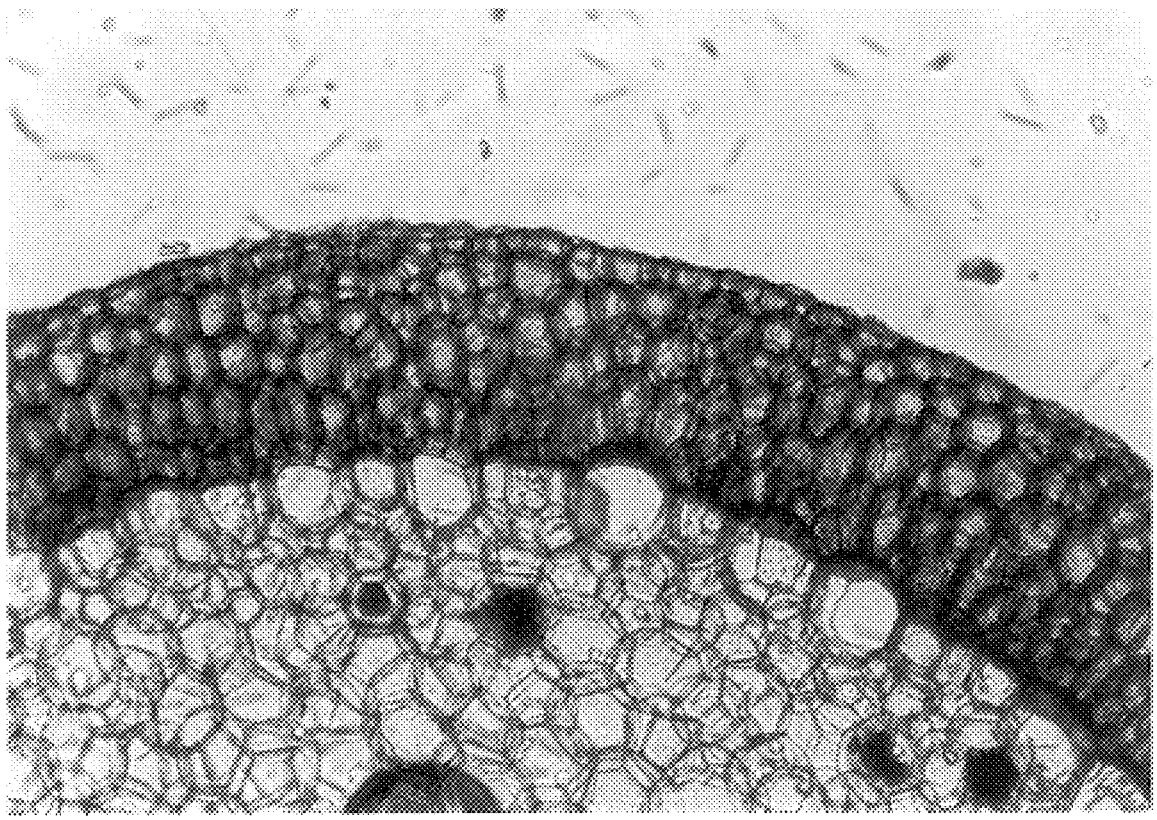
FIG. 30 an enlarged microscopic photograph (magnification: x100 times) showing the section of a root portion of a plantlet of an orchid which has been grown in Reference Example.

After 100 days counted from the initiation of the cultivation, the plantlet was taken out from the vessel and the fresh weight thereof was measured. As a result, it was found to be 12.6 g/one plantlet on average. The thus obtained plantlet showed smooth growth of the roots in its appearance. However, the growth of roots which had reached the vessel wall was such that it was clearly poorer than that obtained in Example 10, and substantially no extension in the root hairs were observed (as shown in the microscopic photograph of FIG. 30, magnification:×100 times). The leaf and stem portion showed a thin leaf color, and the growth of the whole plantlet was poor.

Example 11

In a plant box (Shibata Hario K. K., made of polycarbonate, upper part=75×75 mm, lower part 65×65 mm, height=100 mm), the grid-type sheet prepared in Example 8 was disposed, and was sterilized by an autoclave treatment (121° C., 1.2 Kg/cm2, 20 minutes).

In the above plant box, into the above nine portions, one orchid plantlet of SJKH (Cym. SARAH JEAN "Koihime") which had been sterilizedly cultured so as to provide a leaf length of about 4 cm and a root length of about 5 cm was disposed per one portion thereof.

On the other hand, the Hyponex culture medium (105 ml) used in Example 9 was sterilized by an autoclave treatment (121° C., 1.2 Kg/cm2, 20 minutes), and poured in nine compartments of the above grid-type sheet, whereby the PNIPAA particles attached to the sheet absorbed the culture medium to be swollen and the above plant (plantlet of orchid) was completely fixed.

The thus fixed plantlet of orchid was sterilizedly cultured for two months in a culturing chamber (25° C., 3000 lux, 16h-fluorescent light illumination). After about two months counted from the initiation of the culturing, when the plantlets were grown so as to provide a leaf length thereof of about 10 cm, the plant box was non-sterilizedly immersed in warm water at 35° C. for 20 minutes. As a result, the PNIPAAm particles were shrunk to be completely aggregated, and almost all of the Hyponex culture medium was discharged from the completely aggregated carrier (PNIPAAm particles).

The stopper (made of silicone) for a 5 mm-diameter opening which had provided in the above plant box in advance, was removed, and the culture medium discharged in the above step was flown out and removed. Then, the above stopper was again provided to the opening of the plant box.

About 100 mL of aqueduct water at a temperature of about 16° C. was added into the plant box, whereby the aqueduct water was absorbed into the completely aggregated PNIPAAm particles. Then the plant box was immersed in warm water of 40° C. so that the temperature of the water was again raised to about 35° C. to shrink the PNIPAAM to be converted into a completely aggregated form, whereby the aqueduct water was discharged from the beads-type carrier. In this manner, the Hyponex culture medium used for the above culture step was completely removed from the carrier of the aggregated PNIPAAm particles.

While the aggregated carrier of PNIPAAm particles and the paper sheet being attached to the root thereof, the above SJKH after the culture was transferred one by one into the pot coated with PNIPAAm particles (vessel prepared in Example 6) in the same manner as in Example 9 except for using the Growell MO-2 as the support, and 200 ml of the solution of the horticultural fertilizer used in Example 9 was added thereto. At this time, the PNIPAAm particles attached to the grid-type sheet and the plant absorbed the fertilizer solution, and the PNIPAAm particles disposed on the vessel wall were swollen toward the center of the vessel while absorbing the solution, and pressed the inner support (Growell MO-2), whereby the suitable fixing of the plant and the attachment thereof to the support were conducted indirectly without damaging the root.

The SJKH which had been transferred into the pot in this manner was subjected to ordinary cultivation in a greenhouse. In this cultivation in the greenhouse, watering was effected every three or four days so that the weight of the whole pot became the same as the initial value thereof.

After 50 days counted from the initiation of the cultivation in the above-mentioned greenhouse, the appearance of thus obtained SJKH plantlet was observed. As a result, the root was well extended, and there were observed many plantlets wherein new root was originated from the base portion thereof. Further, when the cross section of the root which had reached the vessel wall surface (about 2 cm toward the base portion side counted from the root tip) was observed with a microscope, it was found that an innumerable number of root hairs grew between the PNIPAAm particles. Further, the leaf and stem portion had a thick leaf color, and the growth of the plantlet was very good.

Reference Example 12

In a plant box (Shibata Hario K. K., made of polycarbonate, upper part=75×75 mm, lower part 65×65 mm, height=100 mm), 105 ml of the Hyponex culture medium (to which agar had been added so as to provide a concentration of 7 g/L) was poured, and was sterilized by an autoclave treatment (121° C., 1.2 Kg/cm2, 20 minutes), and left standing at room temperature.

In the same manner as in Example 11, nine plantlets of SJKH which had been sterilizedly cultured so as to provide a leaf length of about 4 cm and a root length of about 5 cm were transferred by using forceps. At this time, the transferring of the plantlet required a considerable length of time, and some physical damage such as breakage of the root could not be avoided.

The plantlet was sterilizedly cultured for two months in a culturing chamber (25° C., 3000 lux, 16h-fluorescent light illumination). After about two months counted from the initiation of the culturing, when the plantlets were grown so as to provide a leaf length thereof of about 10 cm, the plantlet was taken out of the vessel and the culture medium attached to the root thereof was removed under flow of water. At this time, the removal of the agar culture medium by manual operation required a long period of time and the root was damaged.

The SJKH plantlet obtained by the above growth method was transferred one by one into a black vinyl pot (diameter ø9cm×7 cm) by using Growell MO-2 as the support. At the time, the plant was fixed by pressing the support occupying the pot. Further, the solution of powder horticultural fertilizer used in Example 9 was sufficiently supplied into the vessel until an excess of the solution was discharged from the opening provided in the lower portion of the pot.

The plantlet was subjected to ordinary cultivation in a greenhouse in the same manner as in Example 11 except for using the above plantlet which had been transferred into the black vinyl pot. Watering during the cultivation was conducted every three or four days until an excess of water was discharged from the opening provided in the lower portion of the pot (until the equilibrium water absorption of the support in the vessel was accomplished).

After 50 days counted from the initiation of the cultivation in the above-mentioned greenhouse, the a appearance of the plantlet was observed. As a result, it was found that the root which had been damaged at the time of the transferring assumed browning and fatal withering. Further, when the cross section of the root which had reached the vessel wall surface (about 2 cm toward the base portion side counted from the root tip) was observed with a microscope, it was found that substantially no root hairs grew. Further, the leaf and stem portion had a thin leaf color, and the growth of the whole plantlet was slow.

Example 12

(Method of measuring water evaporation rate)

The solid component constituting each of the following plant-growing systems (culturing vessel and dry polymer; weight: $W_1$ (g)) was measured by means of a precise balance (an electronic balance mfd. by Shimazu Seisakusho K. K., trade name: LIBROR-EB-3200D). Then, a liquid component (liquid culture medium) was added to the above solid component and the resultant total weight ($W_2$) was measured by the same precise balance. The precise weight of the above liquid component was calculated as ($X=W_2-W_1$).

After the plant was transferred into the above-mentioned growing system, the resultant total weight Y of the whole growing system inclusive of the plant was measured by means of the same precise balance.

After the above total weight Y was measured, there was measured the total weight Z of the whole growth system, inclusive of the water evaporation rate Zd after one day (24 hours), water evaporation rate Zw after one week (7 days), and/or water evaporation rate Zm after one month (30 days)). By use of the thus obtained weight Z, the water evaporation rate was determined by using the following calculation formula.

Water evaporation rate (%/24 hour)=100×(Y−Zd)/X,

Water evaporation rate (%/24 hour)=100×(Y−Zw)/(X×7), or

Water evaporation rate (%/24 hour)=100×(Y−Zm)/(X×30)

<Condition-1> conventional sugar-involving culture using agar
(Sugar-involving agar culture condition)
Size and material vessel: diameter of 9 cm, height of 18 cm, capacity 950 ml; glass
Size and material of lid: diameter of 7 cm, TPX resin,
Weight of agar: 0.12 g
Material of filter: filter paper
Total area of filter: 0.5 cm$^2$
Amount of saccharide: 4 wt. %
X=200 g, Y=532 g, Zm=528.4 g (Zd and Zw were in an error range of the electronic balance since the change of weight was little.)
Water evaporation rate (24 hour)=100×(532− 528.4)/(200×30)=0.06%

<Condition-2>
The conditions were the same as those in the above <condition-1> except that a sugar-free culture medium was used and the filter area was 7.6 times that of the <condition-1>.
X=200 g, Y=532 g, Zw=525 g (Zd was in an error range of the electronic balance since the change of weight was little.)

Water evaporation rate (24 hour)=100×(532−525)/(200×7)=0.5%

<Condition-3>
The conditions were the same as those in <condition-2> except that the initial quantity of water X=100 g.
X=100 g, Y=432 g, Zw=425 g (Zd was in error range of electronic balance since the change of weight was little.)

water evaporation rate (24 hour)=100×(432−425)/(100×7)=1.0%

<Condition-4>
The conditions were the same as those in <condition-2> except that the initial quantity of water X=50 g.
X=50 g, Y=382 g, Zw=375 g (Zd was in an error range of the electronic balance since the change of weight was little.)

water evaporation rate (24 hour)=100×(382−375)/(50×7)=2.0%

<Condition-5>
The conditions were the same as <condition-2> except that the lid on the vessel upper portion was removed therefrom.
X=200 g, Y=525 g, Zd=515 g Water evaporation rate (24 hour)=100×(525−51)/(200)=5.0%

<Condition-6>
The growth was effected in a culturing chamber, like a so-called "cell-plantlet"; the above-ground portion was open.
(Culture condition)
Size of the vessel and material: Upper portion 2×2 cm (substantially tetragon), lower portion 1×1 cm, height 4 cm, 10 compartments (2×5), high impact polystyrene
Lid: none
Weight of agar: 0.06 g
Weight of saccharide: 0
X=100 g, Y=170 g, Zd=138.8 g Water evaporation rate (24 hour)=100×(170−38.8)/(100)=31.2%

<Condition-7>
The growth was conducted in a greenhouse in a pot-plantlet-type manner; the above-ground portion was open.
The temperature was changed in the range of 18–28° C., and the humidity was changed in range of 50–99% since this condition was conducted in a greenhouse.
(Culture condition)
Size of the vessel and material: diameter of 11 cm, height of 7.2 cm; polystyrene
lid: none
Weight of agar: 0.15 g
Weight of saccharide: 0
X=250 g, Y=265 g, Zd=245 g Water evaporation rate (24 hours)=100×(265−245)/(250)=8.0%

Example 13

In a plant box (Shibata Hario K. K., made of polycarbonate, upper part=75×75 mm, lower part 65×65 mm, height=100 mm), 3 g of the dry C-PNIPAAm-H powder prepared in Example 1 was mixed with and dispersed in 150 mL of a Hyponex liquid culture medium (Hyponex 7-6-19, mfd. by Hyponex Japan K. K., 3.5 g/l, containing 2 g/L of activated charcoal). The thus obtained dispersion liquid was sterilized by an autoclave treatment (121° C., 1.2 Kg/cm2, 20 minutes), and left standing at room temperature. As a result, the C-PNIPAAm-H polymer powder completely absorbed the culture medium to be converted into a gel state.

Onto the surface of the gel disposed in the plant box, orchid plantlets of MFM (Cym. MELODY FAIR 'Marilyn Monroe') were transferred so as to provide almost equal intervals between the plantlets (four columns×four lines), and were cultured under a sterilized condition in a culturing chamber (25° C., 3000Lux, 16h-fluorescent light illumination).

After 70 days from the initiation of the culturing, the lid of the plant box was opened, and 75 ml of a Hyponex solution (Hyponex 7-6-19, 1 g/L) was added thereto, so that the C-PNIPAAm-H which had been shrunk due to the evaporation of water during the culturing and water absorption by the plant was caused to again absorb water. Then, the plantlet was subjected to continuous cultivation in a greenhouse while the lid of the vessel was remained open. Watering was conducted for every three or four days so that weight of the whole vessel became the same as the initial value thereof.

After 60 days counted from the initiation of the cultivation in a greenhouse, the plantlet was taken out from the vessel one by one for the purpose of transferring the plantlet into single-pot cultivation. The above-ground portion of the plantlet grew smoothly, but the removal of the plantlet required a somewhat amount of period of time since the root was entangled with each other to a certain extent. Further, the elongation of the root after the transfer thereof into the greenhouse cultivation was somewhat poorer as compared with that in case of Example 14 appearing hereinafter.

The thus grown plantlet, to the root of which the above-mentioned gel was attached was transferred to a Type-3 black vinyl pot (diameter of 9 cm, mfd. by Kaneya Shoten) while disposing Growell MO-2 (available from Mukoyama Orchid Co., Ltd., bark produced in New Zealand) therearound, and was subjected to ordinary cultivation in a greenhouse. Even after 60 days, the plantlet was smoothly grown.

Reference Example 13

In the same plant box as that used in Example 13, 0.9 g of agar was mixed with and dispersed in 150 ml of Hyponex liquid culture medium used Example 13. The resultant dispersion liquid was sterilized in an autoclave in the same manner as in Example 13, and was left standing at room temperature thereby to completely convert the culture medium into a gel state.

Onto the gel surface disposed in plant box in this manner, 16 orchid plantlets of MFMM were transferred and was cultured in a culturing chamber in the same manner as in as Example 13.

After 70 days, the lid of the plant box was opened and 75 ml of the Hyponex solution used in Example 13 was added. However, the agar gel which had been shrunk due to the water evaporation in the culturing and water absorption by the plant, did not substantially absorb the solution.

The plantlet was continuously cultivated in a greenhouse in the same manner as in as Example 3 while the lid of the plant box remained open. Watering was conducted every three or four days so that the weight of the whole vessel became the same as the initial value thereof.

After 30 days counted from the initiation of the cultivation, various germs were propagated on the support, and the lower leafs of the plantlet and most of the roots were decayed, and the cultivation thereafter became impossible.

Example 14

In the same plant box used in Example 13, 2.31 g of the dry C-PNIPAAm-H prepared in Example 1 and 7.2 g of Asano-Pearlite (Nihon Cement K. K.) as a porous material were mixed with and dispersed in 150 ml of Hyponex liquid culture medium used in Example 13. The resultant dispersion liquid was divided into 16 divisions by using a grid-type polyester sheet (thickness 0.15 mm, height 25 mm, mfd. by Toray Co.), was sterilized by using an autoclave, and left standing at room temperature, whereby the C-PNIPAAm-H absorbed the liquid culture medium to be converted into a gel state. The "apparent volume ratio" of the polymer gel and Asano-Pearlite at room temperature (25° C.) was about 1:1.

In this manner, 16 divisions were provided in the plant box by using the grid-type polyester sheet as shown in the schematic perspective view of FIG. 26 (FIG. 26 shows an example of 9 divisions). Onto the thus divided gel surface, an orchid plantlet of MFMM was transferred so as to dispose one plantlet in one division (total 16 plantlets), and was cultured in a culturing chamber in the same manner as in Example 13.

After 70 days counted from the initiation of the culture, the lid of plant box was opened, and 75 ml of the Hyponex solution used in Example 13 was added thereto, so that the C-PNIPAAm-H which had been shrunk due to the evaporation of water and water absorption by the plant again absorbed the Hyponex solution. Thereafter, the plantlet was continuously cultivated in a greenhouse in the same manner as Example 13 while the lid of the plant box remained open. Watering was effected for every three or four days so that the weight of the whole vessel became the same as the initial value thereof.

After 60 days counted from the initiation of the cultivation, the plantlet was taken out one by one in order to transfer to the single-pot cultivation. At this time, the entanglement between the roots was effectively prevented by the grid-type sheet, and the removal of the plantlet was easy. The above-ground portion of the plantlet grew smoothly, and the growth of the root after the transfer to the greenhouse cultivation was also good. According to the investigation of the present inventors, it was presumably considered that the smooth elongation of the root was attributed to the preliminary addition of Asano-Pearlite to the culturing medium as a porous material.

The plantlet was transferred to a Type-3 black vinyl pot while the support of (gel+porous material) was attached to the root, by disposing Growell MO-2 around the outside thereof in the same manner as in Example 13, and was subjected to ordinary cultivation in greenhouse. Even after 60 days counted from the initiation of the single-pot cultivation, the plantlet was grown smoothly.

Reference Example 14

In the same plant box used in Example 13, 0.7 g of agar and 7.2 g of Asano-Pearlite (Nihon Cement K. K.) were mixed with and dispersed in 150 ml of the Hyponex liquid culture medium used in Example 13. Then, in the same manner as in Example 14, the resultant dispersion liquid was divided into 16 divisions by using a grid-type polypropylene sheet, was sterilized by using an autoclave, and left standing at room temperature, thereby to convert the liquid culture medium into a gel state.

Onto the thus obtained gel surface, 16 plantlets of MFMM were transferred, and were culture in a culturing chamber in the same manner as in Example 14. After 70 days counted from the initiation of the culturing, the lid of plant box was opened, and 75 ml of the Hyponex solution used in Example 13 was added thereto. However, the agar gel which had been shrunk due to the evaporation of water and water absorption by the plant did not substantially absorbed again the solution.

Thereafter, the plantlets were continuously cultivated in a greenhouse in the same manner as Example 14 while the lid of the plant box remained open. Watering was effected for every three or four days so that the weight of the whole vessel became the same as the initial value thereof.

After 30 days counted from the initiation of the cultivation in the greenhouse, various germs were propagated on the support, and lower leaves and most of the roots of the plantlets were decayed, and the cultivation thereafter became impossible. Accordingly, in this Reference Example, the addition of the Asano-Pearlite, and the 16-division formation by the grid-type polypropylene sheet became meaningless.

Example 15

In the same plant box used in Example 13, 3 g of the dry C-PNIPAAm-H prepared in Example 1 was mixed with and dispersed in 150 ml of Hyponex saccharide-containing liquid culture medium (mfd. by Hyponex Japan K. K., 3.5 g/L, containing 30 g/L of sucrose and 2 g/L of activated carbon). The resultant dispersion liquid was sterilized by using an autoclave, and left standing at room temperature, whereby the C-PNIPAAm-H absorbed the liquid culture medium to be completely converted into a gel state.

In the thus obtained gel, 16 orchid plantlets of RG310 (Cym. ENZAN SYMPHONY 'RG310') were transferred in the same manner as in as Example 13, and cultured in a culturing chamber.

After 70 days counted from the initiation of the culturing, the plant box was immersed in warm water at 35° C. for 20 minutes. As a result, the C-PNIPAAm-H particles were shrunk and almost all of the culture medium which had been contained in the carrier was discharged from the carrier.

The lid of the plant box was opened and the above discharged culture medium was sucked by using a dropping pipette, and then about 150 mL of aqueduct water at a temperature of about 16° C. was added to the plant box, whereby the aqueduct water was absorbed into the C-PNIPAAm-H particles. The temperature was again raised to about 35° C. to shrink the C-PNIPAAm-H particles, whereby the aqueduct water was discharged from the carrier. This operation was repeated twice. Thereafter, when the sugar concentration of the discharged aqueduct water was measured by means of a refractometer (trade name: Ni, mfd. by Atago K. K.), the content was found to be below the detection limit thereof (0.2 wt. %).

Then, 75 ml of the Hyponex solution used in Example 13 was added into the plant box, so that the C-PNIPAAm-H particles which had again been shrunk were caused to again absorb the solution, to be converted into a gel state. Then, the plantlets were subjected to continuous cultivation in a greenhouse in the same manner as in Example 13, while the lid of the vessel was remained open. Watering was conducted for every three or four days so that weight of the whole vessel became the same as the initial value thereof.

After 60 days counted shape the initiation of the cultivation in the greenhouse, the plantlet was taken out from the vessel one by one for the purpose of transferring the plantlet into single-pot cultivation. The above-ground portion of the plantlet grew smoothly, but the removal of the plantlet required a somewhat amount of period of time, since the roots were entangled with each other to a certain extent. Further, the elongation of the root after the transfer thereof into the greenhouse cultivation was somewhat poorer as compared with that in case of Example 16 appearing hereinafter.

The thus grown plantlet, to the root of which the above-mentioned gel was attached was transferred to a Type-3 black vinyl pot while disposing Growell MO-2 therearound in the same manner as in Example 13, and was subjected to ordinary cultivation in a greenhouse. Even after 60 days, the plantlet was smoothly grown.

Reference Example 15

In the same plant box used in Example 13, 0.9 g of agar was mixed with and dispersed in 150 ml of the saccharide-containing Hyponex liquid culture medium used in Example 15. Then, in the same manner as in Example 13, the resultant dispersion liquid was sterilized by using an autoclave, and left standing at room temperature, thereby to completely convert the liquid culture medium into a gel state.

Onto the thus obtained gel surface, 16 orchid plantlets of RG310 were transferred, and were cultured in a culturing chamber in the same manner as in Example 15. After 70 days counted from the initiation of the culturing, the lid of plant box was opened, and the plantlets were continuously cultivated in a greenhouse. After two days counted from the initiation of the cultivation in the greenhouse, various germs were propagated on the agar gel, and after one week, various germs were also propagated even on the plantlets per se, and the plantlets assumed browning and fatal withering, and the cultivation thereafter became impossible.

Example 16

In the same plant box used in Example 13, 2.31 g of the dry C-PNIPAAm-H prepared in Example 1 and 7.2 g of Asano-Pearlite as a porous material were mixed with and dispersed in 150 ml of Hyponex saccharide-containing liquid culture medium used in Example 15. The resultant dispersion liquid was divided into 16 divisions by using a grid-type polypropylene sheet, was sterilized by using an autoclave, and left standing at room temperature in the same manner as in Example 14, whereby the C-PNIPAAm-H absorbed the liquid culture medium to be completely converted into a gel state. The "apparent volume ratio" of the polymer gel and Asano-Pearlite at room temperature (25° C.) was about 1:1.

Onto the thus 16-divided gel culturing medium surface, an orchid plantlet of RG-310 was transferred so as to dispose one plantlet in one division (total 16 plantlets), and was cultured in a culturing chamber in the same manner as in Example 15. After 70 days counted from the initiation of the culture, the plant box was immersed in warm water at 35° C. for 20 minutes. As a result, the C-PNIPAAm-H carrier was shrunk and almost all of the culture medium which had been contained in the carrier was discharged from the carrier. Then, the lid of the plant box was opened and the above discharged culture medium was sucked by using a dropping pipette, and then the plant box was left standing at normal temperature (25° C.), whereby the culturing liquid medium contained in the pores and voids of Asano-pearlite was absorbed into the shrunken C-PNIPAAm-H.

Thereafter, about 150 mL of aqueduct water at a temperature of about 16° C. was added to the plant box, whereby the aqueduct water was absorbed into the C-PNIPAAm-H. The temperature was again raised to about 35° C. to shrink the C-PNIPAAm-H, whereby the aqueduct water was discharged therefrom. This operation was repeated three times. Then, when the sugar concentration of the discharged aqueduct water was measured by means of a refractometer, the content was found to be below the detection limit thereof (0.2 wt. %).

Then, 150 ml of the Hyponex solution used in Example 13 was added into the plant box, so that the C-PNIPAAm-H particles which had again been shrunk were caused to again absorb the solution, to be converted into a gel state. Then, the plantlets were subjected to continuous cultivation in a greenhouse in the same manner as in Example 13, while the lid of the vessel was remained open. Watering was conducted for every three or four days so that weight of the whole vessel became the same as the initial value thereof.

After 60 days counted shape the initiation of the cultivation in the greenhouse, the above C-PNIPAAm-H was shrunk by immersing the vessel in warm water at 35° C. for 20 minutes, and then the plantlet was taken out from the vessel one by one for the purpose of transferring the plantlet into single-pot cultivation. At this time, the support was shrunk due to the temperature increase in each of the sections divided by the grid, and further the entanglement between the roots of the plantlets was effectively prevented by the partition of the grid, and therefore the plantlet could easily be taken out from the vessel. The above-ground portion of the plantlet grew smoothly, and the elongation of the root after the transfer thereof into the greenhouse cultivation was also smooth. It was presumably considered that the smooth growth of the root was attributable to the preliminary addition of the Asano-pearlite to the culture medium.

The thus grown plantlet, to the root of which the above-mentioned gel was attached was transferred to a Type-3 black vinyl pot while disposing Growell MO-2 therearound, and was subjected to ordinary cultivation in a greenhouse. Even after 60 days, the plantlet was smoothly grown.

Reference Example 16

In the same plant box used in Example 13, 0.7 g of agar and 7.2 g of Asano-Pearlite were mixed with and dispersed in 150 ml of the Hyponex saccharide-containing liquid culture medium used in Example 15. Then, the resultant dispersion liquid was divided into 16 divisions by using a grid-type polypropylene sheet, was sterilized by using an autoclave, and left standing at room temperature, thereby to completely convert the liquid culture medium into a gel state.

Onto the thus obtained gel surface, 16 plantlets of RG310 were transferred, and were cultured in a culturing chamber in the same manner as in Example 16. After 70 days counted from the initiation of the culturing, the lid of plant box was opened, and the plantlets were continuously cultivated in a greenhouse as it was. After two days counted from the initiation of the cultivation in the greenhouse, various germs were propagated on the support, and after one week, various germs were also propagated even on the plantlets per se, and the plantlets assumed browning and fatal withering, and the cultivation thereafter became impossible. Accordingly, in this Reference Example, the addition of the Asano-Pearlite, and the 16-division formation by the grid-type polypropylene sheet became meaningless.

Industrial Applicability

As described herein the above, according to the present invention, there is provided a plant-cultivating support or soil-modifying agent, comprising a hydrogel-forming polymer having a crosslinked structure and showing a decrease in the equilibrium water absorption thereof along with an increase in temperature in the temperature range of not lower than 0° C. and not higher than 70° C., the equilibrium water absorption being reversibly changeable with respect to temperature.

The present invention further provides a plant-cultivating support, comprising, at least a carrier for supporting a plant; and a soil-modifying agent, comprising a hydrogel-forming polymer having a crosslinked structure and showing a decrease in the equilibrium water absorption thereof along with an increase in temperature in the temperature range of not lower than 0° C. and not higher than 70° C., the equilibrium water absorption being reversibly changeable with respect to temperature.

The present invention further provides a method of cultivating a plant, comprising:

disposing a plant-cultivating support at least around a plant; and cultivating the plant while supporting the plant by the plant-cultivating support;

wherein the plant-cultivating support comprises a hydrogel-forming polymer having a crosslinked structure and showing a decrease in the equilibrium water absorption thereof along with an increase in temperature in the temperature range of not lower than 0° C. and not higher than 70° C., the equilibrium water absorption being reversibly changeable with respect to temperature.

The present invention further provides a method of cultivating a plant, comprising:

disposing a plant-cultivating support at least around a plant; and cultivating the plant while supporting the plant by the plant-cultivating support;

wherein the plant-cultivating support comprises a plant-supporting carrier, and a soil-modifying agent added to the carrier in an amount of 0.1–10 wt., in terms of the weight in a dry state; the soil-modifying agent comprising a hydrogel-forming polymer having a crosslinked structure and showing a decrease in the equilibrium water absorption thereof along with an increase in temperature in the temperature range of not lower than 0° C. and not higher than 70° C., the equilibrium water absorption being reversibly changeable with respect to temperature.

When the above plant-cultivating support or soil-modifying agent according to the present invention comprising the hydrogel-forming polymer or hydrogel showing a predetermined temperature-responsive property is used, it is possible that at the time of the cultivation of plant or crop (grain plant, vegetables, flowering plants, fruit trees, etc.), the above-mentioned hydrogel or polymer can be caused to absorb or discharge the component such as water, nutrient, and a plant growth-regulating substance, in accordance with the demand of the plant for such a component, in response to a change in the external environmental factor (such as temperature, humidity, quantity of solar radiation, and light intensity). In other words, it is possible that the growth of a plant is regulated by supplying thereto such a component in a suitably changeable manner, and/or that the plant is caused to exhibit its function of promoting the growth thereof by lessening the adverse effect of the above-mentioned external environmental factor.

Therefore, according to the present invention, it is possible to suitably control the supply of a component such as water and nutrient relating to the growth of the plant, so that various problems (troublesome regulation of cultivating conditions, high apparatus cost) encountered in the prior art in the field of cultivation such as field cultivation and horticulture in facility, and further the labor or energy required for the cultivation is reduced, cost of the cultivating apparatus is reduced, thereby to enhance the productivity.

The present invention further provides a vessel for growing a plant, comprising: a base material in the form of a vessel which is capable of accommodating therein at least a part of a plant; and a hydrogel-forming polymer disposed in the inside of the vessel-form base material; the hydrogel-forming polymer having a crosslinked structure.

The present invention further provides a sheet for growing a plant, comprising: a base material in the form of a sheet; and a hydrogel-forming polymer disposed on at least one of the surfaces of the sheet; the hydrogel-forming polymer having a crosslinked structure.

When the plant-growing vessel or sheet according to the present invention is used, the volume of the plant-growing vessel may remarkably be reduced, on the basis of the characteristic of the hydrogel-forming polymer having a crosslinked structure disposed on the plant side of the vessel or sheet (ability of string water content or nutrient, or the temperature dependency thereof), and therefore the efficiency in the root origination can be improved, the area required for the growth is reduced, the amount of the material of the growing vessel can be reduced, and the transportation cost can be reduced. Further, cost can be reduced remarkably by saving labor for water control, etc.

The present invention further provides a method of growing a plant, comprising:

(a) culturing a plant under a ventilation-restricted condition by using a gel-type support comprising at least water and a hydrogel-forming polymer having crosslinked structure; and (b) cultivating the plant under a ventilation non-restricted condition by using the gel-like support disposed in contact with the plant after the culturing, substantially as it is.

According to the plant-growing method according to the present invention, in the transfer from culture (ventilation-restricted condition) to cultivation (ventilation non-restricted condition), the plant can continuously be grown by effectively utilizing the bacteriostatic property of the hydrogel, while the exchange of the support or planting material is not necessarily conducted.

We claim:

1. A support for cultivating a plant, comprising a hydrogel-forming polymer having a crosslinked structure, the hydrogel-forming polymer showing a decrease in equilibrium water absorption with an increase in temperature in a temperature range from 0° C. to 70° C. wherein the ratio ($E_L/E_H$) of equilibrium water absorption $E_H$ at 50° C. to an equilibrium water absorption $E_L$ at 5° C. of the hydrogel-forming polymer is at least 2.

2. The support for cultivating a plant according to claim 1, wherein water is retained in the crosslinked structure of the hydrogel-forming polymer to form a hydrogel containing the hydrogel-forming polymer.

3. The support for cultivating a plant according to claim 1, wherein a nutrient is retained in the crosslinked structure.

4. The support for cultivating a plant according to claim 1, wherein a plant growth-regulating substance is retained in the crosslinked structure.

5. A support for cultivating a plant according to claim 1, wherein a dimension of hydrogel-forming polymer in a dry state is in the range of 0.1 μm–1 cm, and the shape thereof is any of a micro-bead-type, a fiber-type, a sponge-type or an indeterminate-type.

6. A support for cultivating a plant, comprising:
a carrier for supporting a plant; and
a soil-modifying agent comprising a hydrogel-forming polymer having a crosslinked structure, the hydrogel-forming polymer showing a decrease in equilibrium water absorption with an increase in temperature in a temperature range from 0° C. to 70° C. wherein the ratio ($E_L/E_H$) of equilibrium water absorption $E_H$ at 50° C. to an equilibrium water absorption $E_L$ at 5° C. of the hydrogel-forming polymer is at least 2.

7. The support for cultivating a plant according to claim 6, wherein the plant-supporting carrier comprises at least one kind of carrier selected from the group consisting of: soil, gravel, sand, pumice, carbide, peat, vermiculite, bark, pearlite, zeolite, rock wool, sponge, peat-moss, crushed coconut shell and crypo-moss.

8. The support for cultivating a plant according to claim 6, wherein the hydrogel-forming polymer has been added to the plant-supporting carrier in an amount of 0.1–10 wt., in terms of the weight in a dry state.

* * * * *